(12) United States Patent
Dessein et al.

(10) Patent No.: US 10,150,989 B2
(45) Date of Patent: Dec. 11, 2018

(54) FIBROSIS SUSCEPTIBILITY IL22RA2 GENE AND USES THEREOF

(75) Inventors: Alain Dessein, Marseilles (FR); Mathieu Sertorio, Saint Ismier (FR); Laurent Argiro, Marseilles (FR)

(73) Assignees: UNIVERSITE D'AIX MARSEILLE, Paris (FR); INSERM, Paris (FR)

( * ) Notice: Subject to any disclaimer, the term of this patent is extended or adjusted under 35 U.S.C. 154(b) by 167 days.

(21) Appl. No.: 14/236,869

(22) PCT Filed: Aug. 3, 2012

(86) PCT No.: PCT/EP2012/065222
§ 371 (c)(1),
(2), (4) Date: Jun. 13, 2014

(87) PCT Pub. No.: WO2013/020904
PCT Pub. Date: Feb. 14, 2013

(65) Prior Publication Data
US 2014/0295427 A1  Oct. 2, 2014

Related U.S. Application Data

(60) Provisional application No. 61/515,438, filed on Aug. 5, 2011.

(30) Foreign Application Priority Data

Aug. 5, 2011  (EP) .................................. 11306018

(51) Int. Cl.
*C12Q 1/68* (2018.01)
*C12Q 1/683* (2018.01)
*C12Q 1/6883* (2018.01)
*C12Q 1/6827* (2018.01)

(52) U.S. Cl.
CPC ........... *C12Q 1/683* (2013.01); *C12Q 1/6827* (2013.01); *C12Q 1/6883* (2013.01); *C12Q 2539/10* (2013.01); *C12Q 2600/106* (2013.01); *C12Q 2600/156* (2013.01)

(58) Field of Classification Search
CPC ............................ C12Q 1/6827; C12Q 1/6883
See application file for complete search history.

(56) References Cited

U.S. PATENT DOCUMENTS

| 9,297,044 | B2 | 3/2016 | Dessein et al. |
|---|---|---|---|
| 2003/0092019 | A1 | 5/2003 | Meyer et al. |
| 2010/0111898 | A1* | 5/2010 | Pelura ................ A61K 38/1716 424/85.2 |
| 2012/0135403 | A1 | 5/2012 | Dessein et al. |
| 2013/0203054 | A1 | 8/2013 | Dessein et al. |
| 2016/0230232 | A1 | 8/2016 | Dessein et al. |

FOREIGN PATENT DOCUMENTS

| WO | WO 9511995 A1 | 5/1995 |
|---|---|---|
| WO | WO 96/38172 A1 | 12/1996 |
| WO | WO 03024308 | 3/2003 |
| WO | WO 2004 085476 A2 | 10/2004 |
| WO | WO 2005/050203 A2 | 6/2005 |
| WO | WO 2007 076422 A2 | 7/2007 |
| WO | WO 2008070117 | 6/2008 |
| WO | WO 2010 094740 | 8/2010 |

OTHER PUBLICATIONS

Beyeen et al J Immunology. Nov. 2010. 185: 6883-6890.*
StatSoft (Electronic Statistics Textbook; available via url: <statsoft.com/textbook/elementary-statistics-concepts/>; printed Nov. 13, 2012, pp. 1-3.*
Hirschhorn et al. Genetics in Medicine. vol. 4, No. 2, pp. 45-61, Mar. 2002.*
Lucentini et al The Scientist (2004) vol. 18, p. 20.*
Hattersley et al. The Lancet. 2005. 366: 1315-1323.*
Gagneux et al. (Molecular Phylogenetics and Evolution. 2001. 18: 2-13.*
Mummidi et al Journal of Biological Chemistry 2000 vol. 275 No. 25 pp. 18946-18961.*
NCBI SNP Database for rs2064501, ss66579593.National Center for Biotechnology Information (Bethesda, MD, USA) Nov. 9, 2006).*
Kamatani et al. Nature Genetics. May 2009. 41(5): 591.*
NCBI SNP Database for rs2064501 (ss67221252, National Center for Biotechnology Information (Bethesda, MD, USA) Nov. 14, 2006.*
Dessein et al., Variants of CTGF are associated with hepatic fibrosis in Chinese, Sudanese, and Brazilians infected with Schistosomes. Journal of Experimental Medicine, 206(11):2321-2328 (2009).
U.S. Appl. No. 13/201,520 Office Action dated Mar. 13, 2013.
U.S. Appl. No. 13/201,520 Office Action dated Sep. 25, 2012.
U.S. Appl. No. 13/201,520 Office Action dated Jun. 23, 2015.
U.S. Appl. No. 13/695,854 Office Action dated Apr. 16, 2015.
U.S. Appl. No. 13/695,854 Office Action dated Jun. 24, 2014.
U.S. Appl. No. 13/695,854 Office Action dated Aug. 10, 2015.
Kawaguchi et al., Association study of a polymorphism of the CTGF gene and susceptibility to systemic sclerosis in the Japanese population. Ann Rheum Dis, 88:1921-1924 (2009).
U.S. Appl. No. 13/201,520 Advisory Action Before the filing of an Appeal Brief dated Sep. 22, 2014.

(Continued)

*Primary Examiner* — Carla J Myers
(74) *Attorney, Agent, or Firm* — Wilson Sonsini Goodrich & Rosati

(57) ABSTRACT

The present invention discloses the identification of a fibrosis susceptibility gene locus, the IL22RA2 gene locus, which can be used for detecting predisposition to, diagnosis and prognosis of fibrosis as well as for the screening of therapeutically active drugs. The invention further provides a method for determining the likelihood of a patient affected with a viral infection to respond to a treatment with an antiviral agent and/or an interferon, which method comprises determining alteration in IL22RA2 gene locus or in IL22RA2 expression or IL22RA2 protein activity in a biological sample of the patient.

12 Claims, 5 Drawing Sheets

Specification includes a Sequence Listing.

(56) References Cited

OTHER PUBLICATIONS

U.S. Appl. No. 13/201,520 Applicant Initiated Interview Summary dated Oct. 23, 2014.
U.S. Appl. No. 13/201,520 Applicant Initiated Interview Summary dated Nov. 7, 2014.
U.S. Appl. No. 13/201,520 Applicant Initiated Interview Summary dated Sep. 22, 2014.
Arnaud, V. "Regulatory role of interleukin—10 and interferon-gamma in severe hepatic central and peripheral fibrosis in humans infected with Schistosoma japonicum" The Journal of Infectious Deseases, Aug. 1, 2008, vol. 198, pp. 418-426.
Abreu, J. G. "Connective tissue growth factor (CTGF) modulates cell signalling by BMP and TGFbeta" NAT CELL BIOL, 2002, vol. 4, p. 599.
Aparcio E., "IL28B SNP rs8099917 is strongly associated with pegylated interferon-alpha and ribavirin therapy treatment failure in HCV-HIV-1-coinfected patients", Antiviral Therapy, Jun. 2010 vol. 15, Supp. 2, p. A119.
Aparicio, E. et al., "IL28B SNP rs8099917 Is Strongly Associated with Pegylated Interferon-a and Ribavirin Therapy Treatment Failure in HCV/HIV-1 Coinfected Patients", PLoSONE, Oct. 2010, vol. 5, Issue 10.
Backus et al., "M1785 Predictors of Sustained Virologic Response to Pegylated Interferon and Ribavirin in a National Cohort of Male HIV/HCV-Coinfected Veterans in Routine Medical Care", Gastroenterology, May 2009, vol. 136, No. 5, Suppl. 1, p. A837.
Bedossa P., "The METAViR cooperative study group. An algorithm for the grading of activity in chronic hepatitis C" Hepatology, 1996, vol. 24, pp. 289-293.
Benner et al. "Evolution, Language in functional genomics" Trends in Genetics 2001, vol. 17, pp. 414-418.
Blanton et al., "Schistosomal hepatic fibrosis and the interferon gamma receptor: a linkage analysis using single-nucleotide polymorphic markers" European Journal of Human Genetics, May 1, 2005, vol. 13, No. 5, pp. 660-668.
Blom et al., "Identification of human ccn2 (connective tissue growth factor) promoter polymorphisms." Journal Clin. Pathol: Mol. Pathol, 2001, vol. 54, pp. 192-196.
Boursier J., "Reproducibility of liver stiffness measurement by ultrasonographic elastometry" Clin Gastroenterol Hepatol. Aug. 30, 2008, vol. 6, Issue No. 11, pp. 1263-1269.
Brigstock, D. R., "Regulation of angiogenesis and endothelial cell function by connective tissue growth factor (CTGF) and cysteinerich 61 (CYR61)", Angiogenesis, 2002, vol. 5, p. 153.
Bruck R., "Analysis of ArgGlyAsp mimetics and soluble receptor of tumour necrosis factor as therapeutic modalities for concanavalin A induced hepatitis in mice" GUT, 1997, vol. 40, p. 133-138.
Croci et al., "Inhibition of connective tissue growth factor (CTGF/CCN2) expression decreases the survival and myogenic differentiation of human rhabdomyosarcoma cells", Cancer Research, 2004, vol. 64, pp. 1730-1736.
Czaja et al., "Diagnosis and Treatment of Autoimmune hepatitis" Hepatology 2002, vol. 36, No. 2, pp. 473-496.
Davila, "New genetic associations detected in a host response study to hepatitis B vaccine", Genes and Immunity, Apr. 1, 2010, vol. 11, No. 3, pp. 232-238.
Dessein et al., "Severe hepatic fibrosis in Schistosoma mansoni infection is controlled by a major locus that is closely linked to the interferongamma receptor gene" American Journal of Human Genetics, Sep. 1, 1999, vol. 65, No. 3, pp. 709-721.
Dessein "IFNgamma polymorphisms (IFNgamma +2109 and IFNgamma +3810) are associated with severe hepatic fibrosis in human hepatic schistosomiasis (Schistosoma mansoni)" Journal of Immunology, 2003, vol. 171, pp. 5596-5601.
Dessein et al., "Variants of CTGF are associated with hepatic fibrosis in Chinese, Sudanese, and Brazilians infected with Schistosomes" Journal of Experimental Medicine, Oct. 2009, vol. 206, No. 11, pp. 2321-2328.
ss116721864 dbSNP (www.ncbi.nlm.nih.gov/projects/SNP/snp_ss.cgi?subsnp_id=116721864submitted Jan. 17, 2009).

"EASL Clinical Practice Guideline: Managemetn of hepatitis C virus infection" J. Hepatol. 2011; vol. 55, pp. 245-264.
Fitzner, B., "Inhibitory effects of interferongamma on activation of rat pancreatic stellate cells are mediated by STAT1 and involve down regulation of CTGF expression" CELL Signal, 2007, vol. 19, pp. 782-790.
Fonseca "A polymorphism in the CTGF promoter region associated with systemic sclerosis." The New England Journal of Medicine, Sep. 20, 2007, vol. 357, No. 12, pp. 1210-1220.
Fried "Side effects of therapy of Hepatitis C and their management" Hepatology, Nov. 2002, vol. 36, No. 5, 2002, pp. S237-S244.
Gao, R., "Connective tissue growth factor induces cfos gene activation and cell proliferation through p44/42 MAP kinase in primary rat hepatic stellate cells" J HEPATOL, 2004, vol. 40, pp. 431-438.
Garciatsao G. "Outpatient liver biopsy: how safe is it?" Annals of Intern Medicine, Jan. 15, 1993vol. 118, pp. 150-153.
George, J., "siRNA-mediated knockdown of connective tissue growth factor prevents N-nitrosodimethylamine-induced hepatic fibrosis in rats" Gene Therapy, 2007, vol. 14, pp. 790-803.
Gourh, P., "CTGF polymorphism associated with systemic sclerosis" The New England Journal of Medicine, Jan. 17, 2008, vol. 358, 2008, pp. 308-309.
Gressner AM., "The cell biology of liver fibrogenesis—an imbalance of proliferation, growth arrest and apoptosis of myofibroblasts" CELL Tissue RES 1998, vol. 292, p. 447.
Gressner et al., "Connective tissue growth factor: a fibrogenic master switch in fibrotic liver diseases" Liver International, Sep. 2008, vol. 28, No. 8, pp. 1065-1079.
Gressner "Differential effects of TGFbeta on connective tissue growth factor (CTGF/CCN2) expression in hepatic stellate cells and hepatocytes" J. HEPATOL 2007, vol. 47, p. 699.
Henri, S., "Cytokine regulation of periportal fibrosis in humans infected with Schistosoma mansoni: IFNgamma is associated with protection against fibrosis and TNFalpha with aggravation of disease" J IMMUNOL 2002, vol. 169, p. 929.
Hirschhorn "A Comprehensive review of genetic association studies", Genetics in Medicine, Mar. 2002, vol. 4, No. 2, pp. 45-61.
Hilgenfeld et al., "From SARS to MERS: 10 years of research on highly pathogenic human coronaviruses", Antiviral Research, 2013, vol. 100, pp. 286-295.
Hora et al., "Connective tissue growth factor, steatosis and fibrosis in patients with chronic hepatitis C" Liver International 2008, vol. 28, pp. 370-376.
Ioannidis, John P.A., et al., "Replication validity of genetic association studies", Nature Genetics, Nov. 2001, vol. 29, pp. 306-309.
Ivkovic et al., "Connective tissue growth factor coordinates chondrogenesis and angiogenesis during skeletal development." Development 2003, vol. 130, p. 2779.
Jonsson et al., "Angiotensin-converting enzyme inhibition attenuates the progression of rat hepatic fibrosis" Gastroenterology 2001, vol. 121, p. 148.
Juppner, H. "Functional Properties of the PTH/PTHrP Receptor", Bone 1995, vol. 17 No. 2 Supplement 39S-42S.
Kalluri et al., "Epithelialmesenchymal transition and its implications for fibrosis" J Clin Invest, 2003, vol. 112, p. 1776.
King et al., "World Health Organization. Measuring morbidity in schistosomiasis mansoni: relationship between image pattern, portal vein diameter and portal branch thickness in largescale surveys using new WHO coding guidelines for ultrasound in schistosomiasis" TROP MED INT Health., Feb. 2003, vol. 8, No. 2, pp. 109-117.
Kobayashi et al., "Connective tissue growth factor and progressive fibrosis in biliary atresia" PEDIATR SURG INT, 2005, vol. 21, p. 12.
Kovalenko et al., "Validation of connective tissue growth factor (CTGF/CCN2) and its gene polymorphisms as noninvasive biomarkers for the assessment of liver fibrosis", Journal of Viral Hepatitis, 2009, vol. 16, pp. 612-620.
Lambertucci et al., "Magnetic resonance imaging and ultrasound in hepatosplenic schistosomiasis mansoni", REV SOC BRAS MED TROP., Aug. 2004, vol. 37, No. 4, pp. 333-337.
Leask et al., "All in the CCN family: essential matricellular signaling modulators emerge from the bunker" J. CELL SCI, 2006, vol. 119, p. 4803.

(56) References Cited

OTHER PUBLICATIONS

Leask et al., "The role of connective tissue growth factor, a multifunctional matricellular protein, in fibroblast biology" BIOCHEM CELL BIOL., 2003, vol. 81, p. 355.
Li et al "Inhibition of connective tissue growth factor by siRNA prevents liver fibrosis in rats." J. GENE MED., 2006, vol. 8, p. 889.
Li et al., "Adjusting multiple testing in multilocus analyses using the eigenvalues of a correlation matrix." Heredity, 2005, vol. 95, p. 221.
Macias et al., "Application of transient elastometry to differentiate mild from moderate to severe liver fibrosis in HIV/HCV coinfected patients" Journal of Hepatology, Oct. 2008, vol. 49, No. 6, pp. 916-922.
Mangia et al., "An IL28B Polymorphism Determines Treatment Response of Hepatitis C Virus Genotype 2 or 3 Patients Who Do Not Achieve a Rapid Virologic Response", Gastroenterology, Sep. 2010, vol. 139, No. 3, pp. 821-827.e1.
May et al, "How Many Species are there on Earth" Science, Sep. 16, 1988, vol. 241, pp. 1441-1449.
Mbeccel et al., "Interleukins, from 1 to 37, and interferon-: Receptors, functions, and roles in diseases", Journal of Allergy and Clinical Immunology, Nov. 2010, vol. 127, No. 3, pp. 701-721.e70.
Mohamedali et al., "Susceptibility to periportal (Symmers) fibrosis in human schistosoma mansoni infections: evidence that intensity and duration of infection, gender, and inherited factors are critical in disease progression" Journal of Infectious Diseases, Oct. 1999, vol. 180, No. 4, pp. 1298-12306.
Morita et al., "CTGF polymorphism associated with systemic sclerosis" New England Journal of Medicine, 2008, vol. 358, p. 308.
Mummindi et al., "Evolution of Human and Non-human Primate CC Chemokine Receptor 5 Gene and mRNA", Journal of Biological Chemistry, Jun. 2000, vol. 275, No. 25 pp. 18946-18961.
Nathan et al., "Musings and genome medicine: Hepatitis C" Genome Medicine, 2010, vol. 2, p. 4.
Neilson "Setting a trap for tissue fibrosis" NAT MED., 2005, vol. 11, p. 373.
Nyholt, D. R.: "A simple correction for multiple testing for singlenucleotide polymorphisms in linkage disequilibrium with each other" AM J HUM GENET., 2004, vol. 74, p. 765.
Oestereich et al., "Successful Treatment of advanced Ebola virus infectin with T-705 (favipiravir) in a small animal model", Antiviral Research, 2014, vol. 105, pp. 17-21.
Parkes et al., "Performance of serum marker panels for liver fibrosis in hepatitis C" J HEPATOL, 2006, vol. 44, pp. 462-474.
PCT/EP2010/052048_IPRP_AND_WRITTENOPINION_ dated Aug. 23, 2011.
PCT/EP2010/052048 International Search Report dated May 27, 2010.
PCT/EP2011/057145_IPRPandWrittenOpinioon_ dated Nov. 6, 2012.
PCT/EP2011/057145_ISR_ dated Jun. 27, 2011.
PCT/EP2012/065222_IPRP_ dated Feb. 11, 2014.
PCT/EP2012/065222_ISR_ dated Sep. 14, 2012.
Phillips et al, "Liposome-Antigen-Nucleic Acid Complexes Protect Mice from Lethal Challenge with Western and Eastern Equine Encephalitis Viruses", Journal of Virology, 2014, vol. 88, pp. 1771-1780.
Posada et al., "Simple (Wrong) Models for Complex Trees: A Case from Retroviridae", Mol. Biol. Evol., 2001, vol. 18, pp. 271-275.
Poupon et al., "Combined analysis of randomized controlled trials of ursodeoxycholic acid in primary biliary cirrhosis" Gastroenterology, 1997, vol. 113, p. 884.
Poynard et al., "Randomised trial of interferon alpha2b plus ribavirin for 48 weeks or for 24 weeks versus interferon alpha2b plus placebo for 48 weeks for treatment of chronic infection with hepatitis C virus. International Hepatitis Interventional Therapy Group (IHIT)" LANCET, 1998, vol. 352, p. 1426.
Rachfal, A. W.; D. R. Brigstock.: "Connective tissue growth factor (CTGF/CCN2) in hepatic fibrosis" HEPTATOL RES vol. 26, 2003, p. 1.
Richter et al., "Report of the second satellite symposium on ultrasound in schistosomiasis" MEM INSTO OSWALDO CRUZ., 2001, vol. 96, pp. 151-156.
RS9102373 (RS9102373 NCBI website entry ss 12914243 Oct. 21, 2003).
Sa-Nguanmoo et al., "Analysis of connective tissue growth factor promoter polymorphism in Thai children with biliary atresia" Journal of the Medical Association of Thailand, Feb. 1, 2007, vol. 90, No. 2, pp. 251-257.
Schuppan et al., "Hepatitis C and liver fibrosis", Cell Death and Differentiation, Nature, Jan. 1, 2003, vol. 10, No. Supplement 1, pp. S59-S67.
Sebastiani et al., "Stepwise combination algorithms of noninvasive markers to diagnose significant fibrosis in chronic hepatitis C." J HEPATOL, 2006, vol. 44, pp. 686-693.
Shimo et al., "Involvement of CTGF, a hypertrophic chondrocytespecific gene product, in tumor angiogenesis." Oncology, 2001, vol. 61, p. 315.
SS85338383 (NCBIdbsSNP Website RS9402373 Entry Dec. 6, 2007.
Syvanen, Ann-Christine, "Accessing Genetic Variation: Genotyping Single Nucleotide Polimorphisms", Nature, Dec. 2001, vol. 2, p. 930.
Testino et al., "Treatment of Recurrent Hepatitis C (Genotype 1) with Pegylated Interferon Alfa-2b and Ribavirin Combination and Maintenance Therapy", Hepatogastroenterology, Mar.-Apr. 2011, vol. 58, No. 106, pp. 536-538.
Tseng et al., "Prognostic Effect of Human Leukocyte Antigen Class I and II Alleles on Chronic Hepatitis C Patients Treated by Pegylated Interfeon-Alfa Plus Rivavirin in Taiwan", Hepato-Gastroenterology, May 1, 2010, vol. 57, No. 99-100, pp. 456-461.
U.S. Appl. No. 13/201,520 Non-Final Office Action dated Sep. 6, 2013.
U.S. Appl. No. 13/695,854 Non-Final Office Action dated Dec. 4, 2013.
U.S. Appl. No. 13/201,520 Final Office Action dated Mar. 20, 2014.
U.S. Appl. No. 13/695,854 Final Office Action dated Jun. 24, 2014.
Wahab, et al., "Modulation of the TGFbeta/Smad signaling pathway in mesangial cells by CTGF/CCN2." EXP CELL RES, 2005, vol. 307, p. 305.
Yoshida et al., "Connective tissue growth factor binds to fibronectin through the type I repeat modules and enhances the affinity of fibronectin to fibrin." BIOCHIM BIOPHYS ACTA, 2007, vol. 1770, p. 672.
Ziol et al., "Noninvasive assessment of liver fibrosis by measurement of stiffness in patients with chronic hepatitis C." Hepatology, 2005, vol. 41, pp. 48-54.
Hennig et al., Influence of IL-10RA and IL-22 polymorphisms on outcome of hepatitis C virus infection. Liver International, 1134-1143, 2007.
U.S. Appl. No. 13/695,854 Office Action dated Jun. 22, 2016.
U.S. Appl. No. 15/045,107 Restriction Requirement dated Aug. 1, 2016.
Sertorio et al., IL-22 and IL-22 binding protein (IL-22BP) regulate fibrosis and cirrhosis in Hepatitis C virus and Schistosome infections. Hepatology, 61:1321-1331, 2015.

* cited by examiner

SEQUENCE LISTING

<160> NUMBER OF SEQ ID NOS: 39

<210> SEQ ID NO 1
<211> LENGTH: 4000
<212> TYPE: DNA
<213> ORGANISM: Homo sapiens
<220> FEATURE:
<221> NAME/KEY: allele
<222> LOCATION: (2000)..(2000)
<223> OTHER INFORMATION: y = c or t

<400> SEQUENCE: 1

| | | | | | | |
|---|---|---|---|---|---|---|
| acatgacaag | gccagagaaa | acagaaaggc | agaaagagaa | gccaaaagag | ctgcaatgac | 60 |
| agcgataact | aagaaggaag | aggaaaccct | taccatgccc | ttattggagc | ttcctcttac | 120 |
| agaacccct | aactactcct | ctaatgaaaa | ggcttggttt | gagcaggaaa | gtggaagtta | 180 |
| ccagaaagga | agttggtgga | agttctcaaa | tgggaggctc | gccagctatc | ccagaagcaa | 240 |
| tagcccctgg | ttcataaaac | agtttcatca | aggaacacat | atgggaaaaa | ctgcattaga | 300 |
| gactcttgta | ggatggcatt | tctattgctg | agcctaactg | ccatcactcg | agccatttat | 360 |
| gagtaatgtt | taacttgtgc | cccaaacaat | ccacagcagg | ggccaacatg | gccccaggg | 420 |
| attcaagaaa | ctggagctac | accctgtgaa | aacctgcatg | tgggctttac | tgagctgcct | 480 |
| cgaaccggag | gctaccggtg | catgctagtg | tttgtctgca | ctttctcagg | gtgggttgag | 540 |
| gcatttccca | ccaggacaaa | gaaagctcgg | gaagtaacca | gaatcttact | aaaggacatt | 600 |
| attcctagat | ttcgactgcc | tctaacttta | ggatcagaca | atggcccagc | atttgtggca | 660 |
| gaaatagtac | aacagctaac | acagaggtta | aaaatcaaat | gaaaactgca | tacagcttat | 720 |
| cacccataga | gttctggaaa | gttgaaagaa | taaaccggac | actcaaacag | ccgttaaaaa | 780 |
| agttttgcca | tgaaactcat | ctaagatggg | atcaggtgct | gcccatggtc | cttctctgag | 840 |
| tcaggtgcac | ccctactaaa | ttaactgggt | attcaccta | taagatagtg | tttggccgac | 900 |
| accctgatca | taactcagat | aaacggggat | ttaaaaaatt | ggggaattaa | ccttaagaag | 960 |
| gcaaatgcaa | gccttaggtg | aggtctcgca | ggaaatgcaa | ggatgggtaa | gagaaagaat | 1020 |
| acctgttagc | ctcacagatg | cagtacaacc | cttctaacct | ggagactctg | tctgggtcaa | 1080 |
| acaatggaac | ccaaccactt | tagggccttt | atgggatagt | ccccatattg | tgatcttgtc | 1140 |
| tactcccact | gctgttaaag | ttgcaggtat | cataccttgg | gttcatcata | gccggctgaa | 1200 |
| accagaagca | gccaccaccc | aggaccagtg | gacaagtcaa | caaacccag | accactcaac | 1260 |
| atggctgatc | ctgtggtgaa | accaagccac | tgctgacaag | gacaactgcc | ctgcttcaac | 1320 |
| cacaccagag | gctggttggt | ccacgcacgg | ctgaagcttg | aggaaacatc | gagccctgtt | 1380 |
| ctagtcacac | aaatggaagc | tgactagtct | atgcatggct | gaagcctgag | gaagtcaatg | 1440 |
| atacataagt | aaatgtagac | taaatttaca | aacatagtta | tactcttact | tgtagtaatt | 1500 |
| attttgctgt | catgttatct | ttgcaaatgc | tgccaagctt | gttgcccaga | aaggtgccca | 1560 |
| tgcatagtat | aagtttaatc | atattagtaa | tactgaagcc | actgacactt | tcacctatgg | 1620 |
| ttataaaagg | ggaccaggat | gactgtcatc | actgtatgat | agaagcctgg | tctggaaaag | 1680 |
| gtgtgactaa | aactctgtta | taccagacct | actatgagtg | tacagggact | catacaggaa | 1740 |
| cttgttgttt | ataaccagac | taattactca | gtctgtgatc | ctggaaacgg | gcagcccaa | 1800 |
| atatgttatg | acccagagtt | cttgccctat | gacttcttat | ttgaagtcca | aatttggtga | 1860 |
| accccctaatg | ccatcatata | caaacccac | agaaactggg | gtcagtaaac | ttgtaaacaa | 1920 |
| aacgcaagta | ttcacttacg | cgcataaagg | gcccgtctcc | atatattttg | atgcctgcca | 1980 |

```
agctgcacat ctcagtaaay taaataatat ttggaccatc tgtaaaaatc taggacaaga    2040
aagagtcagc agcagagcca ccaaggccat aataggagag tccgaaaaag agtgccctga    2100
ttgtgataat cagtggacca cacatgaatt taatcagcac ctatacactg aagggctgc     2160 tctgtttgcc agccaagagg agaagatagg gtacacaact ggaacatgct acccactcaa    2220
tctgacaata ctaaagccaa atatgacttt ctggactaaa gggcataaag gattactaac    2280 cttgatcag gcaggagctc tcctaggact tggtattcct ctggtcatca caagaaaac     2340 ccaaaggact caagttcaac ttagcccaat acaacagttc aggttttata atctttcaa     2400 tgaacacttt aattctgaag tatcaaaaat tcaaattcct cctatatcaa ctgaaaatct    2460
gtttgtccag ctagccaaaa gtattgctaa caatttagga gttacttcct gttatgtatg    2520
tggaggtgct aatatgagag atcaatggcc ctgggaagcc agagaattga tgctgcaaga    2580
caattttacc ttgcctgaat tgttacaaa attcaatgca aatccaagtg tttggctatt     2640
aaggaacccc atcattggaa aatactgtat tgcctgttgg ggcaagtcct ttcagaacca    2700 gatagggaa acaacttgcc taggtcaaca atattttgaa gaatctgaga acagaacaca    2760
atggagaagc tttatagatg attcctctgt gtcactttaa tcccttttg cagttcccaa     2820 cactaaatca atcatggtac caattagaag ctccaactgt ttggagagca cctgcaggat    2880
tatataggat ctgtggaaca aaggcttatc aattactaac cgataaatgg acaggggcat    2940
gtatattagg aacaataagg ccattctttt tgctactccc cctgcagcaa ggggaagatc    3000
taagctatct ggtctatgat gaaggcagaa aaagagtcaa aagaaatgtg tttacaaaaa    3060
taagtactga ggaaaaaata aatactaaca ttaaaaagga cattgaaata ggggctgga    3120 aagataatga atggcccct gggcacaaga tgggtcatgg ggatactgta ctcctattta    3180
tatgttaaac cacatcataa ggttgcaagc agttctggaa attatagtca atgaaacagc    3240
ctgagcctta gacttgctag ccatacaggc aacccagatg agagatgcca tttatcagaa    3300
caggttagta ctgaattatg ttttagcttc agaaggggt ttgtggaaaa cttaatttaa     3360
caaattgctg cttacaaatt gatgacaatg gaaaagctgt catggaaatc actgccagga    3420
tgcggaagtt agctcatgtt ctggttcaga catggtctgg ttgaacccg agttcactct     3480 ttggaggacg gttttcatgg tttggaggct ttaaaactgt aatactaggc tttgtggcca    3540
taaaaggtgg atgcctactg cttccctgtc tcttgccatt tctaatcgga agcatccaat    3600
ccaccataga ctcaatggta gacagacata ccaccatccg aataaaggct ctgcaaaagt    3660
accaactggt atcccaagat gagtatgtac ccactcaaga agaaatagct aactgtggtg    3720
ctctttatta atctacattt gtgtcgagca ccaaaagggg gaaatgaaga aggaattaat    3780
gaaatcaact ataacctaag agtagtagta atacaaattt taaaatcctt ttaaagttcc    3840
tgcaaaatgt gaccctgcc ttacattcac gttaaaggg aatattaaca gcctgtcttc      3900
tctctgtgga cagtggacct tatctatact ccccaactcc acattcctca aagtttatta    3960
caggcccagt gagttcctgc atgactgcag ggtcacaaga                           4000
```

<210> SEQ ID NO 2
<211> LENGTH: 1001
<212> TYPE: DNA
<213> ORGANISM: Homo sapiens
<220> FEATURE:
<221> NAME/KEY: allele
<222> LOCATION: (501)..(501)
<223> OTHER INFORMATION: r = a or g

<400> SEQUENCE: 2

```
taactgttga aatttgggtgt caggtttatt atactctact tttgtatgta cttaaaattg      60
ttcataacaa agaaaaaaga tttttaaagt ttatctacaa gatgtggcca gacacggtgg     120
ctcacacctg taatctcagc actttggaag gcggaggtgg gtggatcatt tgaggtgtgg     180
agttccagac cagcctggcc aacatggtgc aacccgtct gtactaaaaa tacaaaaatt     240
agccaggcgt gacggtgtgt gcctgtaatc ccagctactc agtggggctg aggcaggaga     300
attgcttgag tcaaggaggt gaggtttgca gtgagccgag atcgcgccac tgcgctccag     360
tctgggcagc gataaagcga gagtccatct caaaaaaata aataaataaa taaataaagt     420
ttacttacca gatgctgtct tccttttggt aatttaatg ccatttagt gtcaataata      480
agatctaata attatgggac rccatgttat gttttccca tattttgtct ttgttaatcc      540
tcttatgaag tctaggagat tggtattatt attcatttga tgttacagat gaagaaactg     600
agacatagat agagaggtgg agagaacttg accagggctc tatagcgagt agtggtaaag     660
tgagggctga aatcagatct ggttagcctc agggcctgag gagtattatg aaactcctct     720
tgtgttattc tttgcttgta atagacattc cataaaggga tagaatgatg tcaaagaaca     780
tttgtccatt ggcttctcga atcgtttatt cagtcaaaca aatgtttatt gagcaactgt     840
tatatgccag gcactgtgtt agacatcggg gatgcagaaa tgaacaagac tacagagcca     900
gccctcaggg aaccaacagc attttcttca accaggtctt ggtagcaaag ggctaagtgt     960
ttcttattgt ttttcagaga agtgtttaaa aactggtgtt c                        1001
```

<210> SEQ ID NO 3
<211> LENGTH: 818
<212> TYPE: DNA
<213> ORGANISM: Homo sapiens
<220> FEATURE:
<221> NAME/KEY: allele
<222> LOCATION: (501)..(501)
<223> OTHER INFORMATION: y = c or t

<400> SEQUENCE: 3

```
ccatgggaag gattccaacc ttcttccaca tccatgttcc ttgcttagcc caacaagacc      60
ctggcagagg ctcctgccca agggccatgc tgggccttgg gctcccctct cggcccttag     120
ctggctcctt gtcctctgag ctgcacttgt tccagcctga ggcatcccte cctcccaccc     180
ttcatccaca agaccccagc yctgcctcct caatgtttta tttgcattct gagttcctac     240
tatattgtat tcccaagaca tatctcttct aaatttctaa attacagtaa aacaacttct     300
aaatttcatg tgtgatatgg tttggctgtg tccccaccaa aatcttgtct tgcattgtag     360
cttccataat cccatatat tgtgggaggg acctggtggg aggtaaatga atcatgggg      420
tgttttttc ccatgctgtt ctcatgatag tgaataagtc ttacaagatc tgatgatttt     480
ataagggca gttcccctgc acacatctct tgcctgccac catgtaagac gtgcctttgc     540
ttctcctcct tctgccatga ttgtgaggcc tacccagtca tggggaactg ttaatccatt     600
aaacctcttt ttatttataa attacccagt cttgggtatg tctttattag aagtgtgaga     660
aaggactaat acactgtgcc tcagttcct cactggaaaa aaatgtataa tactagtctt      720
accagatagc taggagtgtc aataagagaa actttgccaa ccatctgcct atagtagagg     780
ctcaggcgca ttagttctcc ctcccatttc tttccact                             818
```

<210> SEQ ID NO 4
<211> LENGTH: 7142

```
<212> TYPE: DNA
<213> ORGANISM: Homo sapiens
<220> FEATURE:
<221> NAME/KEY: allele
<222> LOCATION: (1706)..(1706)
<223> OTHER INFORMATION: k = g or t

<400> SEQUENCE: 4
tgagcagggg gcacagcaaa gccccaaggc tgaggccaga tgaaggagca ggaggcaatg      60
tggctggaga ggagggagca aggggcagag tgttggtggt gaggtcaggg gcccagcagc     120
ctgatccagg ggacttgaac aggatggaag gactttgggt gcgttctgaa gaagggaag     180
ccactggaag gcattaagta gaaaaaattg gaagtgagag taattatatg tgaaagttgt     240
tagagtcaca atggagtgac gatgaggcag acaggtagt caaggaagta agtgcagtta     300
acacaatgag ccccagtatt cgcattgtaa tccagctcat gcaagcacag ctatctcctg     360
cagggaatat ttcccataga cagcatttgc actttgattt tacctcttct caaacggacc     420
ctgttctcat gataatagta aaaacacac ccctaggtgg agatttaaga tgctgatgaa      480
ttatgagatg tatgaacaag catgtacagc tactgcacat gtgcacccag aggaccaccg     540
aggacatgct tactagcaac accttttctc accctcttat gaataatcat gtaagagtcc     600
cataaaagga tttctccagc aataatcagt gctgtccatt cagtggctca tgcctgtaac     660
ccagcacttt gggaggccga ggtgggtgga tcacctgagg tcaggagttt gagaccagcc     720
tggtcaacat ggtgaaacct cgtttctatt aaaaatacaa aaaagtagc caggtgtaat     780
ggcacatgcc tgtaatccca gctacttggg aggctgaagc aggagaactg attgaacctg     840
ggaggtggag gttgcagtga gtcatgactg tgccactgca ctccagccaa cagagtaaga     900
ctctgttccc cctcggcccc ctgcaaaaaa aataataac aatgataaga ggcaagatca      960
atggccacca aaattttatt ttttcccata gcgttgctgg ggtggcatgg ctgcctgccc    1020
tgggttcatc ctgtccctaa gtggaactcc ctatggctga gggactcaga atcaaatgac    1080
ttatagccaa ttaaatgttc tagtccagat gcccaattaa atgggcatgg acagacattc    1140
attagccttt aaattatttt ctaagtaaaa agtcaacaaa caaaaagtta aggtgaggt    1200
tacaaaactg acttttcttt aacttctatg ctactgtaat cttgggtttt gttatggact    1260
tatagcaatt atttatacaa aacataagaa ttgttctgaa aaaattaaaa aatatatacc    1320
tgcatggctc ataactggaa atattatacc aggaggcttt gtcacttggt atctttatcc    1380
ttttacttat tattttcttt taattctaca ggaagcagta aattctttat ggttggagtg    1440
gatgaagagg tgccatgtaa tagctcagaa ggcaaagtcc cttgttttac cagctgttta    1500
ggcatccatg tactcatcct tgatttgaag ggtttgagtt aattctatcc ttccaaatca    1560
gcccttacaa tctcacgtgc ccacctcttc tgcaacagtc tctgggccta gagggaggac    1620
gcttgcaata caggattttt tgcatgttcc cagtggctcc accccattct cccagtgcac    1680
atgcaggccc ttagtctgaa cccackctac attgatttat ttcccttact gagcatgtgt    1740
taagggatgg aattttcac catgggcatg tttaggcaag cccctgtac acaatgtcct     1800
ggatggcatt tggctgtctt ctgcctctat cattccccca tctaaaagag tacatctaac    1860
tgccattaga ataaggataa gaagaaagac aaagacccca cttaactgct ttctgctgac    1920
agagggcact gttttggaaa gacagcagtt gggtctccct cagaggccta tctaagggta    1980
tctggtaaaa gggaccatca ttcgaggctc tggttgcata actgtttgga gtttgagggc    2040
ctgaaggcga gaagagacaa accaggttat tagaagacat gtaccaaaat gaaatggggg    2100
```

```
aagggtaagg acagttcaaa aatcctgagg ctgctgacat gcccagataa ctggtagctg    2160
tagttgtgcc tgctaagatt tgggtgcatg ggacttggct ttggttagct cccgtagttt    2220
attttcccaa aaaagaaacc tctgggttat gggcacccta tttactccca ttatctggca    2280
ggatttgtag gataattgtt cagaactaga atactgttcc agattttt ac attacccatg    2340 ccttttgttt cttctgagct gcagccagag atcactggtt agttcacagg aataagcagg    2400
gttaatttaa aatgtaggca aaaaacttaa aaacaactaa tgagtctaga atttaatgac    2460
aaatgtatga taagttttga aacataattt ctttctcccc agtcctcatt tttgttaaaa    2520
acaaatcata ataggagtga gttgtttgta aaataaactt tagtcttaca cttggtctgc    2580
ttatttgcac aaagtacaac aagaataatt attttacat aggcttttta aattggcttt    2640
gatggaactc tgttccacaa ggaatttcag ataggacttc ataaaaatga gcccagccat    2700
gggtttgtac cctctaatac ctatgagttg ggtgaattgc tctcttcttg aggtcccaag    2760
aatatgcggt tcctggccct gttagaaagt gacattcttt actcactaca ggttagggaa    2820
cctgtatggg gactgtgtag acaaagtatg aggctggttt acccaagggg ctttt attgg    2880 ctctgcaagt tgagcttgat tccttaaagg gaaacatacc cttccagtca aagttacagt    2940
tactggttgg taaagttaaa gttacagcta ctggttgcta aagcaaccag tttctccaat    3000
tgcatcctgt tgcaaaagaa agtggattct tactgcactg atgcaaataa ccgtattgcc    3060
ctaagttaag aatactcaca gatagtttcc aaattctaga ggaagcaggc agagagaaaa    3120
aaaagtgcta aattttgttc ataggagtct gcattactca attattaaag attgtgtata    3180
gctcaaaaaa aaagatcagc actgttttaa gctaaagttt aaaaaagatt acttcaattt    3240
tctattagtt cagtctgttc agttaactct tgttctgctt gatatttgtg aacatttcag    3300
ctcttcatga gtcctgtacg ttttt ccatt attccaatgt cacaatctcc aaagttatca    3360
gaaacctgca tttgagagca cctgttacgt ttctatagct gattataaat cctatttgaa    3420
gaagatcaaa acaaaacaat ggtctgtgaa tagcaaaatg tccatggtag ttacagtcaa    3480
aaacacaatt gacaagaaa ttttgttatc tctgtggctt ataatcacct aacataacac    3540
ctttaattgt gagtgatagc atatacttag atattagaat tttagaaatc ccatacagtt    3600
ttggagcata tattattatt cactaaaata taacccaaag aagattaaat atcattttgg    3660
caatcccatg tacataaatt tgtcaggtaa tcctatttac ctctcttctg gatgctccag    3720
ggatgctagg ggtcaggaaa gacaaccttg aagctgacat ttgattttgg gaagcccatt    3780
aaatatgtta gaggtttaaa acaatgttat gaagtagaat tccagattac cataaattac    3840
ttattttgcc aaaatgatga ctcaaaaatt ttaaaacaag ccaaaaactt ttactcattt    3900
agagggaaga cttagatttc caagaatttt gtctcctgtc ttcactttca tttccttggc    3960
agtctatctg gaagacaaac tgaaatattt aattatcctt tactattaca tgaaaatctt    4020
atacaaggga gagaaagcca aattttaccc tcacattagt ttactattaa tgtcaacccc    4080
aattttttaa tgaaacctta tagacaattc tatccaatct taaccagttt gatcatgagg    4140
taagattcct gtaagccttt tataacccttt tacaaattac taatttacta atctgctaaa    4200
gagcagatta gggctttaag aaaaccttgt tgtgctttca tttcaatgct cagtttgtag    4260
aaaaaccata taatagagtt ttggatttaa tcaatgttca cacacagaat ttcttttgca    4320
agattaattt ttagaaacct cccacaactt gtttaaacct ttagtttatc ttatctaatt    4380
tataatagtc ctttaacctt aggcaaaaac ttacatttcc atgcattctt ataatctttg    4440
actaataaca cattttactg ttcttacata ccttgcatgt aaatctatt tcagtggtct    4500
```

```
caattacatg ttataatggt acctcttagc acttttttaat tttagtttaa aacctggtaa    4560
gtcgttttaa ttacgcacta ggtgctgata aagtttgatt ccttccagca taattaaggg    4620
tgtggttaat tccatatgtc cctgtgcctt accaagttgt aaagcaggca gattgaacag    4680
ttttcaaagg caaagaagc cgtttacaac cttaaaacat ttagccacct agtgcctgac     4740
ttgcataatt tagaccagct atttacattt taagaacatt tgcattttat caattatctt    4800
taagactact tttatttctc agagattaaa gtcacaagaa ctaaaaggca ttatagcttt    4860
tatctttcct ccaaaaatat ttgatcttag tgctgatttt tctttaagcc aattaattag    4920
agctcttttt tataactaca cagatggaga agaagattga gtgttataag atttttcatt    4980
tgcccatctc ctaattggat tcttggtctc tgggtgggac cctttaagag cagggctaag    5040
aaagcatgca gtttattttc ttttttttctt tttcttttct ttttttttga gaaagagttt   5100
cactcttgtt gcccaggctg gagtgcaatg gtgcgatctc agctcactgc aacctctgcc    5160
tcccaggttc aagcgattct cttacctcag cctcccaagt ggctgcatgc agtttctagg    5220
gcctaataaa caggcatagc tggaaaacaa aaacggattt tgagagcgat ctatttgcct    5280
ctaattcctg gggttccatg aggaaaacag aggtttctcc caaaatggaa tccatggtgc    5340
cttttctgtt tttaccaagc agccctatgc catcagaaat tatcttaggg cctctcatgt    5400
gcgcattaac actggcaaga caaggtggag aaaagtaatt cagtcaactg agaaaaaaat    5460 cttttttccag caaaacaaga tccaagaaga gaaaaacata aaggcctttc aaatatacgt    5520
atagcttgga tatccacttt taattaagct gagctctctt taagaaagtc cttttaaatc    5580
ccacattacc tgacttcagc catgccaagc agccaatatt tctggctttg aagtttatc    5640 aaaagaacct caaggttcaa ccaacaagcc tcaattaaga cacgcgaagc acaccagatt    5700
ggctacacct taagaccagc tcataaaac cttttcact aatggaaact ttacagggaa      5760
tatcaacagt gatccttatc attcttttca ccagtttaca cagggagaga gaggccaaaa    5820
gtctgactgg ttaaaaaact tttatcctttt tgctggcatg tcatgcttct gggttccctt   5880
cccctgagct caattctaag ccaaccagtt taaggtttgg gaaattaact tttctcagtt    5940
tggaggatgc atcctatggg aatgtccttt agtacaggga cacagtcacc catctgtgaa    6000
gagaggacaa aggaggaaaa agtaaaaaaa gattttttttc aaaggctccc caggggttca   6060
ggatgcattt gaaggggga cagattgaag atgaatggct actcatctag aaagagggga    6120
gccagacatc cctggttcct ttctcttttct aggaaatagc cagggtatgt gagggaaaga   6180
aggaacaagc atccattttc cttcttccgt ccttatgtcc ccaagtcctg acaacctcga    6240
cagggtgcca cccatgggtg ccaatacggt tctcacccat ggtaacaggg gacctagtgg    6300
atgggattat ccactgttac ccacaaactg tcttttccccc tgctctcaat agccttcaag   6360
tgccctagac ctcatttagg ccattgatac tagtatgacc tttatccatg aaacaagagg    6420
cttggcttaa ttgtcaggaa ttagtcatgc tcacctatac tgtgcttttt aattttttgtt   6480 gttgtctgcc tctggatccc tccgatgcag ttatctttcc tagggcttct acatgaagct    6540
tggaattgag tttgggacaa aagaactgcc tcagtaggtg ggtgcatgga ctcatcaatc    6600
cccaggtgtc cctcaccagt ctggctgctg ccgccttatc ataagctgaa ggctaaggtg    6660
caactgtgaa attaggtcct tctcaaacaa gggagggaaa atggtgtcct gtgaattagg    6720
gtcctggtct aataagatgc cttccaaaag gaagaaaact tctggcacag agaagacccc    6780
tctacccgca gggctgtgtt attaggttgg tgcgaaagca attgtggtgc ccatcattct    6840
```

```
aagtaatgac aaaaaccaca actactttca caccagccta ctaactcatg acttggtgga   6900
caaaagaaaa taacaacaac aacaacagct taaatgcagg gctgtgttta ctgctgacaa   6960
ggtggagaaa agaaaaatat gcctgagaaa tgcaaatgta tttctccaac aggcagagaa   7020
acttaattgc tattgcactg agctggaccc cttggcttgg ggtggggaag actctgtgga   7080
tacatggcag gggacactgg ccagttggct gcatggggcc caggcccctg agatcaccct   7140
gg                                                                  7142
```

<210> SEQ ID NO 5
<211> LENGTH: 7142
<212> TYPE: DNA
<213> ORGANISM: Homo sapiens
<220> FEATURE:
<221> NAME/KEY: allele
<222> LOCATION: (1807)..(1807)
<223> OTHER INFORMATION: r = a or g

<400> SEQUENCE: 5

```
gaaggagcag gaggcaatgt ggctggagag gagggagcaa gggcagagt gttggtggtg      60 aggtcagggg cccagcagcc tgatccaggg gacttgaaca ggatggaagg actttgggtg    120
cgttctgaag aaggggaagc cactggaagg cattaagtag aaaaaattgg aagtgagagt    180
aattatatgt gaaagttgtt agagtcacaa tggagtgacg atgaggcagg acaggtagtc    240
aaggaagtaa gtgcagttaa cacaatgagc cccagtattc gcattgtaat ccagctcatg    300
caagcacagc tatctcctgc agggaatatt tcccatagac agcatttgca ctttgatttt    360
acctcttctc aaacggaccc tgttctcatg ataatagtaa aaaacacacc ctaggtgga    420 gatttaagat gctgatgaat tatgagatgt atgaacaagc atgtacagct actgcacatg    480
tgcacccaga ggaccaccga ggacatgctt actagcaaca ccttttctca ccctcttatg    540
aataatcatg taagagtccc ataaaaggat ttctccagca ataatcagtg ctgtccattc    600
agtggctcat gcctgtaacc cagcactttg ggaggccgag gtgggtggat cacctgaggt    660
caggagtttg agaccagcct ggtcaacatg gtgaaacctc gtttctatta aaaatacaaa    720
aaaagtagcc aggtgtaatg gcacatgcct gtaatcccag ctacttggga ggctgaagca    780
ggagaactga ttgaacctgg gaggtggagg ttgcagtgag tcatgactgt gccactgcac    840
tccagccaac agagtaagac tctgttcccc ctcggccccc tgcaaaaaaa aataataaca    900
atgataagag gcaagatcaa tggccaccaa aattttattt tttcccatag cgttgctggg    960
gtggcatggc tgcctgccct gggttcatcc tgtcccctaag tggaactccc tatggctgag   1020
ggactcagaa tcaaatgact tatagccaat taaatgttct agtccagatg cccaattaaa   1080
tgggcatgga cagacattca ttagccttta aattattttc taagtaaaaa gtcaacaaac   1140
aaaaagttaa aggtgaggtt acaaaactga cttttcttta acttctatgc tactgtaatc   1200
ttgggttttg ttatggactt atagcaatta tttatacaaa acataagaat tgttctgaaa   1260
aaattaaaaa atatatacct gcatggctca taactggaaa tattataccc ggaggctttg   1320
tcacttggta tctttatcct tttacttatt attttctttt aattctacag gaagcagtaa   1380 attcttatg gttggagtgg atgaagaggt gccatgtaat agctcagaag gcaaagtccc   1440
ttgttttacc agctgtttag gcatccatgt actcatcctt gatttgaagg gtttgagtta   1500
attctatcct tccaaatcag cccttacaat ctcacgtgcc cacctcttct gcaacagtct   1560
ctgggcctag agggaggacg cttgcaatac aggatttttt gcatgttccc agtggctcca   1620 cccccattctc ccagtgcaca tgcaggccct tagtctgaac ccacgctaca ttgatttatt   1680
```

```
tcccttactg agcatgtgtt aagggatgga attttttcacc atgggcatgt ttaggcaagc    1740
cccctgtaca caatgtcctg gatggcattt ggctgtcttc tgcctctatc attcccccat    1800
ctaaaaragt acatctaact gccattagaa taaggataag aagaaagaca aagacccatc    1860
ttaactgctt tctgctgaca gagggcactg ttttggaaag acagcagttg ggtctccctc    1920
agaggcctat ctaagggtat ctggtaaaag ggaccatcat tcgaggctct ggttgcataa    1980
ctgtttggag tttgagggcc tgaaggcgag aagagacaaa ccaggttatt agaagacatg    2040
taccaaaatg aaatggggga agggtaagga cagttcaaaa atcctgaggc tgctgacatg    2100
cccagataac tggtagctgt agttgtgcct gctaagattt gggtgcatgg gacttggctt    2160
tggttagctc ccgtagttta ttttcccaaa aaagaaacct ctgggttatg gcaccctat    2220 ttactcccat tatctggcag gatttgtagg ataattgttc agaactagaa tactgttcca    2280 gattttttaca ttacccatgc cttttgtttc ttctgagctg cagccagaga tcactggtta    2340
gttcacagga ataagcaggg ttaatttaaa atgtaggcaa aaaacttaaa aacaactaat    2400
gagtctagaa tttaatgaca aatgtatgat aagttttgaa acataatttc tttctcccca    2460
gtcctcattt ttgttaaaaa caaatcataa taggagtgag ttgttttgtaa aataaactttt    2520 agtcttacac ttggtctgct tatttgcaca aagtacaaca agaataatta tttttacata    2580 ggcttttttaa attggctttg atggaactct gttccacaag gaatttcaga taggacttca    2640
taaaaatgag cccagccatg ggtttgtacc ctctaatacc tatgagttgg gtgaattgct    2700
ctcttcttga ggtcccaaga atatgcggtt cctggccctg ttagaaagtg acattcttta    2760
ctcactacag gttagggaac ctgtatgggg actgtgtaga caaagtatga ggctggttta    2820
cccaaggggc ttttattggc tctgcaagtt gagcttgatt ccttaaaggg aaacataccc    2880
ttccagtcaa agttacagtt actggttggt aaagttaaag ttacagctac tggttgctaa    2940
agcaaccagt ttctccaatt gcatcctgtt gcaaaagaaa gtggattctt actgcactga    3000
tgcaaataac cgtattgccc taagttaaga atactcacag atagtttcca aattctagag    3060
gaagcaggca gagagaaaaa aaagtgctaa attttgttca taggagtctg cattactcaa    3120
ttattaaaga ttgtgtatag ctcaaaaaaa aagatcagca ctgttttaag ctaaagttta    3180
aaaaagatta cttcaatttt ctattagttc agtctgttca gttaactctt gttctgcttg    3240
atatttgtga acatttcagc tcttcatgag tcctgtacgt ttttccatta ttccaatgtc    3300
acaatctcca aagttatcag aaacctgcat ttgagagcac ctgttacgtt tctatagctg    3360
attataaatc ctatttgaag aagatcaaaa caaaacaatg gtctgtgaat agcaaaatgt    3420
ccatggtagt tacagtcaaa aacacaattg acaagaaat tttgttatct ctgtggctta    3480
taatcaccta acataacacc tttaattgtg agtgatagca tatacttaga tattagaatt    3540
ttagaaatcc catacagttt tggagcatat attattattc actaaaatat aacccaaaga    3600
agattaaata tcattttggc aatcccatgt acataaattt gtcaggtaat cctatttacc    3660
tctcttctgg atgctccagg gatgctaggg gtcaggaaag acaaccttga agctgacatt    3720 tgatttggg aagcccatta aatatgttag aggtttaaaa caatgttatg aagtagaatt    3780
ccagattacc ataaaattact tattttgcca aaatgatgac tcaaaatttt taaaacaagc    3840
caaaaacttt tactcatttta gagggaagac ttagatttcc aaagaatttg tctcctgtct    3900
tcactttcat ttccttggca gtctatctgg aagacaaact gaaatattta attatccttt    3960
actattacat gaaaatctta tacaagggag agaaagccaa attttaccct cacattagtt    4020
```

```
tactattaat gtcaacccca attttttaat gaaaccttat agacaattct atccaatctt    4080
aaccagtttg atcatgaggt aagattcctg taagccttt  ataaccttt  acaaattact    4140 aatttactaa tctgctaaag agcagattag ggctttaaga aaaccttgtt gtgctttcat    4200
ttcaatgctc agtttgtaga aaaccatat  aatagagttt tggatttaat caatgttcac    4260
acacagaatt tcttttgcaa gattaatttt tagaaacctc ccacaacttg tttaaacctt    4320
tagtttatct tatctaattt ataatagtcc tttaaccttta ggcaaaaact tacatttcca   4380
tgcattctta taatctttga ctaataacac attttactgt tcttacatac cttgcatgta    4440
aatctatttt cagtggtctc aattacatgt tataatggta cctcttagca cttttttaatt   4500 ttagttttaaa acctggtaag tcgttttaat tacgcactag gtgctgataa agtttgattc    4560
cttccagcat aattaagggt gtggttaatt ccatatgtcc ctgtgcctta ccaagttgta    4620
aagcaggcag attgaacagt tttcaaaggc aaaagaagcc gtttacaacc ttaaaacatt    4680
tagccaccta gtgcctgact tgcataattt agaccagcta tttacatttt aagaacattt    4740
gcattttatc aattatcttt aagactactt ttatttctca gagattaaag tcacaagaac    4800
taaaaggcat tatagctttt atcttttcctc caaaaatatt tgatcttagt gctgattttt    4860
ctttaagcca attaattaga gctcttttt  ataactacac agatggagaa gaagattgag    4920
tgttataaga ttttttcattt gcccatctcc taattggatt cttggtctct gggtgggacc    4980
ctttaagagc agggctaaga aagcatgcag tttattttct ttttttcttt ttcttttcttt   5040 ttttttttgag aaagagtttc actcttgttg cccaggctgg agtgcaatgg tgcgatctca    5100
gctcactgca acctctgcct cccaggttca agcgattctc ttacctcagc ctcccaagtg    5160
gctgcatgca gtttctaggg cctaataaac aggcatagct ggaaaacaaa acggattttt    5220
gagagcgatc tatttgcctc taattcctgg ggttccatga ggaaaacaga ggtttctccc    5280
aaaatggaat ccatggtgcc ttttctgttt ttaccaagca gccctatgcc atcagaaatt    5340
atcttagggc ctctcatgtg cgcattaaca ctggcaagac aaggtggaga aaagtaattc    5400
agtcaactga gaaaaaaatc ttttttccagc aaaacaagat ccaagaagag aaaaacataa    5460 aggccttttca aatatacgta tagcttggat atccactttt aattaagctg agctctcttt    5520
aagaaagtcc tttttaaatcc cacattacct gacttcagcc atgccaagca gccaatattt    5580
ctggctttgg aagtttatca aaagaacctc aaggttcaac caacaagcct caattaagac    5640
acgcgaagca caccagattg gctacacctt aagaccagcc tcataaaacc ttttttcacta    5700 atggaaactt tacagggaat atcaacagtg atccttatca ttcttttcac cagtttacac    5760
agggagagag aggccaaaag tctgactggt taaaaaactt ttatcctttt gctggcatgt    5820
catgcttctg ggttcccttc ccctgagctc aattctaagc caaccagttt aaggtttggg    5880
aaattaactt ttctcagttt ggaggatgca tcctatggga atgtccttta gtacagggac    5940
acagtcaccc atctgtgaag agaggacaaa ggaggaaaaa gtaaaaaaag atttttttca    6000
aaggctcccc agggggttcag gatgcatttg aaaggggac  agattgaaga tgaatggcta    6060
ctcatctaga aagaggggag ccagacatcc ctggttcctt tctctttcta ggaaatagcc    6120
agggtatgtg agggaaagaa ggaacaagca tccattttcc ttcttccgtc cttatgtccc    6180
caagtcctga caacctcgac agggtgccac ccatgggtgc caatacggtt ctcacccatg    6240
gtaacagggg acctagtgga tgggattatc cactgttacc cacaaactgt ctttcccccct   6300 gctctcaata gccttcaagt gccctagacc tcatttaggc cattgatact agtatgacct    6360
ttatccatga aacaagaggc ttggcttaat tgtcaggaat tagtcatgct cacctatact    6420
```

-continued

```
gtgcttttta attttttgttg ttgtctgcct ctggatccct ccgatgcagt tatctttcct     6480
agggcttcta catgaagctt ggaattgagt ttgggacaaa agaactgcct cagtaggtgg     6540
gtgcatggac tcatcaatcc ccaggtgtcc ctcaccagtc tggctgctgc cgccttatca     6600
taagctgaag gctaaggtgc aactgtgaaa ttaggtcctt ctcaaacaag ggagggaaaa     6660
tggtgtcctg tgaattaggg tcctggtcta ataagatgcc ttccaaaagg aagaaaactt     6720
ctggcacaga gaagacccct ctacccgcag ggctgtgtta ttaggttggt gcgaaagcaa     6780
ttgtggtgcc catcattcta agtaatgaca aaaccacaa ctactttcac accagcctac      6840
taactcatga cttggtggac aaaagaaaat aacaacaaca acaacagctt aaatgcaggg     6900
ctgtgtttac tgctgacaag gtggagaaaa gaaaaatatg cctgagaaat gcaaatgtat     6960
ttctccaaca ggcagagaaa cttaattgct attgcactga gctggacccc ttggcttggg     7020
gtggggaaga ctctgtggat acatggcagg ggacactggc cagttggctg catggggccc     7080
aggcccctga gatcaccctg gggctggggc agcagctgtg gctcaatcct gcactggatg     7140
gc                                                                    7142

<210> SEQ ID NO 6
<211> LENGTH: 7142
<212> TYPE: DNA
<213> ORGANISM: Homo sapiens
<220> FEATURE:
<221> NAME/KEY: allele
<222> LOCATION: (3512)..(3512)
<223> OTHER INFORMATION: k = g or t

<400> SEQUENCE: 6
gaaggagcag gaggcaatgt ggctggagag gagggagcaa ggggcagagt gttggtggtg       60
aggtcagggg cccagcagcc tgatccaggg gacttgaaca ggatggaagg actttgggtg     120
cgttctgaag aaggggaagc cactggaagg cattaagtag aaaaaattgg aagtgagagt     180
aattatatgt gaaagttgtt agagtcacaa tggagtgacg atgaggcagg acaggtagtc     240
aaggaagtaa gtgcagttaa cacaatgagc cccagtattc gcattgtaat ccagctcatg     300
caagcacagc tatctcctgc agggaatatt tcccatagac agcatttgca ctttgatttt     360
acctcttctc aaacggaccc tgttctcatg ataatagtaa aaaacacacc cctaggtgga     420
gatttaagat gctgatgaat tatgagatgt atgaacaagc atgtacagct actgcacatg     480
tgcacccaga ggaccaccga ggacatgctt actagcaaca ccttttctca ccctcttatg     540
aataatcatg taagagtccc ataaaaggat ttctccagca ataatcagtg ctgtccattc     600
agtggctcat gcctgtaacc cagcactttg ggaggccgag gtgggtggat cacctgaggt     660
caggagtttg agaccagcct ggtcaacatg gtgaaacctc gtttctatta aaaatacaaa     720
aaaagtagcc aggtgtaatg gcacatgcct gtaatcccag ctacttggga ggctgaagca     780
ggagaactga ttgaacctgg gaggtggagg ttgcagtgag tcatgactgt gccactgcac     840
tccagccaac agagtaagac tctgttcccc ctcggccccc tgcaaaaaaa aataataaca     900
atgataagag gcaagatcaa tggccaccaa aatttatttt tttcccatag cgttgctggg     960
gtggcatggc tgcctgccct gggttcatcc tgtcccctaag tggaactccc tatggctgag    1020
ggactcagaa tcaaatgact tatagccaat taaatgttct agtccagatg cccaattaaa    1080
tgggcatgga cagacattca ttagccttta aattattttc taagtaaaaa gtcaacaaac    1140
aaaaagttaa aggtgaggtt acaaaactga cttttcttta acttctatgc tactgtaatc    1200
```

```
ttgggttttg ttatggactt atagcaatta tttatacaaa acataagaat tgttctgaaa   1260
aaattaaaaa atatatacct gcatggctca taactggaaa tattatacca ggaggctttg   1320
tcacttggta tctttatcct tttacttatt attttctttt aattctacag gaagcagtaa   1380 attcttatg gttggagtgg atgaagaggt gccatgtaat agctcagaag gcaaagtccc    1440
ttgttttacc agctgtttag gcatccatgt actcatcctt gatttgaagg gtttgagtta   1500
attctatcct tccaaatcag cccttacaat ctcacgtgcc cacctcttct gcaacagtct   1560
ctgggcctag agggaggacg cttgcaatac aggatttttt gcatgttccc agtggctcca   1620
ccccattctc ccagtgcaca tgcaggccct tagtctgaac ccacgctaca ttgatttatt   1680
tcccttactg agcatgtgtt aagggatgga attttttcacc atgggcatgt ttaggcaagc  1740
cccctgtaca caatgtcctg gatggcattt ggctgtcttc tgcctctatc attcccccat   1800
ctaaaagagt acatctaact gccattagaa taaggataag aagaaagaca aagacccatc   1860
ttaactgctt tctgctgaca gagggcactg ttttggaaag acagcagttg ggtctccctc   1920
agaggcctat ctaagggtat ctggtaaaag ggaccatcat tcgaggctct ggttgcataa   1980
ctgtttggag tttgagggcc tgaaggcgag aagagacaaa ccaggttatt agaagacatg   2040
taccaaaatg aaatgggga agggtaagga cagttcaaaa atcctgaggc tgctgacatg    2100
cccagataac tggtagctgt agttgtgcct gctaagattt gggtgcatgg gacttggctt   2160
tggttagctc ccgtagttta ttttcccaaa aagaaacct ctgggttatg ggcaccctat    2220
ttactcccat tatctggcag gatttgtagg ataattgttc agaactagaa tactgttcca   2280 gattttaca ttacccatgc cttttgtttc ttctgagctg cagccagaga tcactggtta    2340
gttcacagga ataagcaggg ttaatttaaa atgtaggcaa aaaacttaaa aacaactaat   2400
gagtctagaa tttaatgaca aatgtatgat aagttttgaa acataatttc tttctcccca   2460
gtcctcattt tgttaaaaaa caaatcataa taggagtgag ttgtttgtaa aataaacttt   2520
agtcttacac ttggtctgct tatttgcaca aagtacaaca agaataatta ttttacata    2580 ggcttttttaa attggctttg atggaactct gttccacaag gaatttcaga taggacttca   2640
taaaaatgag cccagccatg ggtttgtacc ctctaatacc tatgagttgg gtgaattgct   2700
ctcttcttga ggtcccaaga atatgcggtt cctggccctg ttagaaagtg acattcttta   2760
ctcactacag gttagggaac ctgtatgggg actgtgtaga caagtatga ggctggttta    2820 cccaaggggc ttttattggc tctgcaagtt gagcttgatt ccttaaaggg aaacatacccc  2880 ttccagtcaa agttacagtt actggttggt aaagttaaag ttacagctac tggttgctaa   2940
agcaaccagt ttctccaatt gcatcctgtt gcaaagaaa gtggattctt actgcactga    3000
tgcaaataac cgtattgccc taagttaaga atactcacag atagtttcca aattctagag   3060
gaagcaggca gagagaaaaa aaagtgctaa attttgttca taggagtctg cattactcaa   3120
ttattaaaga ttgtgtatag ctcaaaaaaa aagatcagca ctgttttaag ctaaagttta   3180 aaaagatta cttcaatttt ctattagttc agtctgttca gttaactctt gttctgcttg    3240
atatttgtga acatttcagc tcttcatgag tcctgtacgt ttttccatta ttccaatgtc   3300
acaatctcca aagttatcag aaacctgcat ttgagagcac ctgttacgtt tctatagctg   3360
attataaatc ctatttgaag aagatcaaaa caaaacaatg gtctgtgaat agcaaaatgt   3420
ccatggtagt tacagtcaaa aacacaattg acaaagaaat tttgttatct ctgtggctta   3480
taatcaccta acataacacc tttaattgtg aktgatagca tatacttaga tattagaatt   3540
ttagaaatcc catacagttt tggagcatat attattattc actaaaatat aacccaaaga   3600
```

```
agattaaata tcattttggc aatcccatgt acataaattt gtcaggtaat cctatttacc    3660
tctcttctgg atgctccagg gatgctaggg gtcaggaaag acaaccttga agctgacatt    3720
tgattttggg aagcccatta aatatgttag aggtttaaaa caatgttatg aagtagaatt    3780
ccagattacc ataaattact tattttgcca aaatgatgac tcaaaaattt taaaacaagc    3840
caaaaacttt tactcattta gagggaagac ttagatttcc aaagaatttg tctcctgtct    3900
tcactttcat ttccttggca gtctatctgg aagacaaact gaaatattta attatccttt    3960
actattacat gaaaatctta tacaagggag agaaagccaa attttaccct cacattagtt    4020
tactattaat gtcaaccccca attttttaat gaaaccttat agacaattct atccaatctt    4080
aaccagtttg atcatgaggt aagattcctg taagcctttt ataaccttt acaaattact    4140 aatttactaa tctgctaaag agcagattag ggctttaaga aaaccttgtt gtgctttcat    4200
ttcaatgctc agtttgtaga aaaccatat aatagagttt tggatttaat caatgttcac    4260
acacagaatt tcttttgcaa gattaatttt tagaaacctc ccacaacttg tttaaacctt    4320
tagtttatct tatctaattt ataatagtcc tttaacctta ggcaaaaact tacatttcca    4380
tgcattctta taatctttga ctaataacac attttactgt tcttacatac cttgcatgta    4440
aatctatttt cagtggtctc aattacatgt tataatggta cctcttagca cttttaatt    4500 ttagtttaaa acctggtaag tcgttttaat tacgcactag gtgctgataa agtttgattc    4560
cttccagcat aattaagggt gtggttaatt ccatatgtcc ctgtgcctta ccaagttgta    4620
aagcaggcag attgaacagt tttcaaaggc aaaagaagcc gtttacaacc ttaaaacatt    4680
tagccaccta gtgcctgact tgcataattt agaccagcta tttacatttt aagaacattt    4740
gcattttatc aattatcttt aagactactt ttatttctca gagattaaag tcacaagaac    4800
taaaaggcat tatagctttt atctttcctc caaaaatatt tgatcttagt gctgattttt    4860
ctttaagcca attaattaga gctcttttt ataactacac agatggagaa gaagattgag    4920
tgttataaga ttttttcattt gcccatctcc taattggatt cttggtctct gggtgggacc    4980
ctttaagagc agggctaaga aagcatgcag tttattttct ttttttcttt ttcttttctt    5040 ttttttttgag aaagagtttc actcttgttg cccaggctgg agtgcaatgg tgcgatctca    5100
gctcactgca acctctgcct cccaggttca agcgattctc ttacctcagc ctcccaagtg    5160
gctgcatgca gtttctaggg cctaataaac aggcatagct ggaaaacaaa acgggatttt    5220
gagagcgatc tatttgcctc taattcctgg ggttccatga ggaaaacaga ggttctccc    5280 aaaatggaat ccatggtgcc ttttctgttt ttaccaagca gccctatgcc atcagaaatt    5340
atcttagggc ctctcatgtg cgcattaaca ctggcaagac aaggtggaga aaagtaattc    5400
agtcaactga gaaaaaaatc ttttttccagc aaaacaagat ccaagaagag aaaaacataa    5460
aggcctttca aatatacgta tagcttggat atccactttt aattaagctg agctctcttt    5520
aagaaagtcc ttttaaatcc cacattacct gacttcagcc atgccaagca gccaatattt    5580
ctggctttgg aagtttatca aaagaacctc aaggttcaac caacaagcct caattaagac    5640
acgcgaagca caccagattg gctacacctt aagaccagcc tcataaaacc ttttttcacta    5700 atggaaactt tacagggaat atcaacagtg atccttatca ttcttttcac cagttttcac    5760
agggagagag aggccaaaag tctgactggt taaaaaactt ttatccttt gctggcatgt    5820 catgcttctg ggttccccttc ccctgagctc aattctaagc caaccagttt aaggtttggg    5880
aaattaactt ttctcagttt ggaggatgca tcctatggga atgtccttta gtacagggac    5940
```

-continued

| | |
|---|---|
| acagtcaccc atctgtgaag agaggacaaa ggaggaaaaa gtaaaaaaag atttttttca | 6000 |
| aaggctcccc aggggttcag gatgcatttg aaaggggggac agattgaaga tgaatggcta | 6060 |
| ctcatctaga aagaggggag ccagacatcc ctggttcctt tctctttcta ggaaatagcc | 6120 |
| agggtatgtg agggaaagaa ggaacaagca tccattttcc ttcttccgtc cttatgtccc | 6180 |
| caagtcctga caacctcgac agggtgccac ccatgggtgc caatacggtt ctcacccatg | 6240 |
| gtaacagggg acctagtgga tgggattatc cactgttacc cacaaactgt ctttcccect | 6300 |
| gctctcaata gccttcaagt gccctagacc tcatttaggc cattgatact agtatgacct | 6360 |
| ttatccatga aacaagaggc ttggcttaat tgtcaggaat tagtcatgct cacctatact | 6420 |
| gtgcttttta attttgttg ttgtctgcct ctggatccct ccgatgcagt tatcttcct | 6480 |
| agggcttcta catgaagctt ggaattgagt ttgggacaaa agaactgcct cagtaggtgg | 6540 |
| gtgcatggac tcatcaatcc ccaggtgtcc ctcaccagtc tggctgctgc cgccttatca | 6600 |
| taagctgaag gctaaggtgc aactgtgaaa ttaggtcctt ctcaaacaag ggagggaaaa | 6660 |
| tggtgtcctg tgaattaggg tcctggtcta ataagatgcc ttccaaaagg aagaaaactt | 6720 |
| ctggcacaga gaagacccct ctacccgcag ggctgtgtta ttaggttggt gcgaaagcaa | 6780 |
| ttgtggtgcc catcattcta agtaatgaca aaaaccacaa ctactttcac accagcctac | 6840 |
| taactcatga cttggtggac aaaagaaaat aacaacaaca acaacagctt aaatgcaggg | 6900 |
| ctgtgtttac tgctgacaag gtggagaaaa gaaaatatg cctgagaaat gcaaatgtat | 6960 |
| ttctccaaca ggcagagaaa cttaattgct attgcactga gctggacccc ttggcttggg | 7020 |
| gtggggaaga ctctgtggat acatggcagg ggacactggc cagttggctg catgggccc | 7080 |
| aggcccctga gatcaccctg gggctggggc agcagctgtg gctcaatcct gcactggatg | 7140 |
| gc | 7142 |

<210> SEQ ID NO 7
<211> LENGTH: 3609
<212> TYPE: DNA
<213> ORGANISM: Homo sapiens
<220> FEATURE:
<221> NAME/KEY: allele
<222> LOCATION: (1609)..(1609)
<223> OTHER INFORMATION: y = c or t

<400> SEQUENCE: 7

| | |
|---|---|
| cagacagtca tgcaccccag ccaggaggga agggggaatg gggagatgct gtcttcctat | 60 |
| ccatcctaca catgtgccta tggccattgg gttgggagtg gaacacccc aatattgtaa | 120 |
| aagaaaagat aggtgccatt acaatccccc taaaagaag gaaaatgcca tagaaaagac | 180 |
| tgggttggac tgaggccgat gttcctgacc cctgagagca atgggggggtt gaagggtggg | 240 |
| gtgcaatttc ccccatcctt agaaaacacc tgagaacaag aaagctcaga aacaaaaggg | 300 |
| aaagaaatgt tctgggttca cattttactc acccaggcaa tgtcagcttt ctcattataa | 360 |
| cttttggctt ttgattttt ttttttaatt ttacaatctg gacaaatagt gttttaaata | 420 |
| cctttgtttt aaccccctca atttccattc tatttatttc atttcttaac aaccatccaa | 480 |
| agatttctat cacccttctg gggcgactcc tttgactctc ttttgccttt tcatttttt | 540 |
| tttaaattac ctcaacattt tattaaggat ctgtaagacc cacaagggac agcaaatttg | 600 |
| atacaacttg tcaaacaatt gtatggttct gtcggagaaa tgtcacctgg gatgcctatg | 660 |
| taaagggac ctctttaacc cccaaattta ccatgacctg gtaataggc atataaagtg | 720 |
| ggagaatatc ctggtcatca taaagccagt accatgtggc ttgcttatga atcatatcta | 780 |

```
ctgcttcatc tgggttactc cacttggcat tttataggga gagttgggca gtcccttttct      840 tggggtaaac agactttaca gtggcattta tccagtccac tagggttgga tgttctctca      900
ggaataacct cctatgcatt tggatcactt atactcatta gagatttaat agtgagctgt      960
gggtcatgga tcaaactaaa gaagctcttt cactctgtag catttaaaat taaggattct     1020
atccttaaat tagttatttt taaatccatt atagtaaaag tgtctcagga agctgactat     1080
accaatctac aaaatggaac aattccttta cattatagcc tctggtttta atagttgttt     1140
tgccctgccc ctacatttac tatcttcttg gtaaccacag gtctcagagg taaactttgt     1200
tgccccggtt taatttatat ttttgtgagt agcttggatg ctagaggctt gagctgagac     1260
agacccactt ctggtcttgg tccactctta aggaccaacc caacactctt ttactctcat     1320
ttcagctttt acagataata accaaaggat gaaacatttt tcttccttat tagcttgcct     1380
tcccttatgc attcagggaa ctaactccct gggagtatga gtaggatcca tctctaattc     1440
cactggtaac ttttactttt agtaactgac tatagcccag ctgcagctcc ttaagatggg     1500
caaccacatg gctactcaag agtcaggatt tctcatttca cacccttttta tttttttctt     1560 tatccattta gttttatcta tataattttt tcctttattt tagagtgayt cataaatagt     1620
ctctagaaaa aaattacatt ttctttagca aaaactagtt ccttgtgttt tcagaaacct     1680
caccaaaaac accttttatt cacctactag tttaagtctt attaactcaa attcccagtg     1740
gaaaaaaaac tcataggttt acttaattta aacattacat gacttattaa cccaaatccc     1800
cagtggggga aaaagtaac ctaggtttac ttaatttaaa cataacatga ctttaagatt     1860
ttaaattact ggaaataatt gagattaaat ttaccaaatt aatcttacca aagattacta     1920
gtcatgtgag ctaaaaggca tctgagctag gttccatcag tctgataagc attaacattc     1980
tccaagccaa ttgattagag ctcttttgta ccacttgtta gtgaaatatc acttccacat     2040
ggcacatgta aacatgtaga tataacagac atatagaaaa cggcaggtcc aaaagatttt     2100
tcatttgcct cttttcaaaa attctctccc ctactttaga ttattaattt aaaaaagtta     2160
taaggccaaa caaagttga aggagagagt taccatccta ggccttttca aaagcgaaaa     2220
aaggactgag atatcaattt gaataatttc aaaaagaaac attacagaat ttaaaaatta     2280
aaaactttgt gcattgagta actcaatatt ttaaataaaa tcttgttcta accaaatctt     2340
tagttattta ttagtgtatt ttttttttgag acagagtctt gctcttgttg ctcaggctgg     2400
agtgcaatgg tgcgatctca gctcactgca acttctgcct cccaggttca gtgattctc     2460 ctgcctcagc ttcccaagta gctgggatta caggcacctg ccaccatgcc cagctaattt     2520 tttaatttt agtagagaca gggtttcacc atgttggcca ggctggtctc gaactcctga     2580
cctatatgat ctgctcgcct cggcctccca aagtgctagg attacaggcg tgagcaccgc     2640
acccagtcta gtgtattttt aacataaaag ttcaatttaa aaaaagatt ataattttct     2700 gtaattatgg acaacttaat cacataacat ttgtataaat ttcttttta ctaactttat     2760 tatgacttac acagaccatt cacaacatgc ttggactttc tgctttgacc taagtgtcac     2820
tctttctgga ataactcggt cattttatct taggacaaaa attcaccaaa caatattttt     2880
ctcatacaaa attactttttc ttttaagctt tcttaccaaa ataccctctg tatatctata     2940 ctttttcttta tattggtcta tttcctggtt cctttcacat tcttatttat acaggacttt     3000
taaataagct ttgaattaga caaaaattat ttacctttta ataagaacat attttaaaaa     3060
aagaataaaa tataatttttt tgaattggaa aatacccaga tatttaatta aatatctatt     3120
```

```
attgaattta atataatttt atattctaaa ttatgacaag tttatttaca ggtatttatc    3180
cctttacatt tacctgatta ttttatttta atattttatg tagactatga aaactgtgat    3240
agtcatcatt taaagttatt tccctgtcaa tgattttat agcctatgaa gttcaggtgt      3300
ttacctaagt aagaacctca ggattaaata tatggttatt ttaccaataa ttccaagttt    3360
agctgttttc attaaaccaa caatatttga tatcttgttt gtcaaaaact acacaagcaa    3420
agatcattct gttttgggtt ggtgtattag tctgttctca cattgttatt aaaaaatcct    3480
ggaattgggt aatctataaa gaaaagaggt ttaattggct tacagtttta caggctatat    3540
aggaagcata gcagcttttg cttggaaact tataatcatg gtgaaaggtg aaggtgaagc    3600
aggcatgtc                                                            3609

<210> SEQ ID NO 8
<211> LENGTH: 3659
<212> TYPE: DNA
<213> ORGANISM: Homo sapiens
<220> FEATURE:
<221> NAME/KEY: allele
<222> LOCATION: (1659)..(1659)
<223> OTHER INFORMATION: w = a or t

<400> SEQUENCE: 8
cagacagtca tgcacccccag ccaggaggga agggggaatg gggagatgct gtcttcctat    60
ccatcctaca catgtgccta tggccattgg gttgggagtg aacacccccc aatattgtaa   120
aagaaaagat aggtgccatt acaatccccc taaaagaag gaaaatgcca tagaaaagac    180
tgggttggac tgaggccgat gttcctgacc cctgagagca atgggggggtt gaagggtggg   240 gtgcaatttc ccccatcctt agaaaacacc tgagaacaag aaagctcaga aacaaagg    300 aaagaaatgt tctgggttca cattttactc acccaggcaa tgtcagcttt ctcattataa    360
cttttggctt ttgatttttt tttttaatt ttacaatctg gacaaatagt gttttaaata    420
cctttgtttt aaccccctca atttccattc tatttatttc atttcttaac aaccatccaa    480
agatttctat caccccttctg gggcgactcc tttgactctc ttttgccttt tcattttttt    540
tttaaattac ctcaacattt tattaaggat ctgtaagacc cacaagggac agcaaatttg    600
atacaacttg tcaaacaatt gtatggttct gtcggagaaa tgtcacctgg gatgcctatg    660
taaaagggac ctcttaaacc cccaaattta ccatgacctg ggtaataggc atataaaagtg    720 ggagaatatc ctggtcatca taaagccagt accatgtggc ttgcttatga atcatatcta    780
ctgcttcatc tgggttactc cacttggcat ttataggga gagttgggca gtcccttcct    840
tggggtaaac agactttaca gtggcattta tccagtccac taggttgga tgttctctca    900 ggaataacct cctatgcatt tggatcactt atactcatta gagatttaat agtgagctgt    960
gggtcatgga tcaaactaaa gaagctcttt cactctgtag catttaaaat taaggattct   1020
atccttaaat tagttatttt taaatccatt atagtaaaag tgtctcagga agctgactat   1080
accaatctac aaaatggaac aattccttta cattatagcc tctggttta atagttgttt   1140 tgccctgccc ctacatttac tatcttcttg gtaaccacag gtctcagagg taaactttgt   1200
tgccccggtt taatttatat ttttgtgagt agccttgatg ctagaggctt gagctgagac   1260
agacccactt ctggtcttgg tccactctta aggaccaacc caacactctt ttactctcat   1320
ttcagctttt acagataata accaaaggat gaaacatttt tcttccttat tagcttgcct   1380
tcccttatgc attcagggaa ctaactccct gggagtatga gtaggatcca tctctaattc   1440
cactggtaac ttttacttttt agtaactgac tatagcccag ctgcagctcc ttaagatggg   1500
```

```
caaccacatg gctactcaag agtcaggatt tctcatttca caccctttta ttttttctt    1560 tatccattta gttttatcta tataatttt tcctttattt tagagtgatt cataaatagt    1620
ctctagaaaa aaattacatt ttctttagca aaaactagwt ccttgtgttt tcagaaacct    1680
caccaaaaac accttttatt cacctactag tttaagtctt attaactcaa attcccagtg    1740
gaaaaaaaac tcataggttt acttaattta aacattacat gacttattaa cccaaatccc    1800
cagtggggga aaaagtaac ctaggtttac ttaatttaaa cataacatga ctttaagatt    1860
ttaaattact ggaaataatt gagattaaat ttaccaaatt aatcttacca aagattacta    1920
gtcatgtgag ctaaaaggca tctgagctag gttccatcag tctgataagc attaacattc    1980
tccaagccaa ttgattagag ctcttttgta ccacttgtta gtgaaatatc acttccacat    2040
ggcacatgta aacatgtaga tataacagac atatagaaaa cggcaggtcc aaagatttt    2100 tcatttgcct cttttcaaaa attctctccc ctactttaga ttattaattt aaaaaagtta    2160
taaggccaaa caaagttga aggagagagt taccatccta ggccttttca aaagcgaaaa    2220
aaggactgag atatcaattt gaataatttc aaaagaaac attacagaat ttaaaaatta    2280
aaaactttgt gcattgagta actcaatatt ttaaataaaa tcttgttcta accaaatctt    2340
tagttattta ttagtgtatt ttttttgag acagagtctt gctcttgttg ctcaggctgg    2400
agtgcaatgg tgcgatctca gctcactgca acttctgcct cccaggttca agtgattctc    2460
ctgcctcagc ttcccaagta gctgggatta caggcacctg ccaccatgcc cagctaattt    2520 tttaatttt agtagagaca gggtttcacc atgttggcca ggctggtctc gaactcctga    2580
cctatatgat ctgctcgcct cggcctccca agtgctagg attacaggcg tgagcaccgc    2640
acccagtcta gtgtatttt aacataaaag ttcaatttaa aaaaaagatt ataatttct    2700 gtaattatgg acaacttaat cacataacat ttgtataaat ttcttttta ctaactttat    2760 tatgacttac acagaccatt cacaacatgc ttggactttc tgctttgacc taagtgtcac    2820
tctttctgga ataactcggt cattttatct taggacaaaa attcaccaaa caatatttt    2880 ctcatacaaa attacttttc ttttaagctt tcttaccaaa aatacctctg tatatctata    2940
cttttcttta tattggtcta tttcctggtt cctttcacat tcttatttat acaggacttt    3000
taaataagct ttgaattaga caaaaattat ttaccttta ataagaacat attttaaaaa    3060
aagaataaaa tataattttt tgaattggaa aatacccaga tatttaatta aatatctatt    3120
attgaattta atataatttt atattctaaa ttatgacaag tttatttaca ggtatttatc    3180
cctttacatt tacctgatta ttttatttta atatttatg tagactatga aaactgtgat    3240
agtcatcatt taaagttatt tccctgtcaa tgatttttat agcctatgaa gttcaggtgt    3300
ttacctaagt aagaacctca ggattaaata tatggttatt ttaccaataa ttccaagttt    3360
agctgttttc attaaaccaa caatatttga tatcttgttt gtcaaaaact acacaagcaa    3420
agatcattct gttttgggtt ggtgtattag tctgttctca cattgttatt aaaaaatcct    3480
ggaattgggt aatctataaa gaaagaggt ttaattggct tacagttta caggctatat    3540 aggaagcata gcagcttttg cttggaaact tataatcatg gtgaaaggtg aaggtgaagc    3600
aggcatgtct tacatggctg gagaaggagg aagagaaggt tgttggggag gtgccacac    3659
```

<210> SEQ ID NO 9
<211> LENGTH: 3876
<212> TYPE: DNA
<213> ORGANISM: Homo sapiens
<220> FEATURE:

<221> NAME/KEY: allele
<222> LOCATION: (1876)..(1876)
<223> OTHER INFORMATION: k = g or t

<400> SEQUENCE: 9

```
cagacagtca tgcacccag ccaggaggga aggggggaatg gggagatgct gtcttcctat    60
ccatcctaca catgtgccta tggccattgg gttgggagtg aacaccccc aatattgtaa   120
aagaaaagat aggtgccatt acaatccccc taaaaagaag gaaatgcca tagaaaagac   180
tgggttggac tgaggccgat gttcctgacc cctgagagca atgggggggtt gaagggtggg   240
gtgcaatttc ccccatcctt agaaaacacc tgagaacaag aaagctcaga acaaaaggg   300
aaagaaatgt tctgggttca cattttactc acccaggcaa tgtcagcttt ctcattataa   360
cttttggctt ttgatttttt tttttaatt ttacaatctg acaaatagt gttttaaata   420
cctttgtttt aaccccctca atttccattc tatttatttc atttcttaac aaccatccaa   480
agatttctat caccccttctg gggcgactcc tttgactctc ttttgccttt ctcattttt   540
tttaaattac ctcaacattt tattaaggat ctgtaagacc cacaagggac agcaaatttg   600
atacaacttg tcaaacaatt gtatggttct gtcggagaaa tgtcacctgg gatgcctatg   660
taaagggac ctctttaacc cccaaattta ccatgacctg gtaataggc atataaagtg   720
ggagaatatc ctggtcatca taaagccagt accatgtggc ttgcttatga atcatatcta   780
ctgcttcatc tgggttactc cacttggcat tttataggga gagttgggca gtcccttttct   840
tggggtaaac agactttaca gtggcattta tccagtccac taggggttgga tgttctctca   900
ggataaccct cctatgcatt tggatcactt atactcatta gagattaat agtgagctgt   960
gggtcatgga tcaaactaaa gaagctcttt cactctgtag catttaaaat taaggattct  1020
atccttaaat tagttatttt taaatccatt atagtaaaag tgtctcagga agctgactat  1080
accaatctac aaaatggaac aattcctta cattatagcc tctggtttta atagttgttt  1140
tgccctgccc ctacatttac tatcttcttg gtaaccacag gtctcagagg taaactttgt  1200
tgccccggtt taatttatat ttttgtgagt agcttggatg ctagaggctt gagctgagac  1260
agacccactt ctggtcttgg tccactctta aggaccaacc caacactctt ttactctcat  1320
ttcagctttt acagataata accaaaggat gaaacatttt tcttccttat tagcttgcct  1380
tcccttatgc attcagggaa ctaactccct gggagtatga gtaggatcca tctctaattc  1440
cactggtaac ttttacttt agtaactgac tatagcccag ctgcagctcc ttaagatggg  1500
caaccacatg gctactcaag agtcaggatt tctcatttca cacccttta ttttttttctt  1560
tatccattta gttttatcta tataatttt tcctttattt tagagtgatt cataaatagt  1620
ctctagaaaa aaattacatt ttcttttagca aaaactagtt ccttgtgttt tcagaaacct  1680
caccaaaaac acctttttatt cacctactag tttaagtctt attaactcaa attcccagtg  1740
gaaaaaaac tcataggttt acttaattta aacattacat gacttattaa cccaaatccc  1800
cagtggggga aaaagtaac ctaggtttac ttaatttaaa cataacatga ctttaagatt  1860
ttaaattact ggaaakaatt gagattaaat ttaccaaatt aatcttacca aagattacta  1920
gtcatgtgag ctaaaaggca tctgagctag gttccatcag tctgataagc attaacattc  1980
tccaagccaa ttgattagag ctcttttgta ccacttgtta gtgaaatatc acttccacat  2040
ggcacatgta aacatgtaga tataacagac atatagaaaa cggcaggtcc aaagatttt  2100
tcatttgcct cttttcaaaa attctctccc ctacttttaga ttattaattt aaaaagtta  2160
taaggccaaa caaaagttga aggagagagt taccatccta ggcctttcca aaagcgaaaa  2220
```

| | |
|---|---|
| aaggactgag atatcaattt gaataatttc aaaaagaaac attacagaat ttaaaaatta | 2280 |
| aaaactttgt gcattgagta actcaatatt ttaaataaaa tcttgttcta accaaatctt | 2340 |
| tagttattta ttagtgtatt ttttttgag acagagtctt gctcttgttg ctcaggctgg | 2400 |
| agtgcaatgg tgcgatctca gctcactgca acttctgcct cccaggttca agtgattctc | 2460 |
| ctgcctcagc ttcccaagta gctgggatta caggcacctg ccaccatgcc cagctaattt | 2520 |
| tttaattttt agtagagaca gggtttcacc atgttggcca ggctggtctc gaactcctga | 2580 |
| cctatatgat ctgctcgcct cggcctccca agtgctagg attacaggcg tgagcaccgc | 2640 |
| acccagtcta gtgtatttt aacataaaag ttcaatttaa aaaaagatt ataattttct | 2700 |
| gtaattatgg acaacttaat cacataacat ttgtataaat ttctttttta ctaactttat | 2760 |
| tatgacttac acagaccatt cacaacatgc ttggactttc tgctttgacc taagtgtcac | 2820 |
| tctttctgga ataactcggt cattttatct taggacaaaa attcaccaaa caatattttt | 2880 |
| ctcatacaaa attactttc ttttaagctt tcttaccaaa aatacctctg tatatctata | 2940 |
| cttttcttta tattggtcta tttcctggtt cctttcacat tcttatttat acaggacttt | 3000 |
| taaataagct ttgaattaga caaaaattat ttacctttta ataagaacat attttaaaaa | 3060 |
| aagaataaaa tataattttt tgaattggaa atacccaga tatttaatta aatatctatt | 3120 |
| attgaattta atataatttt atattctaaa ttatgacaag tttatttaca ggtatttatc | 3180 |
| cctttacatt tacctgatta ttttattta atatttttatg tagactatga aaactgtgat | 3240 |
| agtcatcatt taaagttatt tccctgtcaa tgattttat agcctatgaa gttcaggtgt | 3300 |
| ttacctaagt aagaacctca ggattaaata tatggttatt ttaccaataa ttccaagttt | 3360 |
| agctgttttc attaaaccaa caatatttga tatcttgttt gtcaaaaact acacaagcaa | 3420 |
| agatcattct gttttgggtt ggtgtattag tctgttctca cattgttatt aaaaaatcct | 3480 |
| ggaattgggt aatctataaa gaaaagaggt ttaattggct tacagttta caggctatat | 3540 |
| aggaagcata gcagcttttg cttggaaact tataatcatg gtgaaaggtg aaggtgaagc | 3600 |
| aggcatgtct tacatggctg gagaaggagg aagagaaggt tgttggggag gtgccacaca | 3660 |
| ctttaaaca accagatctc atgagaactt actatcacca tgcagcccc aaggggatg | 3720 |
| gtgttaaacc atgagaaact accccatgat ccaatcacct tccaccaggt tcctcctcca | 3780 |
| acactgggga ttacaatttg acatgagatt tgggtgggga tacagatcca accataacgg | 3840 |
| ttgggtttac agttttataa actttatgtc aaattt | 3876 |

<210> SEQ ID NO 10
<211> LENGTH: 6995
<212> TYPE: DNA
<213> ORGANISM: Homo sapiens
<220> FEATURE:
<221> NAME/KEY: allele
<222> LOCATION: (3428)..(3428)
<223> OTHER INFORMATION: y = c or t

<400> SEQUENCE: 10

| | |
|---|---|
| tgtcttccta tccatcctac acatgtgcct atggccattg ggttgggagt ggaacacccc | 60 |
| caatattgta aagaaaaga taggtgccat tacaatcccc ctaaaagaa ggaaaatgcc | 120 |
| atagaaaaga ctgggttgga ctgaggccga tgttcctgac ccctgagagc aatgggggt | 180 |
| tgaagggtgg ggtgcaattt cccccatcct tagaaaacac ctgagaacaa gaaagctcag | 240 |
| aaacaaaagg gaaagaaatg ttctgggttc acatttact cacccaggca atgtcagctt | 300 |

```
tctcattata actttTggct tttgatttTt tTtttTtaat tttacaatct ggacaaatag    360
tgtTtTaaat acctTtgtTt taaccCcctc aaTttccatt ctatTtattt catTtcttaa    420
caaccatcca aagatTtcta tcacccttct ggggcgactc cttTgactct ctttTgcctt    480
tctcatTTtt ttTtaaatta cctcaacatt tTatTaagga tctgtaagac ccacaaggga    540
cagcaaattT gatacaactT gtcaaacaat tgtatggttc tgtcggagaa atgtcacctg    600
ggatgcctat gtaaaaggga cctctTtaac cCccaaatTt accatgacct gggtaatagg    660
catataaagt gggagaatat cctggtcatc ataaagccag taccatgtgg cttgcttatg    720
aatcatatct actgcttcat ctgggttact ccacttggca ttTtataggg agagttgggc    780
agtcccttTc ttggggtaaa cagactTTac agtggcattT atccagtcca ctagggttgg    840
atgttctctc aggaataacc tcctatgcat ttggatcact tatactcatt agagatttaa    900
tagtgagctg tgggtcatgg atcaaactaa agaagctctt tcactctgta gcatttaaaa    960
ttaaggattc tatccttaaa ttagttattt ttaaatccat tatagtaaaa gtgtctcagg   1020
aagctgacta taccaatcta caaaatggaa caattccttt acattatagc ctctggtttt   1080
aatagttgtt ttgccctgcc cctacattTa ctatcttctt ggtaaccaca ggtctcagag   1140
gtaaactTTg ttgccccggt ttaatttata ttTTtgtgag tagcttggat gctagaggct   1200
tgagctgaga cagacccact tctggtcttg gtccactctt aaggaccaac ccaacactct   1260
tttactctca tttcagctTt tacagataat aaccaaagga tgaaacattt ttcttcctta   1320
ttagcttgcc ttcccttatg cattcaggga actaactccc tgggagtatg agtaggatcc   1380
atctctaatt ccactggtaa cttttacttt tagtaactga ctatagccca gctgcagctc   1440
ctTaagatgg gcaaccacat ggctactcaa gagtcaggat ttctcatttc acacccttTt   1500
attTTtTtct ttatccattt agtTttatct atataattTt ttcctttatt ttagagtgat   1560
tcataaatag tctctagaaa aaaattacat tttctttagc aaaaactagt tccttgtgtt   1620
ttcagaaacc tcaccaaaaa caccttttat tcacctacta gtttaagtct tattaactca   1680
aattcccagt ggaaaaaaaa ctcataggtt tacttaattt aaacattaca tgacttatta   1740
acccaaatcc ccagtgggGg aaaaaagtaa cctaggtTta cttaatttaa acataacatg   1800
actTtaagat tttaaattac tggaaataat tgagattaaa tttaccaaat taatcttacc   1860
aaagattact agtcatgtga gctaaaaggc atctgagcta ggttccatca gtctgataag   1920
cattaacatt ctccaagcca attgattaga gctcttTtgt accacttgtt agtgaaatat   1980
cacttccaca tggcacatgt aaacatgtag atataacaga catatagaaa acggcaggtc   2040
caaaagatTt ttcatttgcc tcttttcaaa aattctctcc cctactttag attattaatt   2100
taaaaaagtt ataaggccaa acaaaagttg aaggagagag ttaccatcct aggccttttc   2160
aaaagcgaaa aaaggactga gatatcaatt tgaataattt caaaaagaaa cattacagaa   2220
ttTaaaaatt aaaaactttg tgcattgagt aactcaatat tttaaataaa atcttgttct   2280
aaccaaatct ttagttattt attagtgtat ttTtttTtga cacagagtct tgctcttgtt   2340
gctcaggctg gagtgcaatg gtgcgatctc agctcactgc aacttctgcc tcccaggttc   2400
aagtgattct cctgcctcag cttcccaagt agctgggatt acaggcacct gccaccatgc   2460
ccagctaatt ttTtaatttt tagtagagac agggtttcac catgttggcc aggctggtct   2520
cgaactcctg acctatatga tctgctcgcc tcggcctccc aaagtgctag gattacaggc   2580
gtgagcaccg cacccagtct agtgtatttT taacataaaa gttcaattTa aaaaaaagat   2640
tataatttTc tgtaattatg gacaacttaa tcacataaca tTtgtataaa tttctttttt   2700
```

```
actaacttta ttatgactta cacagaccat tcacaacatg cttggacttt ctgctttgac    2760
ctaagtgtca ctctttctgg aataactcgg tcattttatc ttaggacaaa aattcaccaa    2820
acaatatttt tctcatacaa aattactttt cttttaagct ttcttaccaa aaatacctct    2880
gtatatctat acttttcttt atattggtct atttcctggt tcctttcaca ttcttattta    2940
tacaggactt ttaaataagc tttgaattag acaaaaatta tttacctttt aataagaaca    3000
tattttaaaa aaagaataaa atataatttt ttgaattgga aaatacccag atatttaatt    3060
aaatatctat tattgaattt aatataattt tatattctaa attatgacaa gtttatttac    3120
aggtatttat ccctttacat ttacctgatt attttatttt aatatttat gtagactatg     3180 aaaactgtga tagtcatcat ttaaagttat ttccctgtca atgattttta tagcctatga    3240
agttcaggtg tttacctaag taagaacctc aggattaaat atatggttat tttaccaata    3300
attccaagtt tagctgtttt cattaaacca acaatatttg atatcttgtt tgtcaaaaac    3360
tacacaagca aagatcattc tgttttgggt tggtgtatta gtctgttctc acattgttat    3420
taaaaaaycc tggaattggg taatctataa agaaagagg tttaattggc ttacagttttt    3480 acaggctata taggaagcat agcagctttt gcttggaaac ttataatcat ggtgaaaggt    3540
gaaggtgaag caggcatgtc ttacatggct ggagaaggag aagagaagg ttgttgggga     3600 ggtgccacac acttttaaac aaccagatct catgagaact tactatcacc atgacagccc    3660
caagggggat ggtgttaaac catgagaaac taccccatga tccaatcacc ttccaccagg    3720
ttcctcctcc aacactgggg attacaattt gacatgagat ttgggtgggg atacagatcc    3780
aaccataacg gttgggttta cagttttata aactttatgt caaattttga cacagagtat    3840
ttgtcaggga taagtatgaa attgctgatc aataaatgca acaaaaata tatgttgaca     3900 atttataaga catttctaat attacttgac caataatttt aagccagttt atttataaaa    3960
ggttttactt gtcacatgac cttgaaaagc atttgggctt attgtttaat gtatgagtac    4020
ccttcaactt taagccattt tagtaccttg tggccaaaaa cacataataa aatacatgtt    4080
tgtacacata aacacacata tacacactca tacaaagatc ctgttgcttt cacttcaaaa    4140
ttttagctat gagatattaa tataaactta ccagtttgca aaaacaataa caaaaagaaa    4200
cggttggatg caaacagtgg attttatctc agtagaaatg tgttaataat agcagacaaa    4260
gcaggtggaa aagaaaacag agatagagaa cttaggaact ttagagttgc aggttgaact    4320
ttaggttctg aattttcctt gatgtaattt gcccatcagt ttaaaatgcg cacaagaaca    4380
gacctaatgt gtaaccagct ggagtattag aaaacctggc acgcccttcc atttacacaa    4440
ccacttgcaa gtagaggcac catgaaacga aatgaggtgc ctgagaggcc ttgttcttgt    4500
ttttccatat ccttaattta ttccccacat attttcttaa aaggaggaac tgagctgtgg    4560
cctaagtttt agtttagtgg gtcaaaatat gctgattctg ggtggggctc cacagtgtgt    4620
caccagtgag tcgttgccac cctcttatgt atctcagttt ctctctctgg aggtttagac    4680
ctccgagtgc tcaaaacatg gagttcctac atgagcttcc tggatgaacc ttttttaaact   4740 aattttgctg ggggttccct gtagggcggc tgcatttcat ggggttggta gtcaacccct    4800
taggctccac cccagtaacc cagggatgcc ttttggctgg aaggagcaaa atgccctttc    4860
ttttcagagc ttaggaaact cagtctgaca tttatctaca aaaacaacag tttagttgct    4920
ctcacaaata cacagacaag ccaatcgaga ttaattttgg gagagaagac aatgagaaag    4980
ctctttagaa tgcacctctg aactagaatt aggatcctaa acaacaactt cattggtggg    5040
```

```
ggcagcgggg tggaaaaagc taagaccagc tgtaaactgt cctcagccac tcctaacttt    5100
atagctcttg tctgccatta cacactccaa ggtcacatct tctcacagta caaggtaatc    5160
tctggtgccc gcaaaagcca agagggtcag gtaatgcaat acaggaaagc agagttttaa    5220
atctaagaag aatctgccca tgactcttga acccccacaa agaaaacaga acaccccaaa    5280
agggggtggg agtggtgcct tgttctgag ttctttaagg ggtctgagac attagaaccc     5340
ttctgtagat ttttcttggt accagagatg gtgaagggggg aaggaaaat agagtggaac    5400 aaaagtaaac agaagaataa ctgttttttg ttttttttt ttaagaaagg aagtgaacac     5460
agaaaccaag cacatgtttt tgttttttgtt tgtgcagctg ccaggaattt tagccaattc   5520
agaggccttg tttcccctaa tttggaattc tcattggaat ttgaccaagt ctgttatagt    5580
tgatcaaatc ctatgggaga agatcagaa caacaaaaac cccaacaata tgattactga     5640
gtgctctaac ggtaaggaga aattaaaacc agctgcttgt caatttcaac ttgtagtcat    5700
taaggagaat ttccaagaca aaaaaatccc aattcttgct acttacctag aatagagcc    5760 ctggcacaag attgctcttt accatcttag aagcaggaaa aatacctgga aaggtgcaca    5820
ggaacagaca taaggttctt gccttcccta tcggaaacta gctgaaactc cagaaatgag    5880
ttacctgcta tgcatcatca tggaagcaga aaaacttgct ttccttgttg gaatcaagta    5940
aaactccaga aaaggagttg tagagcaaaa taagctttag atctcgacca aattttgaga    6000
gatcagggat tctctggagg gggaactccc aggcctcagc aaattgtcct tctgatttga    6060
gccataagga tagctcaagc tggtaccaag caccaataga ttcatcaaag gtcaggggca    6120
cctccactca gaatcccttc atcaccaatt tgtgaactca aaagtatctg agacagatct    6180
caatacattt agacggttta ttttgccaag gttaaggatg tgcccatgac acatgtgccc    6240 atgcacacagc ctcaggaggt cctgatgaca tgtgcccacg gtggtcaggg tacaacttgc   6300
ttttatactt tttagggagg cataatacat caatcaatac ctgtaagatg tacactggtt    6360
caatctggaa aagcaggaca acttgaagtg ggggcttcca ggttataggt agatttaaga    6420
attttctgat tggcaatttg ttgaaagagt tatgttgtta cccaaagacc cagaatcaat    6480 agaaataccct gggttatgat gataaggggt tgtagagacc aaagtttatc aggcagatga    6540
agcctccagg tagcagattt cagagagaat agattgaaaa tgtttcttat cagacgtaag    6600
tttaatgctg gtcagctttt cctaagttcc aaaaggaggg aggtatact gagttatatc     6660 caactctccc ttcccatcat ggcctgaact agttttcag gttaacttta caatgcgctt    6720
ggccaagagg gggcgtccgt ttagatggtt tgaggtgggg agggcttaca atttatttt    6780 tggcttacat agtaaaggtt aattatctca atacaattag gtcatcttca tttttctttt    6840
aaaaactttt gtcttccttt atctccctga atacacaggc agtttactat tttctcattg    6900
caagacccat tctcaaatat tattttcttt tagagagact cttgctgtta tttaggttca    6960
caagatggtg tcagaagtga aataaaagtg gcctc                              6995
```

<210> SEQ ID NO 11
<211> LENGTH: 601
<212> TYPE: DNA
<213> ORGANISM: Homo sapiens
<220> FEATURE:
<221> NAME/KEY: allele
<222> LOCATION: (301)..(301)
<223> OTHER INFORMATION: r = a or g

<400> SEQUENCE: 11

```
tgaaatgctc tattctttgc ctcaagtgat cctcctacct cggcctccca agtgctggg       60
```

```
attacaggca tggagccaac acacctggcc ttcacatcta tttttaatcc aagtaattct    120
agggtcaaat aatactgaaa tctcgctaag tatcaaacgc tgcttttaac tgaagaaagt    180
ttactttgtt ttatttta tt tttaaaatct tgctttgtct ctagatagac accataaatc   240
agaacttctt aatctaagat aacatcctgc tgctcaaaaa caggtgtcag aggaggcaat    300
rcatgcagct ggctcattag tctatatcac agatgccaca acatgctgt cttgaggaac    360 tagaaacgtg cttttttgaa atatgttctt cagaagttct taggagctgt ggtgggagag    420
cgcaagcctg gggtgagga ggcagctgag tgggtgattc ttctcactat tgcatcaaca    480
agagtagtag ctatagactg ggtttcttat tcttctacta gaggccccg aaataaaatg     540 gcttttaaa ggacctggtc taaagctttt ttcttttctt ttcttttctg atttttttt     600 t                                                                   601
```

```
<210> SEQ ID NO 12
<211> LENGTH: 2429
<212> TYPE: DNA
<213> ORGANISM: Homo sapiens
<220> FEATURE:
<221> NAME/KEY: allele
<222> LOCATION: (2000)..(2000)
<223> OTHER INFORMATION: r = a or g

<400> SEQUENCE: 12
aaataaaaag atttgattaa attttttaaa tgggcaaagg atctcaatgg acaattctcc     60
aaggaaggta caaaatagcc aataagcata aacagaagc tcaacatcat taattagcag    120
gtaaatgcaa ataaaaacca catgagttac cattttatac ctattaggat ggctatagtc    180 aaaaagatt ggtaaaaatg tggaaaaatc aaaactctca tatattgctg atgggaatgt     240
aaaatagtgc agatgctttg aaagtagtct ggcatttcct caaatgatta aatatagagt    300
tactatgaga cccagcaatt ccactcctat gtatatattg aagagaaata taaggtatg    360 cccagctatg tgtggtggcg tatgcctgat agtccttggt acttgggagg ctgaggtgga    420
aggattgctg gagcccaggg gttcaagact gaagtgagct atgtttgtgc cactgcgctc    480
cagcccaggt gacagagcag gatcctgtct ctcaaaaaaa caaacaagaa aaaaaaacaa    540
aaaaactcac actcaaaaat ttttacatga ctgtttatag tagcattatt cataatagcc    600
aaaaagtgga aactacccaa atgtctatca actgaagaaa ggataaataa tatgtggtat    660
atccatataa tgtattattt ggtcacaaaa aagaatgaag tactgataca tactacaatc    720
tgaatgaact ttgaaaacac gttaagtgaa agaagccagt caaaaaaatc atgtattata    780
ttagtctatc tagaacaggg aactctatag agacagaaag attagtagtt gccggggctg    840
agggctaagg gaatggtgag actggaaggt gatagccaaa gggtatggag ttgcttttg    900 aggtgataaa aatgttctaa aattgactgt gagtgatggt tgtacatatt tgtgaatata    960
gtaaaaacca ttaaactgta tgctatatgc ttaaagtata ggctgtgtga attatatctc   1020
aataaggctg tttaaaaaaa tctaagtgga tgcagtgacc atctatttcc ccagtgtcct   1080
gtagttgctc tatgggctct tgaacaaaat agttgcatga tggaggctat atatagactt   1140
aacaatatgg atctcctctt accaaagttg gtctgacctg cagagtgtcc aactttccag   1200
taaggaagat caatgttgaa cccctagtat agtgccatat tccaggggct ctcatcttcc   1260
atctcgttgc aggtaggttt atttttgttc ccttccaaaa gggaggggc aagagacatt    1320 ggttatagat tttcttact gctggatata gattctggtt acagattttg tttatagatt    1380
```

| | |
|---|---:|
| tttatttact gcttcaatgc tttttattagc agacccctaa ccactcctgg gaccacacat | 1440 |
| acacccatag atgtagtcaa tgccttgttc atgagcatag tactccacaa tacattgctt | 1500 |
| atgacaaaga acttaagtta atgtgaaagg agtgaagcaa ggtctcaaga cccataggac | 1560 |
| aaatatatat catatatttg tcgctcagaa atccatgact ttataggaag gtgaaatgga | 1620 |
| taattgaaaa ctcagtttga gagacgtctt gtgaattggc atatgaattg gtaaatgctc | 1680 |
| caattggtaa atgcttcact aagcctaggg ccaatatatg gtgctatttc ttccacagac | 1740 |
| agaattcact ggtctaggat acaagaagta gaagtgggag gggcaactct gactgttacc | 1800 |
| catagtgaac aacttatgac atgttttttgt ttcccatatg cttggccttg aattcttctg | 1860 |
| gtttataaca aaaatggttt ccaaaaattg gaagtcgagg ctctctcctg accatttgga | 1920 |
| gcgcctcatg ccatttaact aacaaaaaga aaatgaggtt cttatattgt ctagggtgat | 1980 |
| tcattctgat tttcaaggcr taatatagtt ataaatacaa tggggtcagg tggaagaatt | 2040 |
| cttggtatcc tctggtgtgc ctcttagagc ttctctattc agtgataaaa attaatgtaa | 2100 |
| ggttaggtca agcggagaca ggaaacacca aaaggactca aactcctcgt ggataaagag | 2160 |
| ctgaagtgct ggctggaaag aaagtgaatg ttgagtttat aatgaaggaa gaagtcataa | 2220 |
| atattaacta cagcttcatg actagttgac ttgttgcaat tatgaggact gtggtaaata | 2280 |
| tcttttttttt ttcttgttct atttatgcac atctttatat ctatacatta aaccccttct | 2340 |
| ctctctctct ctactatttt atccaatgtc tgttggtaat ggttaatttt aacacctatg | 2400 |
| tcttagatta tattattcta tggttgtga | 2429 |

```
<210> SEQ ID NO 13
<211> LENGTH: 778
<212> TYPE: DNA
<213> ORGANISM: Homo sapiens
<220> FEATURE:
<221> NAME/KEY: allele
<222> LOCATION: (391)..(391)
<223> OTHER INFORMATION: m = a or c

<400> SEQUENCE: 13
```

| | |
|---|---:|
| tcactgcctg atcagtcatc tttagaacat aaacattcca gaagttttca ggagatgaca | 60 |
| ggcacaattt cctgaaggcc tgcctagaat tgatttgcta acatgaagat agatggctta | 120 |
| atgcccttaa tctctctgtc tatggatttc ttctctcatt tttgtaacat cagtgctacc | 180 |
| accaccaaca gtaataacac tgcaccaggc actgagggac ttttatctgc attcactcat | 240 |
| ttaatttgcc cagctcttct gtgaggaagg tactgtgcat tatggtcttc ctcttacaga | 300 |
| ctgaaaaaac gaagccttgg acacctgaag gagattgcca ggcagccaat ggtgaagctg | 360 |
| attttgtacc cagacagtct gagtgcagag mctgccatta ccctccaaca gaaaaccaag | 420 |
| agcaaagcca tgggagagag gagctaatga aagaggcaga ccaattagaa gctgaggcta | 480 |
| tactttatct tcttccttct tccctcctcc tcctccttct ggccggcatt catcaaacat | 540 |
| tgaacatata tgaacattaa cttatgttag gcactatgtt caaagcttta caacttactt | 600 |
| aattcccaca gccaccaagt aaggtaaata ttttttattat cgcattctac agatgaggaa | 660 |
| gctgaggctt tagaaagttg catctcttac tcgaggttac aggtttggta agatgcagag | 720 |
| ccaggaacat tttggtagca tttgaattcc tgccgtattt tgctaaatgt gcccttgc | 778 |

```
<210> SEQ ID NO 14
<211> LENGTH: 1001
<212> TYPE: DNA
<213> ORGANISM: Homo sapiens
```

```
<220> FEATURE:
<221> NAME/KEY: allele
<222> LOCATION: (501)..(501)
<223> OTHER INFORMATION: w = a or t

<400> SEQUENCE: 14
ctaacattaa aaaggacatt gaaatagggg gctggaaaga taatgaatgg cccctgggc         60 acaagatggg tcatggggat actgtactcc tatttatatg ttaaaccaca tcataaggtt       120
gcaagcagtt ctggaaatta tagtcaatga aacagcctga gccttagact tgctagccat       180
acaggcaacc cagatgagag atgccattta tcagaacagg ttagtactga attatgtttt       240
agcttcagaa gggggtttgt ggaaaactta atttaacaaa ttgctgctta caaattgatg       300
acaatggaaa agctgtcatg gaaatcactg ccaggatgcg gaagttagct catgttctgg       360
ttcagacatg gtctggttgg aacccgagtt cactctttgg aggacggttt tcatggtttg       420
gaggctttaa aactgtaata ctaggctttg tggccataaa aggtggatgc ctactgcttc       480
cctgtctctt gccatttcta wtcggaagca tccaatccac catagactca atggtagaca       540
gacataccac catccgaata aaggctctgc aaaagtacca actggtatcc caagatgagt       600
atgtacccca tcaagaagaa atagctaact gtggtgctct ttattaatct acatttgtgt       660
cgagcaccaa aagggggaaa tgaagaagga attaatgaaa tcaactataa cctaagagta       720
gtagtaatac aaatttttaaa atccttttaa agttcctgca aaatgtgacc cctgccttac      780
attcacgtta aagggaata ttaacagcct gtcttctctc tgtggacagt ggaccttatc        840
tatactcccc aactccacat tcctcaaagt ttattacagg cccagtgagt tcctgcatga       900
ctgcagggtc acaagactga taagtttagg ctgcaagaca tgtctttctc aaaatgtaac      960
aaacgttgta atactgcctt tgtttcttgc ttctgtaact c                         1001

<210> SEQ ID NO 15
<211> LENGTH: 7028
<212> TYPE: DNA
<213> ORGANISM: Homo sapiens
<220> FEATURE:
<221> NAME/KEY: allele
<222> LOCATION: (642)..(642)
<223> OTHER INFORMATION: k = g or t

<400> SEQUENCE: 15
catatgaaca aaggtctgag ttgggtgagg caggatgcca cacagacatt ggaggaggaa        60
aatctgagca gggggcacag caaagcccca aggctgaggc cagatgaagg agcaggaggc      120
aatgtggctg gagaggaggg agcaagggc agagtgttgg tggtgaggtc aggggcccag       180
cagcctgatc caggggactt gaacaggatg gaaggacttt gggtgcgttc tgaagaaggg      240
gaagccactg gaaggcatta agtagaaaaa attggaagtg agagtaatta tatgtgaaag      300
ttgttagagt cacaatggag tgacgatgag gcaggacagg tagtcaagga agtaagtgca      360
gttaacacaa tgagcccag tattcgcatt gtaatccagc tcatgcaagc acagctatct       420
cctgcaggga atatttccca tagacagcat ttgcactttg attttacctc ttctcaaacg      480
gaccctgttc tcatgataat agtaaaaaac caccccctag gtggagattt aagatgctga     540
tgaattatga gatgtatgaa caagcatgta cagctactgc acatgtgcac ccagaggacc      600
accgaggaca tgcttactag caacaccttt tctcacccctc tkatgaataa tcatgtaaga     660
gtcccataaa aggatttctc cagcaataat cagtgctgtc cattcagtgg ctcatgcctg      720
taacccagca ctttgggagg ccgaggtggg tggatcacct gaggtcagga gtttgagacc      780
```

```
agcctggtca acatggtgaa acctcgtttc tattaaaaat acaaaaaaag tagccaggtg    840
taatggcaca tgcctgtaat cccagctact tgggaggctg aagcaggaga actgattgaa    900
cctgggaggt ggaggttgca gtgagtcatg actgtgccac tgcactccag ccaacagagt    960
aagactctgt tcccccctcgg ccccctgcaa aaaaaaataa taacaatgat aagaggcaag   1020
atcaatggcc accaaaattt tattttttcc catagcgttg ctggggtggc atggctgcct   1080
gccctgggtt catcctgtcc ctaagtggaa ctccctatgg ctgagggact cagaatcaaa   1140
tgacttatag ccaattaaat gttctagtcc agatgcccaa ttaaatgggc atggacagac   1200
attcattagc cttttaaatta ttttctaagt aaaaagtcaa caaacaaaaa gttaaaggtg   1260
aggttacaaa actgactttt ctttaacttc tatgctactg taatcttggg ttttgttatg   1320
gacttatagc aattatttat acaaaacata agaattgttc tgaaaaaatt aaaaaatata   1380
tacctgcatg gctcataact ggaaatatta taccaggagg ctttgtcact tggtatcttt   1440
atccttttac ttattatttt cttttaattc tacaggaagc agtaaattct ttatggttgg   1500
agtggatgaa gaggtgccat gtaatagctc agaaggcaaa gtcccttgtt ttaccagctg   1560
tttaggcatc catgtactca tccttgattt gaagggtttg agttaattct atccttccaa   1620 atcagcccctt acaatctcac gtgcccacct cttctgcaac agtctctggg cctagaggga   1680
ggacgcttgc aatacaggat tttttgcatg ttcccagtgg ctccacccca ttctcccagt   1740
gcacatgcag gcccttagtc tgaacccacg ctacattgat ttatttccct tactgagcat   1800
gtgttaaggg atggaatttt tcaccatggg catgtttagg caagccccct gtacacaatg   1860
tcctggatgc catttggctg tcttctgcct ctatcattcc cccatctaaa agagtacatc   1920
taactgccat tagaataagg ataagaagaa agacaaagac ccatcttaac tgctttctgc   1980
tgacagaggg cactgttttg gaaagacagc agttgggtct ccctcagagg cctatctaag   2040
ggtatctggt aaaagggacc atcattcgag gctctggttg cataactgtt tggagtttga   2100
gggcctgaag gcgagaagag acaaaccagg ttattagaag acatgtacca aaatgaaatg   2160
ggggaagggt aaggacagtt caaaaatcct gaggctgctg acatgcccag ataactggta   2220
gctgtagttg tgcctgctaa gatttgggtg catgggactt ggctttggtt agctcccgta   2280 gtttatttc ccaaaaaaga aacctctggg ttatgggcac cctatttact cccattatct   2340
ggcaggattt gtaggataat tgttcagaac tagaatactg ttccagattt ttacattacc   2400
catgcctttt gtttcttctg agctgcagcc agagatcact ggttagttca caggaataag   2460
cagggttaat ttaaaatgta ggcaaaaaac ttaaaaacaa ctaatgagtc tagaatttaa   2520
tgacaaatgt atgataagtt ttgaaacata atttctttct ccccagtcct cattttttgtt   2580 aaaaacaaat cataatagga gtgagttgtt tgtaaaataa actttagtct tacacttggt   2640
ctgcttattt gcacaaagta caacaagaat aattattttt acataggctt tttaaattgg   2700
ctttgatgga actctgttcc acaaggaatt tcagatagga cttcataaaa atgagcccag   2760
ccatgggttt gtaccctcta ataccctatga gttgggtgaa ttgctctctt cttgaggtcc   2820
caagaatatg cggttcctgg ccctgttaga aagtgacatt cttttactcac tacaggttag   2880 ggaacctgta tggggactgt gtagacaaag tatgaggctg gttacccaa ggggctttta   2940 ttggctctgc aagttgagct tgattcctta aagggaaaca tacccttcca gtcaaagtta   3000
cagttactgg ttggtaaagt taagttaca gctactggtt gctaaagcaa ccagtttctc   3060
caattgcatc ctgttgcaaa agaaagtgga ttcttactgc actgatgcaa ataaccgtat   3120
tgccctaagt taagaatact cacagatagt ttccaaattc tagaggaagc aggcagagag   3180
```

```
aaaaaaaagt gctaaatttt gttcatagga gtctgcatta ctcaattatt aaagattgtg    3240
tatagctcaa aaaaaagat cagcactgtt ttaagctaaa gtttaaaaaa gattacttca    3300
attttctatt agttcagtct gttcagttaa ctcttgttct gcttgatatt tgtgaacatt    3360
tcagctcttc atgagtcctg tacgtttttc cattattcca atgtcacaat ctccaaagtt    3420
atcagaaacc tgcatttgag agcacctgtt acgtttctat agctgattat aaatcctatt    3480
tgaagaagat caaacaaaa caatggtctg tgaatagcaa aatgtccatg gtagttacag    3540
tcaaaaacac aattgacaaa gaaattttgt tatctctgtg gcttataatc acctaacata    3600
acacctttaa ttgtgagtga tagcatatac ttagatatta gaattttaga aatcccatac    3660
agttttggag catatattat tattcactaa aatataaccc aaagaagatt aaatatcatt    3720
ttggcaatcc catgtacata aatttgtcag gtaatcctat ttacctctct tctggatgct    3780
ccagggatgc taggggtcag gaaagacaac cttgaagctg acatttgatt ttgggaagcc    3840
cattaaatat gttagaggtt taaacaatg ttatgaagta gaattccaga ttaccataaa    3900
ttacttattt tgccaaaatg atgactcaaa aattttaaaa caagccaaaa acttttactc    3960
atttagaggg aagacttaga tttccaaaga atttgtctcc tgtcttcact ttcatttcct    4020
tggcagtcta tctggaagac aaactgaaat atttaattat cctttactat tacatgaaaa    4080
tcttatacaa gggagagaaa gccaaatttt accctcacat tagttactta ttaatgtcaa    4140
ccccaatttt ttaatgaaac cttatagaca attctatcca atcttaacca gtttgatcat    4200
gaggtaagat tcctgtaagc cttttataac cttttacaaa ttactaattt actaatctgc    4260
taaagagcag attagggctt taagaaaacc ttgttgtgct ttcatttcaa tgctcagttt    4320
gtagaaaaac catataatag agttttggat ttaatcaatg ttcacacaca gaatttcttt    4380
tgcaagatta attttagaa acctcccaca acttgtttaa acctttagtt tatcttatct    4440
aatttataat agtcctttaa ccttaggcaa aaacttacat ttccatgcat tcttataatc    4500
tttgactaat aacacatttt actgttctta cataccttgc atgtaaatct atttcagtg    4560 gtctcaatta catgttataa tggtacctct tagcactttt taattttagt ttaaaacctg    4620
gtaagtcgtt ttaattacgc actaggtgct gataaagttt gattccttcc agcataatta    4680
agggtgtggt taattccata tgtccctgtg ccttaccaag ttgtaaagca ggcagattga    4740
acagttttca aaggcaaaag aagccgttta caaccttaaa acatttagcc acctagtgcc    4800
tgacttgcat aatttagacc agctatttac attttaagaa catttgcatt ttatcaatta    4860
tctttaagac tacttttatt tctcagagat taaagtcaca agaactaaaa ggcattatag    4920
cttttatctt tcctccaaaa atatttgatc ttagtgctga tttttcttta agccaattaa    4980
ttagagctct tttttataac tacacagatg gagaagaaga ttgagtgtta taagattttt    5040
catttgccca tctcctaatt ggattcttgg tctctgggtg ggaccccttta agagcagggc    5100 taagaaagca tgcagtttat tttcttttttt tcttttttctt ttcttttttttt ttgagaaaga    5160 gtttcactct tgttgcccag gctggagtgc aatggtgcga tctcagctca ctgcaacctc    5220
tgcctcccag gttcaagcga ttctcttacc tcagcctccc aagtggctgc atgcagtttc    5280
tagggcctaa taaacaggca tagctggaaa acaaaaacgg attttgagag cgatctattt    5340
gcctctaatt cctggggttc catgaggaaa acagaggttt ctcccaaaat ggaatccatg    5400
gtgccttttc tgttttttacc aagcagccct atgccatcag aaattatctt agggcctctc    5460
atgtgcgcat taacactggc aagacaaggt ggagaaaagt aattcagtca actgagaaaa    5520
```

| | |
|---|---|
| aaatctttt ccagcaaaac aagatccaag aagagaaaaa cataaaggcc tttcaaatat | 5580 |
| acgtatagct tggatatcca ctttaatta agctgagctc tctttaagaa agtccttta | 5640 |
| aatcccacat tacctgactt cagccatgcc aagcagccaa tatttctggc tttggaagtt | 5700 |
| tatcaaaaga acctcaaggt tcaaccaaca agcctcaatt aagacacgcg aagcacacca | 5760 |
| gattggctac accttaagac cagcctcata aaacctttt cactaatgga aactttacag | 5820 |
| ggaatatcaa cagtgatcct tatcattctt ttcaccagtt tacacaggga gagagaggcc | 5880 |
| aaaagtctga ctggttaaaa aactttatc cttttgctgg catgtcatgc ttctgggttc | 5940 |
| ccttccctg agctcaattc taagccaacc agtttaaggt ttgggaaatt aactttctc | 6000 |
| agtttggagg atgcatccta tgggaatgtc ctttagtaca gggacacagt cacccatctg | 6060 |
| tgaagagagg acaaaggagg aaaaagtaaa aaaagatttt tttcaaaggc tccccagggg | 6120 |
| ttcaggatgc atttgaaagg gggacagatt gaagatgaat ggctactcat ctagaaagag | 6180 |
| gggagccaga catccctggt tccttttctct ttctaggaaa tagccagggt atgtgaggga | 6240 |
| aagaaggaac aagcatccat tttccttctt ccgtccttat gtcccaagt cctgacaacc | 6300 |
| tcgacagggt gccacccatg ggtgccaata cggttctcac ccatggtaac aggggaccta | 6360 |
| gtggatggga ttatccactg ttacccacaa actgtctttc ccctgctct caatagcctt | 6420 |
| caagtgccct agacctcatt taggccattg atactagtat gacctttatc catgaaacaa | 6480 |
| gaggcttggc ttaattgtca ggaattagtc atgctcacct atactgtgct ttttaattt | 6540 |
| tgttgttgtc tgcctctgga tccctccgat gcagttatct ttcctagggc ttctacatga | 6600 |
| agcttggaat tgagtttggg acaaaagaac tgcctcagta ggtgggtgca tggactcatc | 6660 |
| aatccccagg tgtccctcac cagtctggct gctgccgcct tatcataagc tgaaggctaa | 6720 |
| ggtgcaactg tgaaattagg tccttctcaa acaagggagg gaaatggtg tcctgtgaat | 6780 |
| tagggtcctg gtctaataag atgccttcca aaaggaagaa aacttctggc acagagaaga | 6840 |
| cccctctacc cgcagggctg tgttattagg ttggtgcgaa agcaattgtg gtgcccatca | 6900 |
| ttctaagtaa tgacaaaaac cacaactact ttcacaccag cctactaact catgacttgg | 6960 |
| tggacaaaag aaaataacaa caacaacaac agcttaaatg cagggctgtg tttactgctg | 7020 |
| acaaggtg | 7028 |

<210> SEQ ID NO 16
<211> LENGTH: 1656
<212> TYPE: DNA
<213> ORGANISM: Homo sapiens
<220> FEATURE:
<221> NAME/KEY: allele
<222> LOCATION: (1001)..(1001)
<223> OTHER INFORMATION: r = a or g

<400> SEQUENCE: 16

| | |
|---|---|
| gggtatatac ccaaaggaaa taaagtcatt acctcgtgaa gatatctgta ttcctatgtt | 60 |
| aactgcagca ttattgacaa tagccaagat atggaaacaa actagatgtc cttcaatgga | 120 |
| taaactatga tatgtacata caatggaata ttattcagcc tttaaaaaga ggaaaatgag | 180 |
| gaaatcttgc tatttccac aacatggatt gacctggagg acattatact aggagaaata | 240 |
| agccagagac aaaagaaaa atattgtata atttcactta tatgtggtat tcttcccaaa | 300 |
| agatcaaata tatagagaga atgaaacagg gttaccagtg ctggagtctg ggaggggaga | 360 |
| atggggagat ctaggtaaaa ggttacaaag tagcaaatat atagaataaa caagtcaaaa | 420 |
| aatgtgttgt acagcaacat gtggattaaa attaataata gtgttatata caggattttt | 480 |

-continued

| | | |
|---|---|---|
| tctaaactaa gtatattata gctgtttgcc acaaggagaa acatggtata ttagctcatt | 540 | |
| ttgcattgct gtaaaggaat acctgagatt aggtaattta taaagaaaag agattgattt | 600 | |
| ggctcaccgt tctacaaacc gtacaagagg ctcatggttc cacaaaccgt gcagcttctg | 660 | |
| cttctggtga agacttcagg aagctttcaa tcatggtgga aggtgaaggg aagcaggtgt | 720 | |
| gtcgcatggt gaagggaagc aggtgtgttg catgatgaag gtgggagcga gggcaagggg | 780 | |
| tgaggtccca ggatgtttaa gaaccagctt tcatgtgaac aaacagagca agaacccatt | 840 | |
| cattactgca agagggcag caagccattc atgaaacatc cacccccagg actcaaacac | 900 | |
| ctcccaccaa gcctcacctc cagcactggg gatcacattt caacatgagg tttggagggg | 960 | |
| acaaactata tcaaatggta actgagaaga ttaataaatt rttccactat agtaaccatt | 1020 | |
| ttactacaca catgcatctt ataacatcac gttttatacc ttaaatatac acaatacaat | 1080 | |
| ttttttttaa aaaagctagt tagatatgga atttaccaat gagtgaatgt tttccagtaa | 1140 | |
| ttgtgtagac ttcagagctc tttctggcga gtacatatgg cctccaactt aataaggttc | 1200 | |
| gacttaaggt tttttgactt acgatggatt catcaggatg taacctcaca ataagctgag | 1260 | |
| gagcatccat atgtacctcc attcatgctg gataaatgga ttcttttttt tttttttttt | 1320 | |
| tttttttttg agacacagtc ttgctctgtc actaggctgg agtgcagtgg catgatcttg | 1380 | |
| gctcattgca gcctccgcct cccggattca agcaattctc ctgcctcagc ctcccgagca | 1440 | |
| gctgggatta gaggtgcatg ccaccacacc agctaatttt tgtattttta gtagagacgg | 1500 | |
| ggttttgcca cgttggcccg gatggtctca atctcttgac ctcgtgatcc gcccgcctcg | 1560 | |
| gcctcccaaa gtgctgagat tacaggcatg agccaccgcg cctggccaac aaataggctc | 1620 | |
| tttaaggcac tgctcttctt tgtccctgag agcaga | 1656 | |

<210> SEQ ID NO 17
<211> LENGTH: 936
<212> TYPE: DNA
<213> ORGANISM: Homo sapiens
<220> FEATURE:
<221> NAME/KEY: allele
<222> LOCATION: (436)..(436)
<223> OTHER INFORMATION: y = c or t

<400> SEQUENCE: 17

| | | |
|---|---|---|
| tgagtgtcac ttcctaggta ttgtttcttc tccctggctg gtggtcaagt ccagaagtcc | 60 | |
| tgtcccagaa tttcttcaaa aggagagagg gagtaaaatt gggtatggaa aaaagactca | 120 | |
| cattgacaaa aaagaatttt agagtcttct ctaaaatgtt gcggcaagta gataaaacca | 180 | |
| tgaaaaacca ggatgcccta tgtgattgtt aatattaagt gtcaacttga ttggattgaa | 240 | |
| ggatgcaaag tattattcct gaatgtgtct atgaggatgt tgccaataga gattaatatt | 300 | |
| tgagtcagtg actgggagag gcagacccac cctctatctc agtgggcacc atctgagcag | 360 | |
| ctgccagcgc agctagagta aagcaggtag aagaagatgg aaagaacaga cctgccgagt | 420 | |
| cttctggcct ccaccyttct cccttgctgg atgcttcctg ccctcgaata tcagactcca | 480 | |
| agttcttcag cttttggact cctgcactta catcagtggc ttaccagggg ttctcaggcc | 540 | |
| ttcagccaca gactgaaggc tgcactgtca cttttcgagg ttttgagactc ggactggctt | 600 | |
| ccctgctcct cagtttgcac acggcctatt gtgggacttc actttgtgat tgtgtgagtc | 660 | |
| aatactcctt aataaactcc ctttcatata tacatctatc ctattagtcc tgtccctcag | 720 | |
| gaaaccctga ctaatacacc ctataggcag atgagcctat tttacctggg gttagatcaa | 780 | |

```
agttgtttga gggaaggggc aacagaagag agctaacttc tcatgtgcca atgagaccga    840
aggaaagatt ctaatggaca cacaagatgc aatacagaaa tctggagaaa tggttcaata    900
gggaacacac agctcctagt gaggattaag cacccc                              936
```

<210> SEQ ID NO 18
<211> LENGTH: 938
<212> TYPE: DNA
<213> ORGANISM: Homo sapiens
<220> FEATURE:
<221> NAME/KEY: allele
<222> LOCATION: (363)..(363)
<223> OTHER INFORMATION: s = c or g

<400> SEQUENCE: 18

```
tgggggtgct taatcctcac taggagctgt gtgttcccta ttgaaccatt tctccagatt     60
tctgtattgc atcttgtgtg tccattagaa tctttccttc ggtctcattg gcacatgaga    120
agttagctct cttctgttgc cccttccctc aaacaacttt gatctaaccc caggtaaaat    180
aggctcatct gcctataggg tgtattagtc agggtttcct gagggacagg actaatagga    240
tagatgtata tatgaaaggg agtttattaa ggagtattga ctcacacaat cacaaagtga    300
agtcccacaa taggccgtgt gcaaactgag gagcagggaa gccagtccga gtctcaaaac    360
ctsgaaagtg acagtgcagc cttcagtctg tggctgaagg cctgagaacc cctggtaagc    420
cactgatgta agtgcaggag tccaaaagct gaagaacttg gagtctgata ttcgagggca    480
ggaagcatcc agcaagggag aaaggtggag gccagaagac tcggcaggtc tgttctttcc    540
atcttcttct acctgcttta ctctagctgc gctggcagct gctcagatgg tgcccactga    600
gatagagggt gggtctgcct ctcccagtca ctgactcaaa tattaatctc tattggcaac    660
atcctcatag acacattcag gaataatact ttgcatcctt caatccaatc aagttgacac    720
ttaatattaa caatcacata gggcatcctg ttttttcatg gttttatcta cttgccgcaa    780
cattttagag aagactctaa aattcttttt tgtcaatgtg agtctttttt ccatacccaa    840
ttttactccc tctctccttt tgaagaaatt ctgggacagg acttctggac ttgaccacca    900
gccagggaga agaaacaata cctaggaagt gacactca                            938
```

<210> SEQ ID NO 19
<211> LENGTH: 1239
<212> TYPE: DNA
<213> ORGANISM: Homo sapiens
<220> FEATURE:
<221> NAME/KEY: allele
<222> LOCATION: (458)..(458)
<223> OTHER INFORMATION: r = a or g

<400> SEQUENCE: 19

```
tctctgctgt ggcaccagga ctgcacgaga tctggtctct gcacatcttg gtgtctgcat     60
cctggtaaaa aatggcccccc tttcccacac ctacccatgg aggaagatga ggcagcaagt    120
tgtaagaaat taccagaaaa gcctcactcc tgatctcctg acccacccccc tcatgctctc    180 agtgcttcta ctcttgcttc attaatttat ccaacaaata ctaattgtcg gctaggtacc    240
aagttctgtt atagataatg aagatatggc tgtggaaaaa gaaccagaaa cctgcccttta    300 cattctagtg gaagaggagg aagataaaca ataaacaagg tcaacaagta actacagcat    360
gtcaggtgat ttaagtgctg ggaaggaaac tgagtggtat agatcattgc agagggtagg    420
ttgcaatttt aaatggaata gtgaagttag cctcactrat aaggcagtct tccagcaaag    480
atctgacaga ggtgaggaag tgaatctatg gaaacctggg ggtacagcct tccagcaaat    540
```

```
aacaggtgca aaggcccaga agcctagggc atttgtattt gagggcaagc aagggg tctg      600 tgtgctggag aagagtgagg aaggtgagaa ttagggagtg aggcctggga gattatgagg       660
aaaggaaaca gatcatacag cgccttggag gccattataa agactttggt ttttacccctt     720 atgagatggg aagctattgg cggttttaga gcaggaaagt gacatgatct gatttatgtt      780
ccaaggctca tgctggccac cttgttaaga caaaactgga gggaggcaag cagagcgggg      840
acaccaatga ggtaaccata gtgaccatcc agaggagaaa tgatggtggc ctggaatagg      900
tagttctgag aagtgttgta ttttggaggt agatcaatag aatttattgg tgcattgaat      960
atatatgatg tgaaagaaag cggggagaca agataaccct caacgcttt ggcctgagca      1020 gctgtaagac tgggattgca tttgatcaca gggcaagctc agtcgggctc aaaactgttt     1080
gctccttcct ggctggaact tcgtgtgggc ctaagatgtt taactggaat tcatctggc      1140 agacttaaac attgtgttct tcttttaaaa gctcaaataa caaatattcc aaaatgtaaa    1200
gcaaaaaaag gatttattga aatcatgtga caatatatc                             1239
```

<210> SEQ ID NO 20
<211> LENGTH: 801
<212> TYPE: DNA
<213> ORGANISM: Homo sapiens
<220> FEATURE:
<221> NAME/KEY: allele
<222> LOCATION: (401)..(401)
<223> OTHER INFORMATION: r = a or g

<400> SEQUENCE: 20

```
aaatatttaa taataataaa tatataaaaa gtatattcat ataaaataga aatgtatgaa       60
aaatattcac ctttatagaa gttttaaatt gtcaaagcaa tgtcaattta attggctcaa     120
taagagagtg aaaaaccatt gcttcaggac cgcctcagtc tgtaatgcta ttttaaaaaa     180
attatttcaa cattttctta aatactattc cttggttgtt aaattttat tttgctgtat      240 tagaagaatg aaggttgtta ttagggatgt tacattcaga aataaagttc tgaatttcat    300
agaacacttt attctctgcc tcatctttac atttcaattt ttcgggggga atgtcgttca     360
aatatagttt acaaatgaaa tataaaggat aaaagaatgg rtaaacaaag aagtccccaa    420
ggtgtaacag tgaatattgc tttaagaaaa tacaaaaaca attttaaata agatccttca    480
aacacgagtc atcctgttct cagggagctt tagaatttcc acattgctga atgccaaatt    540
ccacaagtca tggaattcc acacatctct cttcacttct ctgacttctt ctgtctaaca     600
tgggctgata tatttcagcc actacacagt agctggagtg tggtgttaga gcttcaatt t    660 caaccgctct gtgagcccct tcataaacct tttgctccta cacacgagag agaaaataat   720
cagttggtaa atgctgcca ttaagtcaca gctgcatttt tgtttaaatt aacaagttgt      780
acatggtcac agcagtagat g                                                  801
```

<210> SEQ ID NO 21
<211> LENGTH: 1715
<212> TYPE: DNA
<213> ORGANISM: Homo sapiens
<220> FEATURE:
<221> NAME/KEY: allele
<222> LOCATION: (219)..(219)
<223> OTHER INFORMATION: y = c or t

<400> SEQUENCE: 21

```
tcctatatag agatgaggaa ggcgccacaa gcaagacact cttggccaga aggattgagt       60
```

-continued

| | |
|---|---|
| aatgaggttt cctttcttct tgtcactaa aaaaattaca tttaattttg agaataaaga | 120 |
| taagttcttc taagacagga ttaaaaacta aacaaaacaa aaacaaacag aaaagaaaag | 180 |
| cttaatatat cttttaaatg agggacaatt gtacagagya gacttccttg ttgttgatag | 240 |
| ttttaattca gatatcaatc cagaaatcat aagattttt tccccaaaac ctgttcttat | 300 |
| ttacataaag tagactttaa aacaaaattt tgattcatta agtagaaata tttaataata | 360 |
| ataaatatat aaaaagtata ttcatataaa atagaaatgt atgaaaaata ttcacccttta | 420 |
| tagaagtttt aaattgtcaa agcaatgtca atttaattgg ctcaataaga gagtgaaaaa | 480 |
| ccattgcttc aggaccgcct cagtctgtaa tgctatttta aaaaaattat ttcaacattt | 540 |
| tcttaaatac tattccttgg ttgttaaatt tttattttgc tgtattagaa gaatgaaggt | 600 |
| tgttattagg gatgttacat tcagaaataa agttctgaat ttcatagaac actttattct | 660 |
| ctgcctcatc tttacatttc aatttttcgg ggggaatgtc gttcaaatat agttacaaa | 720 |
| tgaaatataa aggataaaag aatggataaa caaagaagtc cccaaggtgt aacagtgaat | 780 |
| attgctttaa gaaaatacaa aaacaattt aaataagatc cttcaaacac gagtcatcct | 840 |
| gttctcaggg agcttttagaa tttccacatt gctgaatgcc aaattccaca agtcatggaa | 900 |
| tttccacaca tctctcttca cttctctgac ttccttctgtc taacatgggc tgatatattt | 960 |
| cagccactac acagtagctg gagtgtggtg ttagagcttc aatttcaacc gctctgtgag | 1020 |
| ccccttcata aaccttttgc tcctacacac gagagagaaa ataatcagtt ggtaaatggc | 1080 |
| tgccattaag tcacagctgc attttgttt aaattaacaa gttgtacatg gtcacagcag | 1140 |
| tagatgggtt gtgggtttc ttcccagaca catccttctt ttctagagtc ctaggccata | 1200 |
| gcctggtaaa gggacaaggc aagtggctgt gtaggtgcaa cttgacttct ccttgagggc | 1260 |
| tgttggctgg ttgaccccat ggtcagagtc ttgttttaa gaattttgtt tgttttttga | 1320 |
| gatacagttt cactccatca tccagcctgg agtgcagtgt caccatctcg gctcactgca | 1380 |
| acctctgcct ctcaggttca agagattctc gtgcctcagc ctcctgagta gctgggattg | 1440 |
| cagacgcata ccaccacgcc tggctaattt ttgtatttc agtagagatg gagtttcacc | 1500 |
| atgttgacca ggcaggtctt gaactcctga cctcaaatga tttgcctgcc tcagcctccc | 1560 |
| aaagtgctgg gattacaggc atgaaccacc ccacctggcc ttcttttaa gaatttgaag | 1620 |
| tgtgcagtga gaatgatgtg cagcgagatg agcagagata actgcaggca tgaaactgtg | 1680 |
| gccacataga gacagaaagt ctgagagaca gagca | 1715 |

<210> SEQ ID NO 22
<211> LENGTH: 1231
<212> TYPE: DNA
<213> ORGANISM: Homo sapiens
<220> FEATURE:
<221> NAME/KEY: allele
<222> LOCATION: (201)..(201)
<223> OTHER INFORMATION: y = c or t

<400> SEQUENCE: 22

| | |
|---|---|
| agctgcggac atcacagggc tcctggctta tgatctgtga tgctagattt tgcaattgat | 60 |
| tgcaaaatca gttttgcaat cagttgcaag tttcttgacc cattcactgg attgtgattg | 120 |
| tgttacaaga ccaagtcaag attatttgac ctcatagcac tttactcttt aacagctctc | 180 |
| tccttgaaat attaccttcc ygcactattc atgaacatat cagcccacag atttcctcct | 240 |
| acctctttgg ctattccttc tcagtctcct tttaagattt ttcttactca ggcatctttg | 300 |
| ggtgaaagtc cctcaatatc tggtcttact caaaactgcc tctcactcac tactctctcc | 360 |

```
ctaggcaatc ctatcaatgt ccactgtact gtatgcatga aatgactcac aaattttgt      420 ctctaataaa gactttactt tgagtcttgg atctgaagag atatgtcccc tggatctctt      480
aaaagcatat taagcttaac atattcaaaa ccaaactcat aatctctatt accttgcatc      540
ccaccaaact ggtctttttc atcaaacccc atcaaaaga tctcagcaat tcatctaatt       600
atgcatgcaa gaaacttaga ggtcatcttt gacatgtcct cttcaccatt atatccgatc      660
tatcacctgg tcctgccaat gttgcttact aaatgtccct ccaggaataa attttctcta      720 gtcctttca taagccaaat tcggtctcct gtagactatt attagtaacc tgctacttca       780
cttatctgca tccaacctgt tccccaaaat atagtcaaaa tgatcttttc tatacacaag      840
tctgatcata tggctcctaa ataaaattat gttttttctgg aggaagtcac aactccttaa     900
aaaattcttg tacctgccta cctttccagt cccatctcat tatggactcc ttcctgcatg      960
ctcttcttca atatattggt tatctttcag tcccttgagt ttgctatgcc agagggcctt     1020
tgcaaatgct ggtcccttgc ttgaaatgct ctattctttg cctcaagtga tcctcctacc    1080
tcggcctccc aaagtgctgg gattacaggc atggagccaa cacacctggc cttcacatct    1140 attttttaatc caagtaattc tagggtcaaa taatactgaa atctcgctaa gtatcaaacg    1200 ctgctttttaa ctgaagaaag tttactttgt t                                   1231

<210> SEQ ID NO 23
<211> LENGTH: 511
<212> TYPE: DNA
<213> ORGANISM: Homo sapiens
<220> FEATURE:
<221> NAME/KEY: allele
<222> LOCATION: (256)..(256)
<223> OTHER INFORMATION: y = c or t

<400> SEQUENCE: 23
tttcaacatg aattttggtg gagacaaact caaaccatag cagcttggga gtcctcttta      60
ggaaaagatt tataaatata aaatccttgc attggggtcc tgaagtttaa tcttcattag     120
attcatggta aaacagtttc taatcttctt agtactttgg accacaaata ggtccacttt    180
tgacctattt atactactcc aggggaagca taaaaagagt accaatcttt actttctgca    240
tgctgaaagt atctcyagca atgcacaaat ctacttttgt aatggagaaa ccttcattgt    300
aaagatttgt acattttaca atcgctacat aaaatatgta gagagaagtc gtagcggtta    360
aagatggaga tgcttctggg gatattcctt ccgaaattaa ttagcaggaa aatctgacct    420
aggacctacc ccatgctgga gagacatgga tgaatttatg ggataaaaat tgctactttg    480
gccatagctg catttgattt cctgaatttc t                                    511

<210> SEQ ID NO 24
<211> LENGTH: 701
<212> TYPE: DNA
<213> ORGANISM: Homo sapiens
<220> FEATURE:
<221> NAME/KEY: allele
<222> LOCATION: (201)..(201)
<223> OTHER INFORMATION: r = a or g

<400> SEQUENCE: 24
tcatgctaat gaggaaaact gcccaagacc ctgctggggg gtagtgtttc tgagactaat       60
catggcatgg catgggataa ttttgcactg gcatgacttg tgctttcttc ctcaaatcag     120
gcaacatagg tggtacaacc ttgcttgcct ttagttgcat ggaggcaaga gaattttggc     180
```

| | |
|---|---|
| aaaatttttac ttagggttca rggttttttta taagggataa gaagttgggc agaaggagga | 240 |
| gtcaagaagc atatctttt tttttggatg gagtttcact cttgtcgccc tggctggagt | 300 |
| gcagtggcgt gatctcagct cactgcaacc tctgcctccc ggattcaagc gattctcctg | 360 |
| cctcagcctc ctgagtagct gggattacag gtgcccgcca ccatgcctgg ctaattttt | 420 |
| tgtatttta gtagagatgg ggttttgcca tgttgggcag gctggtctcg aactcctgac | 480 |
| ctcaagtgat ccgcccacct cggcctccca aagtgctggg attacaggcg tgagccactg | 540 |
| cacccggcca ggaagcatat cttctgtttt ctccctgacc tcatcttctg tcaccccgac | 600 |
| ccctgtgttt gcagtgttga ctccttcact tgctccacca tgactccagt gactctgcct | 660 |
| tagggcctct gcactggccc ttcccttttc ctggtctgct c | 701 |

<210> SEQ ID NO 25
<211> LENGTH: 801
<212> TYPE: DNA
<213> ORGANISM: Homo sapiens
<220> FEATURE:
<221> NAME/KEY: allele
<222> LOCATION: (401)..(401)
<223> OTHER INFORMATION: y = c or t

<400> SEQUENCE: 25

| | |
|---|---|
| ttgttctgta tgaagtctct gcaccctcta gagagccttt tctttagtgg gaactcatta | 60 |
| agtacatgtg gggtcattca agctgcagat agacactaac cccatgcctg ctctgatcat | 120 |
| ttagtgacat caaaagctgc agcctttata aagttcaaaa aagcaccagt gccatttcca | 180 |
| acagatcctt gattggactc agatgacaaa gctatgagca attaaaaga aacaaagcac | 240 |
| ttacctgcta caccagtaag gaagaaactg atgaggaagc ctagaaagca atgtttaggc | 300 |
| atcatggttg caagtgtgac tgttcaggca accagtgttc cttttaacca gctcaggacc | 360 |
| aaagaggaaa ctgtaaaatc cacaaacaga caatcactcc ygggtttaag gcagatggtt | 420 |
| ccttgaagca actacaattt tattttgata ctacattata ttattttatt ttaggaaaaa | 480 |
| tatgaaagta taaaaatcac ttcaaaaaac atttgctgtc acttttatgt ggaagctcgt | 540 |
| tttattggga agctcgtttt tgttggggc ttcattagct gcagaaaggt aaaacactga | 600 |
| ggatgggcag atctgaaggg cagggcagtg cagggattgt gcaagtggca agcaggtgag | 660 |
| tgaatgaaac aactagtggg gccttaaggg aatctggccc caggaggcgg agaggctgcc | 720 |
| aaggactagg acttggctgc cagggtgatt ttgagtaatg tgcttggcat ttgcagctat | 780 |
| cggggcccct ggcagtggtt c | 801 |

<210> SEQ ID NO 26
<211> LENGTH: 2172
<212> TYPE: DNA
<213> ORGANISM: Homo sapiens
<220> FEATURE:
<221> NAME/KEY: allele
<222> LOCATION: (2033)..(2033)
<223> OTHER INFORMATION: y = c or t

<400> SEQUENCE: 26

| | |
|---|---|
| tgcctgatca gtcatcttta gaacataaac attccagaag ttttcaggag atgacaggca | 60 |
| caatttcctg aaggcctgcc tagaattgat ttgctaacat gaagatagat ggcttaatgc | 120 |
| ccttaatctc tctgtctatg gatttcttct ctcatttttg taacatcagt gctaccacca | 180 |
| ccaacagtaa taacactgca ccaggcactg agggactttt atctgcattc actcatttaa | 240 |
| tttgcccagc tcttctgtga ggaaggtact gtgcattatg gtcttcctct tacagactga | 300 |

```
aaaaacgaag ccttggacac ctgaaggaga ttgccaggca gccaatggtg aagctgattt    360
tgtacccaga cagtctgagt gcagagcctg ccattaccct ccaacagaaa accaagagca    420
aagccatggg agagaggagc taatgaaaga ggcagaccaa ttagaagctg aggctatact    480
ttatcttctt ccttcttccc tcctcctcct ccttctggcc ggcattcatc aaacattgaa    540
catatatgaa cattaactta tgttaggcac tatgttcaaa gctttacaac ttacttaatt    600
cccacagcca ccaagtaagg taaatatttt tattatcgca ttctacagat gaggaagctg    660
aggctttaga agttgcatc tcttactcga ggttacaggt ttggtaagat gcagagccag     720
gaacattttg gtagcatttg aattcctgcc gtattttgct aaatgtgccc ttgctgttac    780
caagtaccag agtcttctca aatccaaaca cttctggaag atgaaggctt gaattgcttt    840
tatgtattag tcactggaca actgcaccat cttggcaagt tacttaaatc acttacactg    900
agaggtaccc atttgttaac ttgcattctt acaggcttgc tcagaagtat gtggtgctga    960
taagatgctc tacactcctg cagtttcctc cacgaatacc agaagcaaat tctcacctgt   1020
tgtttgtggt ccctatcctg tgccaggcac ttctctaagc atttggcata tattaattga   1080
tttaatcttc acagtgacct agaatcccca ttctactaat gaggaaattg agggtgttaa   1140
gtaaatttcc caagttttcc tagatggtaa atggcagatc tgaaatccag accatgatag   1200
cttggcttag gagcctgtgc tggtaaccac catgatttag tgttccttca aggtaaaaga   1260
cattctaagg tgagtgagag ccagagagaa agagagaggg agagaaagaa agagggaggg   1320
agggaaggag agagagagag agaaatggat gtacatttgt tctgtatgaa gtctctgcac   1380
cctctagaga gcctttctt tagtgggaac tcattaagta catgtggggt cattcaagct    1440
gcagatagac actaaccccca tgcctgctct gatcatttag tgacatcaaa agctgcagcc   1500
tttataaagt tcaaaaaagc accagtgcca tttccaacag atccttgatt ggactcagat   1560
gacaaagcta tgagcaatta aaagaaaca aagcacttac ctgctacacc agtaaggaag    1620
aaactgatga ggaagcctag aaagcaatgt ttaggcatca tggttgcaag tgtgactgtt   1680
caggcaacca gtgttccttt taaccagctc aggaccaaag aggaaactgt aaaatccaca   1740
aacagacaat cactcccggg tttaaggcag atggttcctt gaagcaacta caatttttatt   1800 ttgatactac attatattat tttattttag gaaaaatatg aaagtataaa aatcacttca   1860
aaaaacattt gctgtcactt ttatgtggaa gctcgtttta ttgggaagct cgttttttgt   1920
tggggcttca ttagctgcag aaaggtaaaa cactgaggat gggcagatct gaagggcagg   1980
gcagtgcagg gattgtgcaa gtggcaagca ggtgagtgaa tgaaacaact agyggggcct   2040
taagggaatc tggccccagg aggcggagag gctgccaagg actaggactt ggctgccagg   2100
gtgattttga gtaatgtgct tggcatttgc agctatcggg gccctggca gtggttcaaa     2160 gcaagagggg tc                                                         2172
```

<210> SEQ ID NO 27
<211> LENGTH: 3078
<212> TYPE: DNA
<213> ORGANISM: Homo sapiens
<220> FEATURE:
<221> NAME/KEY: allele
<222> LOCATION: (1078)..(1078)
<223> OTHER INFORMATION: r = a or g

<400> SEQUENCE: 27

```
aaaaaagtca tgttccatag tgaacaggtc tgtgcaaacc taccctttaaa gtccaaggaa    60
```

```
gctgagaggt caaagaaaaa ggctgacata tccagtttct cagaaagaaa catttcgtag    120
ggacttatga acagagccat gtgtgtgtcc tggacagtgg caagacaaga tggtggaccc    180
tcatgccatt accctgtaga cctgaagaag gaattaagga aatcaactat aacctaatag    240
tagtagtagt aatagaaatt ttaaaatcct cttaaagttg ctgcaaagtg tgaccccca     300 ccttacactc aagttaaaag ggaatattaa cagcctgtct tctctctgtg gacagtggac    360
cttatctata cttcccaaat ccacattcct cagagtttat tacaggccca gtgagttcct    420
gcatgactgc agggtcacaa gactgataag tttaggttgc aagacatgtc tttctcaaaa    480
tataacaaat gttgtaatgc tgcctttgtt tcttgcttct gtatctcgct tcctgcctca    540
tgtagttccc accttaagat gtttaaacgt aggaaaagcc ctttgctcag ggctcagact    600
ttctggacat atgtgctact gatcacctta atttagtaaa ctctcctgaa cctttttcgg    660
tctctccaat cttttggttgt cccacaacat ttccggggac cagtctggga ttggagatgg    720
cagattttcg tctcctttgc ctgtgggtta gagccccagg acatgggaaa tctggggtcc    780
ttggtgccac cgggagagtt ttagcccaga aggaaacag cccttccacg ttctggagcc     840
ttcctccaac agtgcaaatg gaaccagtgg aaagggttgc aggacagtca caagaacagt    900
gcatagacat atgaactgca gtaaggtttg ggccctaagg caagacccgt cccataagga    960 tggaaggga gcctggtcac ctccaagggc atgacaacta gtctgacccg agggggttgg    1020
gacaatggga gaggcccatt gattcagatg aaactcacac cctaattgac accagacrta    1080 agtgggctc atgagtcggt cagaaaggaa aaccattttg gggatggggg aggtgtgtga    1140
aagtgtgtaa aagagatggt ctcgggagag accaaggcgg ggttgatgtg gggaggcaca    1200
gatctcttag cgtggactgt gtgctcccag gcgagtgtgg gaaaaccag acctaggaca    1260 ctgcatacgg cccagaggac cagctccaca gctgcagcta gctgtgacag gaattaaggc    1320
atgctcctgg ctaagcagtg tccgaacctc ctgtaatagg acccagtctg gtggatccaa    1380
gagtgaaagt gagagtgaaa gtgcatcaca agggaggaaa caggaggaaa agcgtcaaag    1440
cctattccac tggagtgcgt gctgaaaaac tttaaaaaaa gttttaatgg tgactatggg    1500
gttaagctaa cttcacagaa actgagaact ttttttgagat aaaatagcca tctttttaatg   1560 tagggtggcc agccaagggg acaatagaca gggagataat tggccgagtg tttcgggtgg    1620
tcaccaggct tggagaacag cccgggcacc tggatcagtt tccgtatatt gactcctggc    1680
taagtataat tcagaccctc cctaagtggc tgcaggccta ctttgagatc tactgtaaga    1740
ctctaacggc caagacaaaa ccaggaacaa tagaaagaaa ctgcaaggca tcagaaaaag    1800
aaaagtcaca ggaaaagcag taaaaacctg tcctacaggc cccgcctgaa gagttagaaa    1860
ttccacccca ctatgcacca atttatccac ctctggcaaa gcttagacag aaggctgccc    1920
cggctgcctc cggagactca gactcagaag gaagcacccc tcaggcaaca ccacgcagag    1980
aggagccaga gcccttgact gaaaagccaa gggaggaact ccagggtgat gaggtcggcc    2040
gccttaggtc ggtccgtgcc caagcaatgc agatgccact ctgagaaaca tggggacaaa    2100
tttatttgaa tgcacagaat gaagtccaag ggggagaaca gctcttcttt tatcagccct    2160
tctctactac tgatctctta aattggagac aacatactcc ctcctataga gagaagcctc    2220
aggctcttat agatctaatg cagtccattt tcctaactca caatcctacc tgggttgatt    2280
gtaaacattt ttttctgtca ttatttaata tggaagagca ccgtagagtt atacaagctg    2340
ctctccagtg gctggagaaa aatgcatctt caagcacagg agatatcagg cagtatacac    2400
aacaagcact cctgatagag gctgacccag gctgggaccc taaccaggct caagggctac    2460
```

```
aagtttgcag cagtattgag aggcactcct aaatggaata aacgctggag agaaaaaggc    2520
caccaatatc ggaaaggtct cagaggttcg ccagaagcca gataaaagtc ccggtgaatt    2580
ttatgagagg ctgtgcgagg cttaccagct ttacatgcca cttgacccag aggctgcggg    2640
taatcagtgt atggttaatg tggcatttgt aagccaggtg caagaagaca tcggaagtta    2700
gaagggtttg aaggtgtgaa tattacccag cttatccagg tggctactaa ggtgtttgta    2760
aatcagaagg aggaggccaa gagaaaagct agatgcagag ctaaggaaaa ggcagacttg    2820
ctggcggtgg ccttagttgg aagagaaact ggttttgtga gaggatgtgg tcgtggttgc    2880
ggtcatgata gaggacaaac taggtaaaac caggaagcta agccaggaca gagggccaa     2940 cttaggctta agggagatca atgtgtgaga tgcaagcaga tgggacacta aagaatgaa     3000 tgccaaattt tccggtgccc ttgttaggaa gagatttcct ccagaaattg caagcacaaa    3060
tctcctttat accagaag                                                  3078
```

<210> SEQ ID NO 28
<211> LENGTH: 3164
<212> TYPE: DNA
<213> ORGANISM: Homo sapiens
<220> FEATURE:
<221> NAME/KEY: allele
<222> LOCATION: (1164)..(1164)
<223> OTHER INFORMATION: r = a or g

<400> SEQUENCE: 28

```
aaaaaagtca tgttccatag tgaacaggtc tgtgcaaacc tacccttaaa gtccaaggaa      60
gctgagaggt caaagaaaaa ggctgacata tccagtttct cagaaagaaa catttcgtag     120
ggacttatga acagagccat gtgtgtgtcc tggacagtgg caagacaaga tggtggaccc     180
tcatgccatt accctgtaga cctgaagaag gaattaagga aatcaactat aacctaatag     240
tagtagtagt aatagaaatt ttaaaatcct cttaaagttg ctgcaaagtg tgacccccca     300
ccttacactc aagttaaaag ggaatattaa cagcctgtct tctctctgtg acagtggac      360 cttatctata cttcccaaat ccacattcct cagagtttat tacaggccca gtgagttcct     420
gcatgactgc agggtcacaa gactgataag tttaggttgc aagacatgtc tttctcaaaa     480
tataacaaat gttgtaatgc tgcctttgtt tcttgcttct gtatctcgct tcctgcctca     540
tgtagttccc accttaagat gtttaaacgt aggaaaagcc ctttgctcag ggctcagact     600
ttctggacat atgtgctact gatcaccta atttagtaaa ctctcctgaa cctttttcgg      660
tctctccaat ctttggttgt cccacaacat ttccggggac cagtctggga ttggagatgg     720
cagattttcg tctcctttgc ctgtgggtta gagccccagg acatgggaaa tctggggtcc     780
ttggtgccac cggagagtt ttagcccaga aggagaacag cccttccacg ttctggagcc      840
ttcctccaac agtgcaaatg gaaccagtgg aaagggttgc aggacagtca caagaacagt     900
gcatagacat atgaactgca gtaaggtttg ggccctaagg caagacccgt cccataagga     960
tggaagggga gcctggtcac ctccaagggc atgacaacta gtctgacccg aggggggttgg   1020 gacaatggga gaggcccatt gattcagatg aaactcacac cctaattgac accagacgta    1080 agtgggggctc atgagtcggt cagaaaggaa accattttg gggatggggg aggtgtgtga    1140
aagtgtgtaa aagagatggt ctcrggagag accaaggcgg ggttgatgtg gggaggcaca    1200
gatctcttag cgtggactgt gtgctcccag gcgagtgtgg gaaaaaccag acctaggaca    1260
ctgcatacgg cccagaggac cagctccaca gctgcagcta gctgtgacag gaattaaggc    1320
```

```
atgctcctgg ctaagcagtg tccgaacctc ctgtaatagg acccagtctg gtggatccaa    1380
gagtgaaagt gagagtgaaa gtgcatcaca agggaggaaa caggaggaaa agcgtcaaag    1440
cctattccac tggagtgcgt gctgaaaaac tttaaaaaaa gttttaatgg tgactatggg    1500
gttaagctaa cttcacagaa actgagaact tttttgagat aaaatagcca tcttttaatg    1560
tagggtggcc agccaagggg acaatagaca gggagataat tggccgagtg tttcgggtgg    1620
tcaccaggct tggagaacag cccgggcacc tggatcagtt ccgtatatt  gactcctggc    1680
taagtataat tcagaccctc cctaagtggc tgcaggccta ctttgagatc tactgtaaga    1740
ctctaacggc caagacaaaa ccaggaacaa tagaaagaaa ctgcaaggca tcagaaaaag    1800
aaaagtcaca ggaaaagcag taaaaacctg tcctacaggc cccgcctgaa gagttagaaa    1860
ttccaccccca ctatgcacca atttatccac ctctggcaaa gcttagacag aaggctgccc    1920
cggctgcctc cggagactca gactcagaag gaagcacccc tcaggcaaca ccacgcagag    1980
aggagccaga gcccttgact gaaaagccaa gggaggaact ccagggtgat gaggtcggcc    2040
gccttaggtc ggtccgtgcc caagcaatgc agatgccact ctgagaaaca tggggacaaa    2100
tttatttgaa tgcacagaat gaagtccaag ggggagaaca gctcttcttt tatcagccct    2160
tctctactac tgatctctta aattggagac aacatactcc ctcctataga gagaagcctc    2220
aggctcttat agatctaatg cagtccattt tcctaactca caatcctacc tgggttgatt    2280
gtaaacattt ttttctgtca ttatttaata tggaagagca ccgtagagtt atacaagctg    2340
ctctccagtg gctggagaaa aatgcatctt caagcacagg agatatcagg cagtatacac    2400
aacaagcact cctgatagag gctgacccag gctgggaccc taaccaggct caagggctac    2460
aagtttgcag cagtattgag aggcactcct aaatggaata aacgctggag agaaaaaggc    2520
caccaatatc ggaaaggtct cagaggttcg ccagaagcca gataaaagtc ccggtgaatt    2580
ttatgagagg ctgtgcgagg cttaccagct ttacatgcca cttgacccag aggctgcggg    2640
taatcagtgt atggttaatg tggcatttgt aagccaggtg caagaagaca tcggaagtta    2700
gaagggtttg aaggtgtgaa tattacccag cttatccagg tggctactaa ggtgtttgta    2760
aatcagaagg aggaggccaa gagaaaagct agatgcagag ctaaggaaaa ggcagacttg    2820
ctggcggtgg ccttagttgg aagagaaact ggttttgtga gaggatgtgg tcgtggttgc    2880
ggtcatgata gaggacaaac taggtaaaac caggaagcta agccaggaca agagggccaa    2940
cttaggctta agggagatca atgtgtgaga tgcaagcaga tgggacacta aagaatgaa     3000
tgccaaattt tccggtgccc ttgttaggaa gagatttcct ccagaaattg caagcacaaa    3060
tctccttat  accagaaggg cacatgactc taaatctagg tcaaagaaaa gccatgataa    3120
agacccttac tgtcccaaca acagaggaat ggtaataatt tggg                    3164
```

```
<210> SEQ ID NO 29
<211> LENGTH: 1001
<212> TYPE: DNA
<213> ORGANISM: Homo sapiens
<220> FEATURE:
<221> NAME/KEY: allele
<222> LOCATION: (501)..(501)
<223> OTHER INFORMATION: s = c or g

<400> SEQUENCE: 29
```

```
gaaccggagg ctaccggtgc atgctagtgt ttgtctgcac tttctcaggg tgggttgagg      60
catttcccac caggacaaag aaagctcggg aagtaaccag aatcttacta aaggacatta    120
ttcctagatt tcgactgcct ctaactttag gatcagacaa tggcccagca tttgtggcag    180
```

```
aaatagtaca acagctaaca cagaggttaa aaatcaaatg aaaactgcat acagcttatc    240
acccatagag ttctggaaag ttgaaagaat aaaccggaca ctcaaacagc cgttaaaaaa    300
gttttgccat gaaactcatc taagatggga tcaggtgctg cccatggtcc ttctctgagt    360
caggtgcacc cctactaaat taactgggta ttcaccctat aagatagtgt ttggccgaca    420
ccctgatcat aactcagata aacggggatt taaaaaattg gggaattaac cttaagaagg    480
caaatgcaag ccttaggtga sgtctcgcag gaaatgcaag gatgggtaag agaaagaata    540
cctgttagcc tcacagatgc agtacaaccc ttctaacctg gagactctgt ctgggtcaaa    600
caatggaacc caaccacttt agggccttta tgggatagtc cccatattgt gatcttgtct    660
actcccactg ctgttaaagt tgcaggtatc ataccttggg ttcatcatag ccggctgaaa    720
ccagaagcag ccaccaccca ggaccagtgg acaagtcaac aaaacccaga ccactcaaca    780
tggctgatcc tgtggtgaaa ccaagccact gctgacaagg acaactgccc tgcttcaacc    840 acaccgagg ctggttggtc cacgcacggc tgaagcttga ggaaacatcg agccctgttc    900
tagtcacaca aatggaagct gactagtcta tgcatggctg aagcctgagg aagtcaatga    960
tacataagta aatgtagact aaatttacaa acatagttat a                      1001

<210> SEQ ID NO 30
<211> LENGTH: 701
<212> TYPE: DNA
<213> ORGANISM: Homo sapiens
<220> FEATURE:
<221> NAME/KEY: allele
<222> LOCATION: (201)..(201)
<223> OTHER INFORMATION: y = c or t

<400> SEQUENCE: 30
acctttgcaa aatcatgcaa tgttgcagtc agctcgtcag ttggataaat taatctgagt     60
gacctaggaa ttatctgctt cttaaggata catagatttc cctgagaaat catctgggtg    120
cttttggaat ttgggggcag aaaatacagg atagtattat ctgacaattt tctaattctt    180
ctatggtaat tagtgtgttt ygattttttt tttatctcat ctagattcag ttgctacaaa    240
gtatattttc tttagaagac tatccttttt attcatgcct ttaaatttat tggtacagag    300
ttgtgcaagt tattcccttta tgatttattt aattctcctt tttctgtgac ttcccttta    360 taattttctg ttttgagtaa tgattttccc cttgttttct tagtaaattg gctggatatt    420
tattttcaaa tttctttca aggaactaaa ttttgtagtt tgtattcta ctttaaaaaa    480 agtcatgtct catttttatc tccttttacct ttaaaaattc cttccttttg ttttttgttt    540
atttaatttg ttggatttt caaaaaacaa aaactcctga gtcagatatt tgttctgttt    600
gttttattct ttatttata ccaatacaaa ttttttacact aggaatttct ctgaaatgta    660
taagctccct cattggctct aaaatgtgat gttttctttt t                        701

<210> SEQ ID NO 31
<211> LENGTH: 501
<212> TYPE: DNA
<213> ORGANISM: Homo sapiens
<220> FEATURE:
<221> NAME/KEY: allele
<222> LOCATION: (251)..(251)
<223> OTHER INFORMATION: m = a or c

<400> SEQUENCE: 31
ctctcttttt gctttgattt ctgggaggtg gattagcatt tactattaga ttcactattt    60
```

| | |
|---|---|
| aatttactct ttaagaacaa agataaagtg tagccagaca actgcttagg agtgtatcag | 120 |
| tccaacaaga tgtacattga gctctaaaca aaatttaaaa atcttcatga gccttagaat | 180 |
| aagaaaaata cctttacat tttaaaacag tgacttaaat ttttttttt tttactgta | 240 |
| gcatatgagc mgccaccata actaacttat tttgtatttc tagcttcacc taaagctatt | 300 |
| tctggatgtg gctgctagtt tgtcaaagtt aaataaagcg tgacgcatat tgttcaaagg | 360 |
| caagcggaag atctaacgtt tcttttttgaa atataggaaa ctggagatat caggcaacag | 420 |
| tggaaaagca tgcactttgg agaaaggtga aacctgaatt caattctctc aaaatgtact | 480 |
| tcgagcttca tccatttgca t | 501 |

<210> SEQ ID NO 32
<211> LENGTH: 1486
<212> TYPE: DNA
<213> ORGANISM: Homo sapiens
<220> FEATURE:
<221> NAME/KEY: allele
<222> LOCATION: (731)..(731)
<223> OTHER INFORMATION: s = c or g

<400> SEQUENCE: 32

| | |
|---|---|
| tgtttctttc tctataatac ataaaataaa ttatattaat attctaggtt atatataata | 60 |
| acacatataa ataaatataa aattatatta tatatagaaa tatattttt atttttataa | 120 |
| gtacgtattt atttgtaaac tgtaaaacca taataaagga gtaaaactga catgaatata | 180 |
| agtgaaatgg agggggttgt gtagacaata tgtttagctg acaaatattt attgagcact | 240 |
| tgtcctatgc caggcactgt ctgaagttct gggaatacgc agggattaga caagttcttg | 300 |
| ttctcataga gctgatatcc tagtgtccgt ggcagggagg cagataataa actgacacat | 360 |
| cactattttg tcaggtggtg ctaagtgcca tggagacaca gtaggtgcag ggagggagaa | 420 |
| taatgggaag ataccattgc aggtagggggg tgaggaatag ccttgctgga cagggacata | 480 |
| tgaacaaagg tctgagttgg gtgaggcagg atgccacaca gacattggag gaggaaaatc | 540 |
| tgagcagggg gcacagcaaa gccccaaggc tgaggccaga tgaaggagca ggaggcaatg | 600 |
| tggctggaga ggagggagca aggggcagag tgttggtggt gaggtcaggg gcccagcagc | 660 |
| ctgatccagg ggacttgaac aggatggaag gactttgggt gcgttctgaa gaaggggaag | 720 |
| ccactggaag scattaagta gaaaaaattg gaagtgagag taattatatg tgaaagttgt | 780 |
| tagagtcaca atggagtgac gatgaggcag gacaggtagt caaggaagta agtgcagtta | 840 |
| acacaatgag ccccagtatt cgcattgtaa tccagctcat gcaagcacag ctatctcctg | 900 |
| cagggaatat ttcccataga cagcatttgc actttgattt tacctcttct caaacggacc | 960 |
| ctgttctcat gataatagta aaaaacacac ccctaggtgg agatttaaga tgctgatgaa | 1020 |
| ttatgagatg tatgaacaag catgtacagc tactgcacat gtgcacccag aggaccaccg | 1080 |
| aggacatgct tactagcaac accttttctc accctcttat gaataatcat gtaagagtcc | 1140 |
| cataaaagga tttctccagc aataatcagt gctgtccatt cagtggctca tgcctgtaac | 1200 |
| ccagcacttt gggaggccga ggtgggtgga tcacctgagg tcaggagttt gagaccagcc | 1260 |
| tggtcaacat ggtgaaacct cgtttctatt aaaaatacaa aaaagtagc caggtgtaat | 1320 |
| ggcacatgcc tgtaatccca gctacttggg aggctgaagc aggagaactg attgaacctg | 1380 |
| ggaggtggag gttgcagtga gtcatgactg tgccactgca ctccagccaa cagagtaaga | 1440 |
| ctctgttccc cctcggcccc ctgcaaaaaa aaataataac aatgat | 1486 |

```
<210> SEQ ID NO 33
<211> LENGTH: 4000
<212> TYPE: DNA
<213> ORGANISM: Homo sapiens
<220> FEATURE:
<221> NAME/KEY: allele
<222> LOCATION: (2000)..(2000)
<223> OTHER INFORMATION: r = a or g

<400> SEQUENCE: 33
```

| | | | | | |
|---|---|---|---|---|---|
| tttgttatgg | acttatagca | attatttata | caaaacataa | gaattgttct | gaaaaaatta | 60 |
| aaaaatatat | acctgcatgg | ctcataactg | gaaatattat | accaggaggc | tttgtcactt | 120 |
| ggtatcttta | tccttttact | tattattttc | ttttaattct | acaggaagca | gtaaattctt | 180 |
| tatggttgga | gtggatgaag | aggtgccatg | taatagctca | gaaggcaaag | tcccttgttt | 240 |
| taccagctgt | ttaggcatcc | atgtactcat | ccttgatttg | aagggtttga | gttaattcta | 300 |
| tccttccaaa | tcagccctta | caatctcacg | tgcccacctc | ttctgcaaca | gtctctgggc | 360 |
| ctagagggag | gacgcttgca | atacaggatt | ttttgcatgt | tcccagtggc | tccaccccat | 420 |
| tctcccagtg | cacatgcagg | cccttagtct | gaacccacgc | tacattgatt | tatttccctt | 480 |
| actgagcatg | tgttaaggga | tggaattttt | caccatgggc | atgtttaggc | aagccccctg | 540 |
| tacacaatgt | cctggatggc | atttggctgt | cttctgcctc | tatcattccc | ccatctaaaa | 600 |
| gagtacatct | aactgccatt | agaataagga | taagaagaaa | gacaaagacc | catcttaact | 660 |
| gctttctgct | gacagagggc | actgttttgg | aaagacagca | gttgggtctc | cctcagaggc | 720 |
| ctatctaagg | gtatctggta | aaagggacca | tcattgagg | ctctggttgc | ataactgttt | 780 |
| ggagtttgag | ggcctgaagg | cgagaagaga | caaaccaggt | tattagaaga | catgtaccaa | 840 |
| aatgaaatgg | gggaaggta | aggacagttc | aaaaatcctg | aggctgctga | catgcccaga | 900 |
| taactggtag | ctgtagttgt | gcctgctaag | atttgggtgc | atgggacttg | gctttggtta | 960 |
| gctcccgtag | tttattttcc | caaaaaagaa | acctctgggt | tatgggcacc | ctatttactc | 1020 |
| ccattatctg | gcaggatttg | taggataatt | gttcagaact | agaatactgt | tccagatttt | 1080 |
| tacattaccc | atgcctttg | tttcttctga | gctgcagcca | gagatcactg | gttagttcac | 1140 |
| aggaataagc | agggttaatt | taaatgtag | gcaaaaaact | taaaaacaac | taatgagtct | 1200 |
| agaatttaat | gacaaatgta | tgataagttt | tgaaacataa | tttctttctc | cccagtcctc | 1260 |
| attttgtta | aaaacaaatc | ataataggag | tgagttgttt | gtaaataaa | ctttagtctt | 1320 |
| acacttggtc | tgcttatttg | cacaaagtac | aacaagaata | attattttta | cataggcttt | 1380 |
| ttaaattggc | tttgatggaa | ctctgttcca | caaggaattt | cagataggac | ttcataaaaa | 1440 |
| tgagcccagc | catgggtttg | taccctctaa | tacctatgag | ttgggtgaat | tgctctcttc | 1500 |
| ttgaggtccc | aagaatatgc | ggttcctggc | cctgttagaa | agtgacattc | tttactcact | 1560 |
| acaggttagg | gaacctgtat | ggggactgtg | tagacaaagt | atgaggctgg | tttacccaag | 1620 |
| gggcttttat | tggctctgca | agttgagctt | gattccttaa | agggaaacat | acccttccag | 1680 |
| tcaaagttac | agttactggt | tggtaaagtt | aaagttacag | ctactggttg | ctaaagcaac | 1740 |
| cagtttctcc | aattgcatcc | tgttgcaaaa | gaaagtggat | tcttactgca | ctgatgcaaa | 1800 |
| taaccgtatt | gccctaagtt | aagaatactc | acagatagtt | tccaaattct | agaggaagca | 1860 |
| ggcagagaga | aaaaaaagtg | ctaaattttg | ttcataggag | tctgcattac | tcaattatta | 1920 |
| aagattgtgt | atagctcaaa | aaaaagatc | agcactgttt | taagctaaag | tttaaaaaag | 1980 |
| attacttcaa | ttttctattr | gttcagtctg | ttcagttaac | tcttgttctg | cttgatattt | 2040 |

| | |
|---|---|
| gtgaacattt cagctcttca tgagtcctgt acgttttcc attattccaa tgtcacaatc | 2100 |
| tccaaagtta tcagaaacct gcatttgaga gcacctgtta cgtttctata gctgattata | 2160 |
| aatcctattt gaagaagatc aaaacaaaac aatggtctgt gaatagcaaa atgtccatgg | 2220 |
| tagttacagt caaaaacaca attgacaaag aaattttgtt atctctgtgg cttataatca | 2280 |
| cctaacataa cacctttaat tgtgagtgat agcatatact tagatattag aattttagaa | 2340 |
| atcccataca gttttggagc atatattatt attcactaaa atataaccca aagaagatta | 2400 |
| aatatcattt tggcaatccc atgtacataa atttgtcagg taatcctatt tacctctctt | 2460 |
| ctggatgctc cagggatgct aggggtcagg aaagacaacc ttgaagctga catttgattt | 2520 |
| tgggaagccc attaaatatg ttagaggttt aaaacaatgt tatgaagtag aattccagat | 2580 |
| taccataaat tacttatttt gccaaaatga tgactcaaaa attttaaaac aagccaaaaa | 2640 |
| cttttactca tttagaggga agacttagat ttccaaagaa tttgtctcct gtcttcactt | 2700 |
| tcatttcctt ggcagtctat ctggaagaca aactgaaata tttaattatc ctttactatt | 2760 |
| acatgaaaat cttatacaag gggagagaaag ccaaatttta ccctcacatt agtttactat | 2820 |
| taatgtcaac cccaatttttt taatgaaacc ttatagacaa ttctatccaa tcttaaccag | 2880 |
| tttgatcatg aggtaagatt cctgtaagcc ttttataacc ttttacaaat tactaattta | 2940 |
| ctaatctgct aaagagcaga ttagggcttt aagaaaacct tgttgtgctt tcatttcaat | 3000 |
| gctcagtttg tagaaaaacc atataataga gttttggatt taatcaatgt tcacacacag | 3060 |
| aatttctttt gcaagattaa tttttagaaa cctcccacaa cttgtttaaa cctttagttt | 3120 |
| atcttatcta atttataata gtcctttaac cttaggcaaa aacttacatt tccatgcatt | 3180 |
| cttataatct ttgactaata acacatttta ctgttcttac ataccttgca tgtaaatcta | 3240 |
| ttttcagtgg tctcaattac atgttataat ggtacctctt agcacttttt aattttagtt | 3300 |
| taaaacctgg taagtcgttt taattacgca ctaggtgctg ataaagtttg attccttcca | 3360 |
| gcataattaa gggtgtggtt aattccatat gtccctgtgc cttaccaagt tgtaaagcag | 3420 |
| gcagattgaa cagttttcaa aggcaaaaga agccgtttac aaccttaaaa catttagcca | 3480 |
| cctagtgcct gacttgcata atttagacca gctatttaca ttttaagaac atttgcattt | 3540 |
| tatcaattat cttttaagact acttttattt ctcagagatt aaagtcacaa gaactaaaag | 3600 |
| gcattatagc ttttatcttt cctccaaaaa tatttgatct tagtgctgat ttttctttaa | 3660 |
| gccaattaat tagagctctt ttttataact acacagatgg agaagaagat tgagtgttat | 3720 |
| aagattttc atttgcccat ctcctaattg gattcttggt ctctgggtgg gacccttaa | 3780 |
| gagcagggct aagaaagcat gcagtttatt ttctttttt ctttttcttt tctttttttt | 3840 |
| tgagaaagag tttcactctt gttgcccagg ctggagtgca atggtgcgat ctcagctcac | 3900 |
| tgcaacctct gcctcccagg ttcaagcgat tctcttacct cagcctccca agtggctgca | 3960 |
| tgcagtttct agggcctaat aaacaggcat agctggaaaa | 4000 |

<210> SEQ ID NO 34
<211> LENGTH: 4000
<212> TYPE: DNA
<213> ORGANISM: Homo sapiens
<220> FEATURE:
<221> NAME/KEY: allele
<222> LOCATION: (2000)..(2000)
<223> OTHER INFORMATION: w = a or t

<400> SEQUENCE: 34

| | |
|---|---|
| cagctactgg ttgctaaagc aaccagtttc tccaattgca tcctgttgca aaagaaagtg | 60 |

```
gattcttact gcactgatgc aaataaccgt attgccctaa gttaagaata ctcacagata      120
gtttccaaat tctagaggaa gcaggcagag agaaaaaaaa gtgctaaatt ttgttcatag      180
gagtctgcat tactcaatta ttaaagattg tgtatagctc aaaaaaaaag atcagcactg      240
ttttaagcta aagtttaaaa aagattactt caattttcta ttagttcagt ctgttcagtt      300
aactcttgtt ctgcttgata tttgtgaaca tttcagctct tcatgagtcc tgtacgtttt      360
tccattattc caatgtcaca atctccaaag ttatcagaaa cctgcatttg agagcacctg      420
ttacgtttct atagctgatt ataaatccta tttgaagaag atcaaaacaa acaatggtc       480 tgtgaatagc aaaatgtcca tggtagttac agtcaaaaac acaattgaca agaaatttt       540 gttatctctg tggcttataa tcacctaaca taacacctt aattgtgagt gatagcatat       600
acttagatat tagaatttta gaatcccat acagttttgg agcatatatt attattcact        660
aaaatataac ccaaagaaga ttaaatatca ttttggcaat cccatgtaca taaatttgtc       720
aggtaatcct atttacctct cttctggatg ctccagggat gctaggggtc aggaaagaca      780
accttgaagc tgacatttga ttttgggaag cccattaaat atgttagagg tttaaaacaa      840
tgttatgaag tagaattcca gattaccata aattacttat tttgccaaaa tgatgactca      900
aaaattttaa aacaagccaa aaactttac tcatttagag ggaagactta gatttccaaa       960
gaatttgtct cctgtcttca ctttcatttc cttggcagtc tatctggaag acaaactgaa     1020
atatttaatt atcctttact attacatgaa aatcttatac aagggagaga aagccaaatt     1080
ttaccctcac attagtttac tattaatgtc aaccccaatt ttttaatgaa accttataga    1140
caattctatc caatcttaac cagtttgatc atgaggtaag attcctgtaa gccttttata     1200
accttttaca aattactaat ttactaatct gctaaagagc agattagggc tttaagaaaa     1260
ccttgttgtg ctttcatttc aatgctcagt ttgtagaaaa accatataat agagttttgg     1320
atttaatcaa tgttcacaca cagaatttct tttgcaagat taattttag aaacctccca     1380 caacttgttt aaacctttag tttatcttat ctaatttata atagtccttt aaccttaggc     1440
aaaaacttac atttccatgc attcttataa tctttgacta ataacacatt ttactgttct     1500 tacataccet gcatgtaaat ctattttcag tggtctcaat tacatgttat aatggtacct     1560
cttagcactt tttaatttta gtttaaaacc tggtaagtcg ttttaattac gcactaggtg     1620
ctgataaagt ttgattcctt ccagcataat taagggtgtg gttaattcca tatgtccctg     1680
tgccttacca agttgtaaag caggcagatt gaacagtttt caaaggcaaa agaagccgtt     1740
tacaacctta aacatttag ccacctagtg cctgacttgc ataattaga ccagctattt       1800 acatttaag aacatttgca ttttatcaat tatctttaag actactttta tttctcagag       1860
attaaagtca caagaactaa aaggcattat agctttatc tttcctccaa aaatatttga       1920
tcttagtgct gattttcctt taagccaatt aattagagct cttttttata actacacaga     1980
tggagaagaa gattgagtgw tataagattt ttcatttgcc catctcctaa ttggattctt     2040
ggtctctggg tgggacccctt taagagcagg gctaagaaag catgcagttt attttctttt   2100
tttctttttc ttttctttt ttttgagaaa gagtttcact cttgttgccc aggctggagt      2160
gcaatggtgc gatctcagct cactgcaacc tctgcctccc aggttcaagc gattctctta     2220
cctcagcctc ccaagtggct gcatgcagtt tctagggcct aataaacagg catagctgga     2280
aaacaaaaac ggattttgag agcgatctat ttgcctctaa ttcctggggt tccatgagga     2340
aaacagaggt ttctcccaaa atggaatcca tggtgccttt tctgttttta ccaagcagcc    2400
```

```
ctatgccatc agaaattatc ttagggcctc tcatgtgcgc attaacactg gcaagacaag    2460
gtggagaaaa gtaattcagt caactgagaa aaaaatcttt ttccagcaaa acaagatcca    2520
agaagagaaa aacataaagg cctttcaaat atacgtatag cttggatatc cacttttaat    2580
taagctgagc tctctttaag aaagtccttt taaatcccac attacctgac ttcagccatg    2640
ccaagcagcc aatatttctg gctttggaag tttatcaaaa gaacctcaag gttcaaccaa    2700
caagcctcaa ttaagacacg cgaagcacac cagattggct acaccttaag accagcctca    2760
taaaaccttt ttcactaatg gaaactttac agggaatatc aacagtgatc cttatcattc    2820
ttttcaccag tttacacagg gagagagagg ccaaaagtct gactggttaa aaaactttta    2880
tccttttgct ggcatgtcat gcttctgggt tcccttcccc tgagctcaat tctaagccaa    2940
ccagtttaag gtttgggaaa ttaacttttc tcagtttgga ggatgcatcc tatgggaatg    3000
tcctttagta cagggacaca gtcacccatc tgtgaagaga ggacaaagga ggaaaaagta    3060
aaaaaagatt tttttcaaag gctccccagg ggttcaggat gcatttgaaa ggggacaga    3120
ttgaagatga atggctactc atctagaaag aggggagcca gacatccctg gttcctttct    3180
ctttctagga aatagccagg gtatgtgagg gaaagaagga acaagcatcc attttccttc    3240
ttccgtcctt atgtccccaa gtcctgacaa cctcgacagg gtgccaccca tgggtgccaa    3300
tacggttctc acccatggta acaggggacc tagtggatgg gattatccac tgttacccac    3360
aaactgtctt tcccccctgct ctcaatagcc ttcaagtgcc ctagacctca tttaggccat    3420
tgatactagt atgaccttta tccatgaaac aagaggcttg gcttaattgt caggaattag    3480
tcatgctcac ctatactgtg cttttttaatt tttgttgttg tctgcctctg gatccctccg    3540
atgcagttat ctttcctagg gcttctacat gaagcttgga attgagtttg gacaaaaga    3600
actgcctcag taggtgggtg catggactca tcaatcccca ggtgtccctc accagtctgg    3660
ctgctgccgc cttatcataa gctgaaggct aaggtgcaac tgtgaaatta ggtccttctc    3720
aaacaaggga gggaaaatgg tgtcctgtga attagggtcc tggtctaata agatgccttc    3780
caaaaggaag aaaacttctg gcacagagaa gaccccctcta cccgcagggc tgtgttatta    3840
ggttggtgcg aaagcaattg tggtgcccat cattctaagt aatgacaaaa accacaacta    3900
cttttcacacc agcctactaa ctcatgactt ggtggacaaa agaaaataac aacaacaaca    3960
acagcttaaa tgcagggctg tgtttactgc tgacaaggtg                           4000
```

<210> SEQ ID NO 35
<211> LENGTH: 1191
<212> TYPE: DNA
<213> ORGANISM: Homo sapiens
<220> FEATURE:
<221> NAME/KEY: allele
<222> LOCATION: (819)..(819)
<223> OTHER INFORMATION: r = a or g

<400> SEQUENCE: 35

```
tgctagattt tgcaattgat tgcaaaatca gttttgcaat cagttgcaag tttcttgacc     60
cattcactgg attgtgattg tgttacaaga ccaagtcaag attatttgac ctcatagcac    120
tttactctt aacagctctc tccttgaaat attaccttcc cgcactattc atgaacatat    180
cagcccacag atttcctcct acctctttgg ctattccttc tcagtctcct tttaagattt    240
ttcttactca ggcatctttg ggtgaaagtc cctcaatatc tggtcttact caaaactgcc    300
tctcactcac tactctctcc ctaggcaatc ctatcaatgt ccactgtact gtatgcatga    360
aatgactcac aaattttgt ctctaataaa gactttactt tgagtcttgg atctgaagag    420
```

```
atatgtcccc tggatctctt aaaagcatat taagcttaac atattcaaaa ccaaactcat      480
aatctctatt accttgcatc ccaccaaact ggtcttttc atcaaacccc atcaaaaaga      540
tctcagcaat tcatctaatt atgcatgcaa gaaacttaga ggtcatcttt gacatgtcct      600
cttcaccatt atatccgatc tatcacctgg tcctgccaat gttgcttact aaatgtccct      660
ccaggaataa attttctcta gtccttttca taagccaaat tcggtctcct gtagactatt      720
attagtaacc tgctacttca cttatctgca tccaacctgt tccccaaaat atagtcaaaa      780
tgatcttttc tatacacaag tctgatcata tggctcctra ataaaattat gttttctgg       840
aggaagtcac aactccttaa aaaattcttg tacctgccta cctttccagt cccatctcat      900
tatggactcc ttcctgcatg ctcttcttca atatattggt tatctttcag tcccttgagt      960
ttgctatgcc agagggcctt tgcaaatgct ggtcccttgc ttgaaatgct ctattctttg     1020
cctcaagtga tcctcctacc tcggcctccc aaagtgctgg gattacaggc atggagccaa     1080
cacacctggc cttacatctc attttttaatc caagtaattc tagggtcaaa taatactgaa     1140
atctcgctaa gtatcaaacg ctgcttttaa ctgaagaaag tttactttgt t              1191
```

<210> SEQ ID NO 36
<211> LENGTH: 844
<212> TYPE: DNA
<213> ORGANISM: Homo sapiens
<220> FEATURE:
<221> NAME/KEY: allele
<222> LOCATION: (501)..(501)
<223> OTHER INFORMATION: y = c or t

<400> SEQUENCE: 36

```
atttcctcaa cagaaaattc ctgtaatcag tattttcatg aacttaaccc tcgtgtttgg       60
ggaaggacta ggcactatga caaattctgc tgtctaaaaa tactttttta ggggctgggc      120
atggtggctc acacccataa tcccagcact ttgggaggcc aaaggggggca gatcacctga     180
ggtcaggagt ttgaaaccag cctggccaat atgatgaaac cccgtctcta ctaaaaatac      240
aaaaattagc caaggtggt ggcacacact tgtaatccta gctactcggg aggcagaggc       300
cggagaatcg cttgaacccg ggatgcagag gttgcagtga gccaagatcg tgccactgca     360
ctccagcctg ggtgacaaag cgagaccctg tcacacacaa acacacacac acacacacac     420
acacaaggtg acaaattgat ggagtggagg ctctgcagtc agatatagca aatttgaacc     480
ctgacttgga taatacagat ygcgagattg gagcaatgac taaagcctct acatcttgat     540
gttctggact agaaaattag gataataaaa gctatctcct agagttgttc tgacaattag     600
accaaaagag ataatgatgt agagacctca gcaaagcaca aggcctagtc actagccgtg      660
ctccggggag gctgtccaaa agcaggaaga acaagggcaa agaaactcca tggaactcac     720
tttcccacca gggagtgaac cgcggcgtca tgctccattc tgagtagctc ccagccgagg     780
ccgccctcac cctcccgtaa taaggttcct gtatgtctga ggtttcactg gtaaggtcac     840
aaga                                                                   844
```

<210> SEQ ID NO 37
<211> LENGTH: 801
<212> TYPE: DNA
<213> ORGANISM: Homo sapiens
<220> FEATURE:
<221> NAME/KEY: allele
<222> LOCATION: (401)..(401)
<223> OTHER INFORMATION: y = c or t

<400> SEQUENCE: 37

```
aaggtttccc aaaatattta ttgaaagact tgaaatctag ctttctagac acataataag      60
gaagatagac ggtatctata ctcggtaatc tacatggtga cagcagtttc attccatcac     120
aattaaagca gaaccacaac atatattgag tataatttga tgttttaaaa ttattattta     180
tttataataa gtcttgaact tagctgtaat gacagacttc tcttttaaaa taatatctca     240
ttgtttatcc tattctaaac gcaagggata taacagtatt atagcccatg aactggatac     300
accaaagtga aagttttcaa aattataaat ttgtcttgtg ctgttgaaaa tcccttagag     360
acaggaatgg attcaggtat tctggggtct gaaatttata yaatcttggt ccatttaatg     420
tttctataac agaacacctg aggctaggta attgataagg aaaagaggtg tacttagcca     480
atgttctgca gcctgggaag ttacaagaaa tgtgctgcca gcatccactt ggcttctggt     540
gagagctttt catgctgcat gagaacatgc tagagaaggt caatggggaa aacagatcgt     600
gtgaagaggc caaactcaag ggcatcctg  gctttacaac aaccactctc atagaaacat     660
ttccatgaca aattcagtct tgcaagagtg agaactcact caactgcagc aataatggta     720
ccaagccatt catgagtgct ccatccccat gacccaaaca cctcctacga ggccctactt     780
ccaacaccac cacactaagg a                                               801
```

<210> SEQ ID NO 38
<211> LENGTH: 801
<212> TYPE: DNA
<213> ORGANISM: Homo sapiens
<220> FEATURE:
<221> NAME/KEY: allele
<222> LOCATION: (401)..(401)
<223> OTHER INFORMATION: y = c or t

<400> SEQUENCE: 38

```
atattaagct tttctttct gtttgttttt gttttgttta gttttaatc ctgtcttaga      60
agaacttatc tttattctca aaattaaatg taattttttt agtgacaaag aagaaaggaa    120
acctcattac tcaatccttc tggccaagag tgtcttgctt gtggcgcctt cctcatctct    180
atataggagg atcccatgaa tgatggttta ttgggaactg ctggggtcga ccccatacag    240
agaactcagc ttgaagctgg aagcacacag tgggtagcag gagaaggacc ggtgttggta    300
ggtgcctaca gagactatag agctagacaa agccctccaa actggcccct cctgctcact    360
gcctctcctg agtagaaatc tggtgaccta aggctcagtg yggtcaacag aaagctgcct    420
tcttcacttg aggctaagtc ttcatatatg tttaaggttg tctttctagt gaggagatac    480
atatcagaga acatttgtac aattccccat gaaaattgct ccaaagttga taacaatata    540
gtcggtgctt ctagttatat gcaagtactc agtgataaat ggattaaaaa atattccagaa   600
atgtattggg gggtggagga gaataagagg cagagcaaga gctagagaat tggtttcctt    660
gcttccctgt atgctcagaa acattgatt tgagcataga cgcagagact gaaaaaaaaa    720
tttactttga tctctgtttt tgaattctta ttatttatat tttgcttact acctttttttg   780
cctttttgtcc ttttgtggag a                                             801
```

<210> SEQ ID NO 39
<211> LENGTH: 701
<212> TYPE: DNA
<213> ORGANISM: Homo sapiens
<220> FEATURE:
<221> NAME/KEY: allele
<222> LOCATION: (501)..(501)
<223> OTHER INFORMATION: s = c or g

<400> SEQUENCE: 39

```
atttgagggc aagcaagggg tctgtgtgct ggagaagagt gaggaaggtg agaattaggg      60
agtgaggcct gggagattat gaggaaagga aacagatcat acagcgcctt ggaggccatt     120
ataaagactt tggtttttac ccttatgaga tgggaagcta ttggcggttt tagagcagga     180
aagtgacatg atctgattta tgttccaagg ctcatgctgg ccaccttgtt aagacaaaac     240
tggagggagg caagcagagc ggggacacca atgaggtaac catagtgacc atccagagga     300
gaaatgatgg tggcctggaa taggtagttc tgagaagtgt tgtattttgg aggtagatca     360
atagaattta ttggtgcatt gaatatatat gatgtgaaag aaagcgggga gacaaagata     420
acctcaacgc ttttggcctg agcagctgta agactgggat tgcatttgat cacagggcaa     480
gctcagtcgg gctcaaaact stttgctcct tcctggctgg aacttcgtgt gggcctaaga     540
tgtttaactg gaatttcatc tggcagactt aaacattgtg ttcttctttt aaaagctcaa     600
ataacaaata ttccaaaatg taaagcaaaa aaaggattta ttgaaatcat gtgacaatat     660
atccctaaca ccatgaagaa gatgacaatt atgatttcca t                        701
```

FIBROSIS SUSCEPTIBILITY IL22RA2 GENE AND USES THEREOF

This application is a U.S. National Phase application of PCT/EP2012/065222, filed Aug. 3, 2012, which claims the right of priority of U.S. Application Ser. No. 61/515,438, filed Aug. 5, 2011 and European Patent Application No 11306018.0, filed Aug. 5, 2011, each of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Feb. 12, 2014, is named 46033_704_831_SL.txt and is 124,366 bytes in size.

FIELD OF THE INVENTION

The present invention relates generally to the fields of genetics and medicine. The present invention discloses in particular the identification of a human susceptibility gene, which can be used for the diagnosis or prognosis of an abnormal deposit of Extra Cellular Matrix Proteins (ECMP) in tissue, potentially resulting in fibrosis, or for the detection of predisposition to such abnormal ECMP deposit or fibrosis, occurring in liver diseases, in cirrhosis, cutaneous keloid, obesity and any fibrotic disease and also in disease of other tissues such as heart, vessels or brain. The invention more particularly discloses certain alleles of the IL22RA2 gene on chromosome 6 related to susceptibility to fibrosis and representing novel targets for the screening of therapeutically active drugs. The present invention relates more specifically to particular mutations in the IL22RA2 gene and expression products, as well as to diagnostic tools and kits based on these mutations.

BACKGROUND OF THE INVENTION

Accumulation of Extra Cellular Matrix Proteins in tissue may have deleterious effects. Abnormal deposit of ECMP in tissue may result in tissue fibrosis.

Fibrosis is an excessive growth of fibrous connective tissue in an organ, any part, or tissue thereof, for example in a liver, any part or tissue thereof, especially in response to an injury.

Abnormal fibrosis occurs in chronic hepatic inflammations of various aetiologies such as in Hepatitis Virus and Schistosome infections. It was shown previously that certain subjects infected by Schistosomes are slow fibrosers whereas others are rapid fibrosers and that this depends in part on a major gene located on Chr 6q22-q23 (Dessein et al., 1999; Mohamed-Ali et al., 1999). International patent application WO2010/094740 identifies CTGF (CCN2) as a fibrosis susceptibility gene in this region.

Schistosomiasis is caused by helminths that develop in the vascular system of their hosts and lay eggs that are for some of them carried over to the liver where they trigger inflammation in the periportal space. Since worms live for years in their human host, chronic liver inflammation associated with much tissue destruction is common in infected subjects. Tissue repair requires the deposit of ECMP in the damaged tissues that are later on turned over and replaced by normal hepatocytes. In some patients ECMP accumulate in the periportal space forming fibrosis deposits that reduce blood flow causing varicose veins, ascites. After months or years of chronic or repeated injury, fibrosis becomes permanent and irreversible. Subjects die of the consequences of fibrosis.

In South countries, it is estimated that 5 to 10% of the 350 millions of infected subjects may develop severe hepatic fibrosis. There is no good marker allowing to predict and follow hepatic fibrosis progression in Schistosome infected subjects.

Diagnosis of hepatic fibrosis is mostly based on liver biopsy, elastometry and ultrasound analysis.

Biopsies are obtained via percutanous, transjugular, radiographically-guided fine-needle or laparoscopic route, depending upon the clinical setting. Histopathological examination enables the clinician to grade the severity of necroinflammation and stage the extent of fibrosis. The Metavir scoring system attributes a score to the stages of fibrosis on a 1-4 scale as follows: F0=no fibrosis, F1=portal fibrosis without septa, F2=portal fibrosis and few septae, F3=numerous septae without cirrhosis, F4=cirrhosis (Bedossa et al., 1996). Liver biopsy is an invasive and costly procedure, and samples only a small portion of the liver. Thus it cannot afford a global assessment of hepatic fibrosis, and is subject to sampling variation and inter- and intra-observer error. In addition, liver biopsy is associated with significant morbidity of 3% and a mortality rate of 0.03%. Potential complications include local hematoma, infection and pain related to the biopsy.

Noninvasive tests (i.e., serologic markers, elastometry, ultrasound analysis) are also used but are not yet ready for routine clinical use.

Panels of blood markers have been tested mostly in patients with chronic hepatitis C or cirrhosis due to viral hepatitis C. These studies revealed that serum markers can rule on or rule out fibrosis in approximately 35% of patients (Sebastiani et al., 2006). However, when looking at patients individually, these markers could not reliably differentiate between the various stages of fibrosis. A more recent study incorporated three panels of serum markers to devise an algorithmic approach that improved diagnostic accuracy (Parkes et al., 2006). The three panels evaluated were the APRI (aspartate transaminase to platelet ratio index), the Forns' index (platelets, gammaglutamyltranspeptidase, cholesterol) and the Fibrotest (GGT, haptoglobin, bilirubin, apolipoprotein A, alpha-2-macroglobulin). An algorithm consisting of the APRI followed by the Fibrotest boosted the diagnostic accuracy of fibrosis to above 90%. This group estimated that use of this algorithm could obviate the need for up to 50% of liver biopsies. However, the individual stages of fibrosis are not distinguishable using this algorithm. The limitation of these serum markers is the possibility of false positives when there is highly active hepatic inflammation.

Fibroscan is another approach to staging hepatic fibrosis, which is based on elastography, which provides rapid measurement of mean hepatic tissue stiffness (Ziol et al., 2005). A probe is employed to transmit a vibration of low frequency and amplitude into the liver. This vibration wave triggers an elastic shear wave, whose velocity through the liver is directly proportional to tissuestiffness measured in kilopascals (kPa). Sensitivity of the Fibroscan technique ranged from 79 to 95%, and specificity from 78 to 95%, compared to the liver biopsy. However, the limitations of this technique are associated with attenuation of elastic waves in fluid or adipose tissue, which would impair assessment of fibrosis in patients. In addition, Fibroscan is an extremely expensive instrument.

Today's standard-of-care (SOC) for eradication of HCV from the liver consists of Pegylated type I interferon (PegIFN) and synthetic nucleoside ribavirin (RBV) therapy (Fried M W et al; N Engl J. Med. 2002; 347(13):975-82; EASL Clinical Practice Guideline: Management of hepatitis C virus infection, J. Hepatol. 2011; 55:245-264). However, this standard therapy has limited and unpredictable efficacy, an extensive toxicity profile frequently leading to treatment discontinuation and is very expensive. Less than half of the chronically HCV-infected individuals of genotype 1 and 4 respond to long-term treatment (48 weeks) of standard therapy (PegIFN/RBV) (Testino G et al; Hepatogastroenterology 2011; 58(106):536-8).

Thus, there is a need for a method for selecting patients who have better chances to respond to a treatment in order to optimize treatment, avoid side effects for non-responders and reduce treatment costs.

Altogether there is still a need for an efficient method to prognose the fibrosis progression and the treatment efficiency.

SUMMARY OF THE INVENTION

The purpose of the present invention is to provide a new genetic approach for fibrosis prognosis and treatment. The present invention now discloses the identification of another human fibrosis susceptibility gene locus, the IL22RA2 gene locus, which can be used for detecting predisposition to, diagnosis and prognosis of an abnormal ECMP deposit, especially fibrosis, especially hepatic fibrosis, as well as for the screening of therapeutically active drugs. The invention resides, in particular, in a method which comprises detecting in a sample from the subject the presence of an alteration in the IL22RA2 gene locus, the presence of said alteration being indicative of the presence or predisposition to an abnormal ECMP deposit or fibrosis.

A particular object of this invention resides in an in vitro method of detecting predisposition to or diagnosis and/or prognosis of an abnormal ECMP deposit or fibrosis occurring in a subject, the method comprising detecting the presence of an alteration in the IL22RA2 gene or polypeptide in a sample from the subject, the presence of said alteration being indicative of the presence of an abnormal ECMP deposit or a fibrosis or the predisposition to an abnormal ECMP deposit or fibrosis. A particular object of this invention resides in a method for assessment (prediction) of the progression of an abnormal ECMP deposit or fibrosis.

In a preferred embodiment, said alteration is located within 500 kb, preferably 100 kb, preferably 20 kb, upstream the start codon of the IL22RA2 gene and within 500 kb, preferably 100 kb, preferably 20 kb, downstream the 3'UTR of the IL22RA2 gene. Preferably, the alteration lies in the surrounding sequences of 10 kb region, upstream the starting codon of the IL22RA2 gene and 10 kb region, downstream the untranslated region (3'UTR).

In another preferred embodiment, said alteration is a mutation, an insertion or a deletion of one or more bases. In a more preferred embodiment, said alteration is one or several single nucleotide polymorphism(s) SNP(s) or a haplotype of SNPs associated with fibrosis. Preferably, said single nucleotide polymorphisms are SNPs flanking IL22RA2 gene, which are allelic variants lying close to the IL22RA2 gene.

The method of the invention allows for detection and prognosis of fibrosis which occurs in a human fibrotic disease selected from hepatic diseases fibrosis, cirrhosis, cutaneous keloid, hypertrophic scars and obesity, alcoholism, or drug hepato-toxicity. Especially, the hepatic fibrosis may be caused by hepatic A virus, hepatic B virus, hepatic C virus (HCV), *Schistosoma japonicum* (*S. japonicum*) or *Schistosoma mansoni* (*S. mansoni*) infection.

In a particular embodiment, the method comprises genotyping SNPs in the IL22RA2 gene locus in a biological sample of a subject, preferably infected with a hepatitis virus or parasite, wherein the presence of genotype GG in SNP rs6570136, TT in SNP rs7774663, TT, CT in SNP rs11154915 and/or CC in SNP rs2064501, is indicative of a risk of developing an abnormal ECMP deposit such as a fibrosis or of the development of an abnormal ECMP deposit such as a fibrosis, or of a poor prognostic of fibrosis in the subject. The fibrosis is more particularly hepatic fibrosis.

Alternatively the method may comprise genotyping any SNP in Linkage Disequilibrium (LD) with those mentioned herein.

Preferably, the alteration in the IL22RA2 gene locus is determined by performing a selective hydridization assay, a sequencing assay, a microsequencing assay, and/or an allele-specific amplification assay.

In another aspect of the invention, said alteration in the IL22RA2 gene is determined by restriction enzyme digestion, the detection of at least one said SNP being an indication of fibrosis.

This invention also relates to a method for selecting a therapeutic compound for a subject that has or is predisposed to develop an abnormal ECMP deposit such as fibrosis, said method comprising contacting a test compound with a IL22RA2 polypeptide or gene or a fragment thereof and determining the ability of said test compound to enhance or reduce biological activity or function of a pathway related to the IL22RA2 gene.

A further subject of the invention is an in vitro method for determining the likelyhood for a patient affected with a viral infection to respond to a treatment with an antiviral agent and/or an interferon, which method comprises determining alteration in IL22RA2 gene locus or in IL22RA2 protein expression or activity in a biological sample of the patient.

In a particular embodiment, the method comprises comprising genotyping SNPs in the IL22RA2 gene locus in a biological sample of a subject, wherein the presence of a TT genotype with respect to SNP rs11154915, a AG or GG genotype with respect to SNP rs6570136, a CT genotype with respect to SNP rs2064501, and/or a AA genotype with respect to SNP rs1543509, is in favor of a patient's positive response to the treatment. Alternatively the method may comprise genotyping any SNP in Linkage Disequilibrium (LD) with those mentioned herein.

In a particular embodiment, the treatment comprises an antiviral agent, optionally with an interferon.

Preferably said antiviral agent is an inhibitor of viral replication, such as ribavirin.

LEGEND TO THE FIGURES

Antischistosome treatment: subjects have taken Praziquantel over the past ten years after the following regimens: never, 1 to 4 times, 5-10 times, >10 times.

Controls are subjects who had not been exposed to *S. japonicum* and never treated with Praziquantel. Stars: Cultures stimulated with *S. japonicum* eggs; Open circles: Resting cultures: Number of subjects per groups: controls (19), Treatments: no Treatments (9), 1-4 (30), 5-10 (23), <10 (8)

Figure 2C:
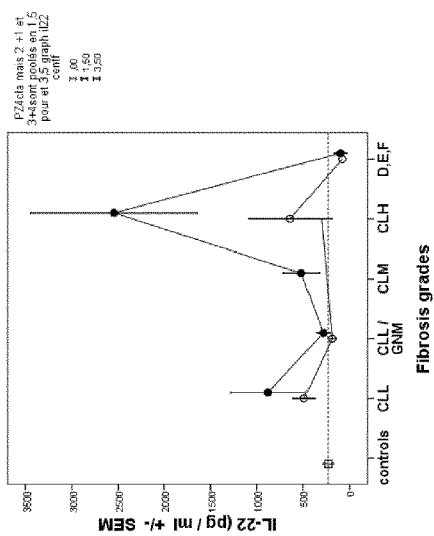
FIG. 2A shows IL-22 levels in PBMC cultures vary with the number of anti-schistosome treatments over the past ten years. Study subjects were more than 30 and less than 65 years old and had no active HBV infections (HBS Ag-)
Figure 2B:
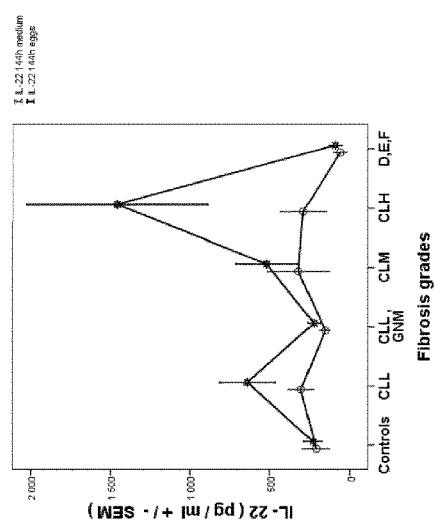

FIG. 2B shows that IL-22 levels in PBMC cultures vary with the degree of hepatic fibrosis.

Study subjects were more than 30 and less than 65 years old and had no active HBV infections (HBS Ag-) Controls are subjects who had not been exposed to *S. japonicum*; Stars Cultures stimulated with *S. japonicum* eggs; Open circles: Resting cultures. Fibrosis grade was evaluated as described in Methods and are mostly Central Fibrosis grades, peripheral fibrosis was taken only taken into account to split subjects with mild Central fibrosis into one group (CLL) with no or mild peripheral Fibrosis and one group (CLL, GNM) with mild central fibrosis and advanced to severe (GNM, GNH) peripheral fibrosis. Number of subjects per groups: controls (19), CLL (23), CLL GNM (27), CLM (10), CLH (7), D,E,F (3)

FIG. 2C shows IL-22 levels in subjects with different hepatic fibrosis grades and different treatment. Study subjects were more than 30 and less than 65 years old and had no active HBV infections (HBS Ag-). Controls are subjects who had not been exposed to *S. japonicum*. Subjects have been treated either 0 to 4 times (open circles) or more than 5 to 20 times (closed circles). Number of subjects per groups: Treatments groups were pooled as follows: 0 to 4 treatments and >5 treatments in order to increase the number of subjects per point Controls: 19; 0-4 Treatments: 39; >5 Treatments: controls: 31

Figure 3A:
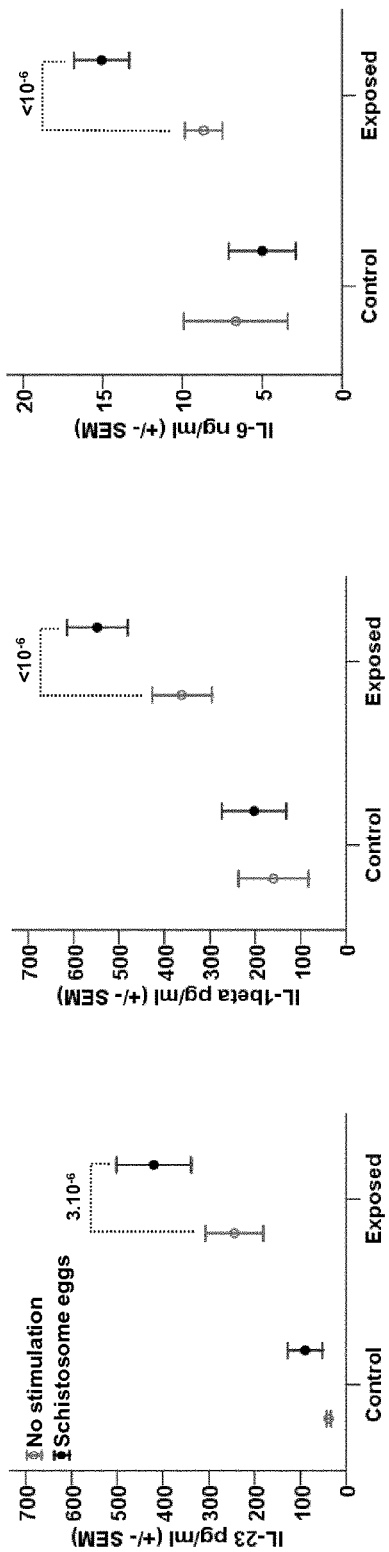

FIG. 3A shows the impact of the anti-schistosome treatments on IL-22, IL-6, IL-1β, or IL-23 levels in egg-stimulated cultures. Study subjects were more than 30 and less than 65 years old and had no active HBV infections (HBS Ag-) Controls are subjects who had not been exposed to *S. japonicum*. PBMC from study subjects were stimulated with eggs and cytokines were evaluated in supernatants at 24 hrs (IL-1b, IL-23, IL-6) and at 144 hrs (Il-22). IL-6 levels were multiplied by 0.1.

Figure 2A:
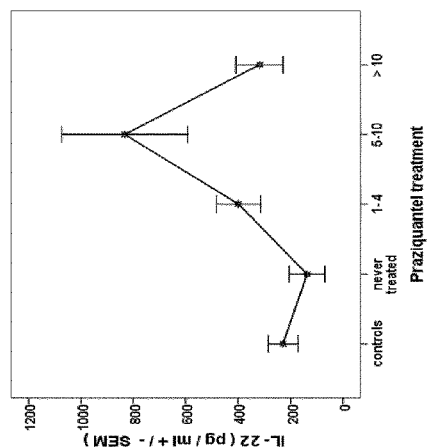
Figure 3C:
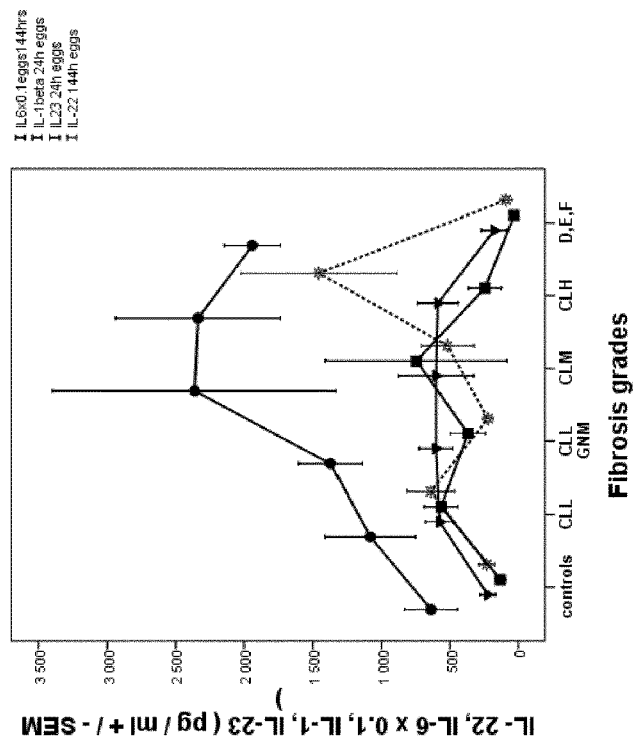
Figure 3B:
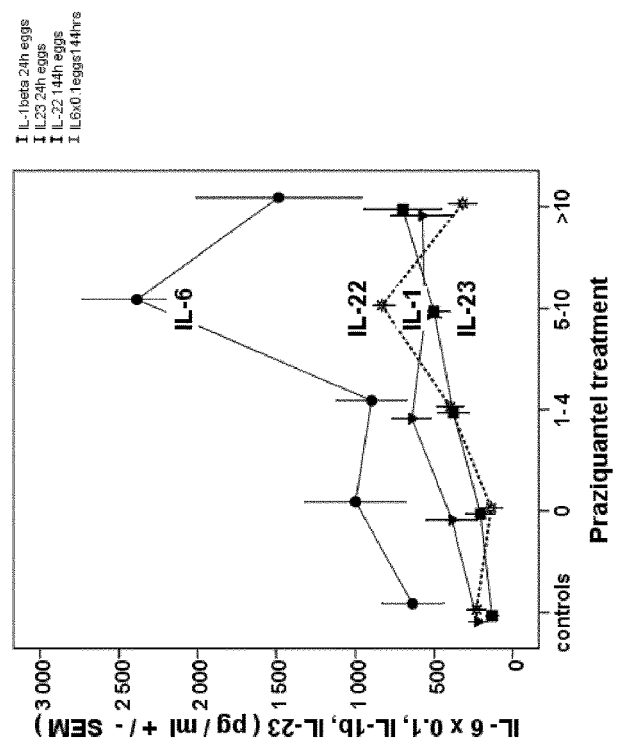

FIG. 3B shows the IL-22, IL-6, IL-1β or IL-23 levels in egg-stimulated PBMC from controls and from subjects with various degree of Hepatic fibrosis. Study and Number of subjects in each group as for FIG. 2A.

FIG. 3C shows the variations of IL-6, IL-1β, and IL-23 with hepatic fibrosis.

Figure 4:
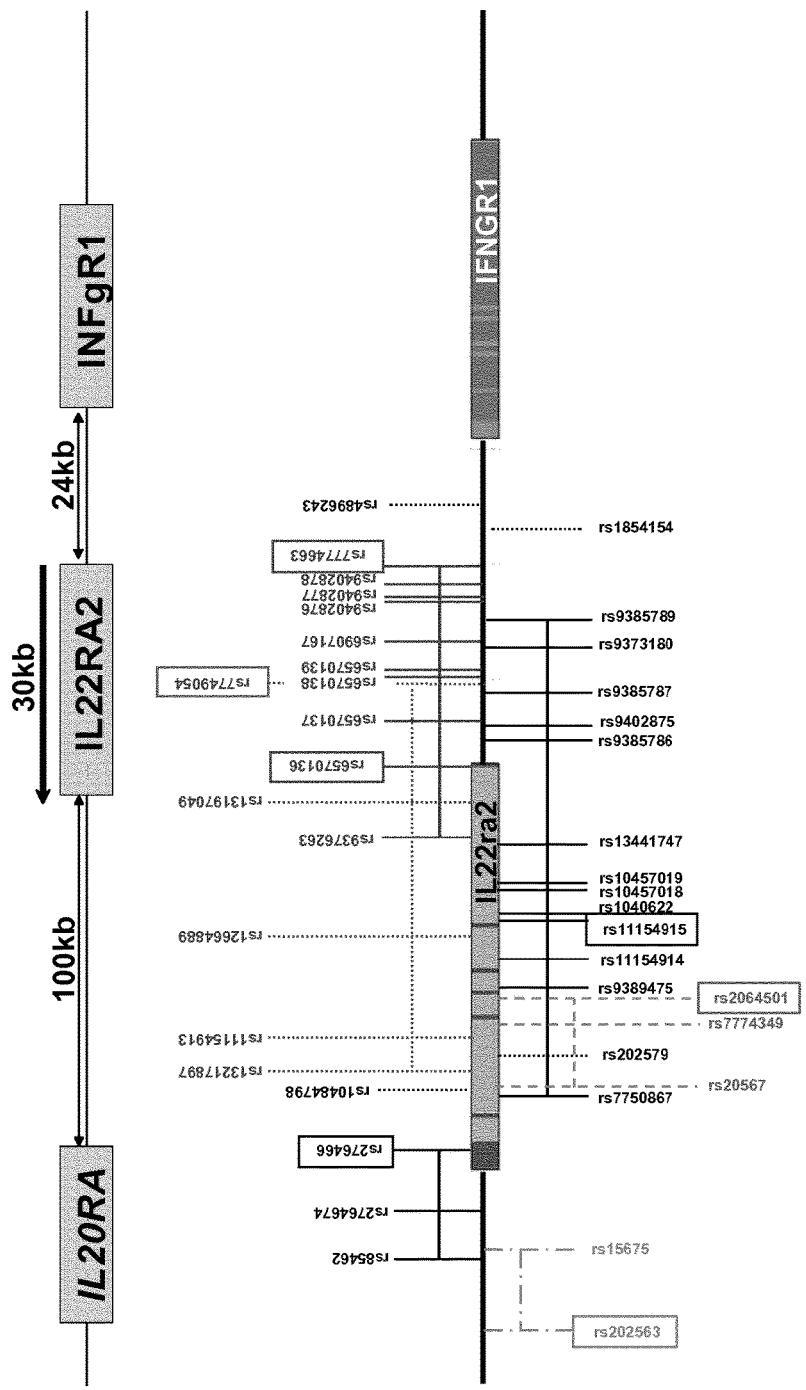

FIG. 4 is a map that locates SNPs and correlation bins in IL22RA2

DETAILED DESCRIPTION OF THE INVENTION

This invention provides valuable genetic markers to predict disease progression in fibrosis, especially in hepatic fibrosis, in humans.

Early detection of an abnormal accumulation of ECMP or fibrosis, and regular monitoring of such accumulation or fibrosis, would allow for initiation of anti-fibrotic therapies capable of halting and even reversing this process. This would in turn prevent progression to human fibrosis disease, for example hepatic fibrosis or hepatic cirrhosis, and the morbidity and mortality this condition entails. The development of these various early fibrosis detection techniques bodes well for the future care of patients with liver disease.

The inventors have now identified a gene associated with human fibrosis. They have shown that fibrosis in Chinese, Sudanese and Brazilian cohorts infected with *Schistosoma japonicum* and with *Schistosoma mansoni* respectively is markedly dependent on allelic variants lying in the IL22RA2 gene. The IL22RA2 (for "interleukin-22 receptor alpha-2") gene, also named IL22R-BP, encodes a soluble form of the IL-22 receptor that competes for the binding of IL-22 to its receptor.

More particularly the inventors performed case control studies on independent samples of Chinese (exposed to *S. japonicum*), Sudanese and Brazilians (exposed to *S. mansoni*) all living in endemic regions. Hepatic fibrosis (HF) was evaluated using echography by at least two observers for each sample. All Tag SNPs in IL22RA2 (Minor Allele Frequency>10%) were tested. To rule out whether SNPs in linkage disequilibrium with the associated SNPs could account for the observed associations, the inventors evaluated SNPs in the 500 Kb regions in 3' and 5' of IL22RA2.

The invention thus provides a method of determining a risk of developing a hepatic fibrosis or of the development of a hepatic fibrosis, or of a poor prognostic of hepatic fibrosis in a subject, the method comprising detecting the presence of risk-associated single nucleotide polymorphism (SNP) alleles at the IL22RA2 gene locus in a sample from said subject.

The invention more particularly provides a method of determining a risk of developing a hepatic fibrosis or of the development of a hepatic fibrosis, or of a poor prognostic of hepatic fibrosis, the method comprising genotyping a SNP in the IL22RA2 gene locus in a sample from said subject.

Another purpose of the present invention is to provide a genetic approach for predicting the response to viral infection treatment. The present invention now discloses the identification of an antiviral treatment response gene locus, the IL22RA2 gene locus, which can be used for predicting the response to antiviral treatment of a patient suffering from viral infection, especially HCV. The invention resides, in particular, in a method which comprises detecting in a sample from the subject the presence of an alteration in the IL22RA2 gene locus, the presence of said alteration being indicative of the response to the treatment, i.e. being indicative of a level of risk for the patient not to respond to the treatment The method of the invention allows for prediction of the response to treatment with an antiviral agent such as ribavirin, and an interferon administered to patient suffering of a viral infection, especially hepatitis C.

This invention provides valuable markers to predict response to antiviral treatment, especially in hepatitis C.

Early identification of responders and non-responders subjects to antiviral treatment, would allow for initiation of an individualized (personalized) treatment based on patients' genotype. This would in turn help physicians to make more informed decision, and avoid needless expenditures and unnecessary side effects. The development of these various early prediction techniques bodes well for the future care of patients with viral infection, especially hepatitis C.

The inventors have now identified a gene associated with response to an antiviral treatment. They have shown that response to the antiviral treatment Ribavirin-IFN in various cohorts infected with HCV is dependent on allelic variants lying in the IL22RA2 gene.

Although the experimental data gathered by the inventors did not allow to confirm association of certain alleles, depending on the tested population, the present invention is not limited to the particular SNPs that were found significantly correlated with fibrosis in all tested populations. Indeed, several reasons could account for the failure in confirming significant correlation in some populations, including an insufficient cohort, the incomplete assessment of confounding variables, a lower frequency of the SNPs in said populations, etc.

Definitions

Within the context of this invention, the term "abnormal deposit of Extra Cellular Matrix Proteins (ECMP)" refers to the extracellular matrix components (including laminin, fibronectin EIIIA, collagen I and IV, procollagen III, elastin, tenascin) that may accumulate in all types of human tissues. Such accumulation may be deleterious, for instance when it occurs in arteries, heart, or brain. When the deposition is massive, the accumulation results in fibrosis of the tissue.

Within the context of this invention, "fibrosis" designates all types of human fibrosis occurring in all the fibrotic human diseases, for example in hepatic diseases, cirrhosis, cutaneous keloid, hypertrophic scars, sclerodermia, obesity and any fibrotic disease.

Within the context of this invention, "hepatic fibrosis" or "HF" designates all types of fibrosis occurring in a liver, tissue thereof or any part of tissue thereof. Hepatic fibrosis occurs especially in response to an injury. Hepatic fibrosis can be the common response to chronic liver injury, ultimately leading to cirrhosis and its complications, portal hypertension, liver failure, and hepatocellular carcinoma. Hepatic fibrosis is overly exuberant wound healing in which excessive connective tissue builds up in the liver. The extracellular matrix is either overproduced, degraded deficiently, or both. The trigger is chronic injury, especially if there is an inflammatory component. Various types of chronic liver injury can cause fibrosis, such as chemical fibrosis ($CCl_4$), bacterial (i.e., brucellosis), parasitic (i.e., bilharziosis/schistosomiasis caused by Schistosoma species; or echinococcosis infections) or viral (i.e., hepatitis caused by hepatic A virus (HAV), hepatic B virus (HBC) or hepatic C virus (HCV) infections). Within the context of this invention, "cutaneous keloid" is an excessive growth of scar tissue on the skin. More particularly, keloids and hypertrophic scars (HSc) are dermal fibroproliferative disorders unique to humans that occur following trauma, inflammation, surgery, burns and sometimes spontaneously. These are characterized by excessive deposition of collagen in the dermis and the subcutaneous tissues. Contrary to the fine line scar characteristics of normal wound repair, the exuberant scarring of keloid and HSc results typically in disfigurement, contractures, pruritis and pain. Keloids occur in individuals with a familial disposition among the Blacks, Hispanics and Orientals. Unlike HSc, the keloid scars enlarge and extend beyond the margins of the original wound and rarely regress. These disorders represent aberrations in the fundamental processes of wound healing, which include cell migration and proliferation, inflammation, increased synthesis and secretion of cytokines and extra cellular matrix (ECM) proteins and remodelling of the newly synthesized matrix. Biologically, keloids are fibrotic tissue characterized by a collection of atypical fibroblasts with excessive deposition of extracellular matrix components, especially collagen, fibronectin, elastin, and proteoglycans. Generally, keloids contain relatively acellular centers and thick, abundant collagen bundles that form nodules in the deep dermal portion of the lesion. The release and activation of growth factors during the inflammatory phase of healing are pre-requisites for the scar processes, including angiogenesis, reepithelialization, recruitment and proliferation of fibroblasts and matrix deposition. Then, abnormal production of activity of the regulating cytokine including IL22RA2, could contribute to the development of keloids.

Within the context of this invention, "the IL22RA2 gene locus" designates all sequences or products in a cell or organism, including IL22RA2 coding sequences, IL22RA2 non-coding sequences (e.g., introns), IL22RA2 regulatory sequences controlling transcription and/or translation (e.g., promoter, enhancer, terminator, etc.), all corresponding expression products, such as IL22RA2 RNAs (e.g., mRNAs) and IL22RA2 polypeptides (e.g., a pre-protein and a mature protein); as well as surrounding sequences of 500 kb region, preferably 100 kb, preferably 20 kb region, upstream the starting codon of the IL22RA2 gene and 500 kb region, preferably 100 kb, preferably 20 kb region, downstream the untranslated region (3'UTR). For example, the IL22RA2 locus comprises surrounding sequences comprising the SNPs of Table 1.

Within the context of the present invention, the term "prognosis" includes the detection, monitoring, dosing, comparison, etc., at various stages, including early, pre-symptomatic stages, and late stages, in adults, children and pre-birth. Prognosis typically includes the assessment (prediction) of the progression of fibrosis and the characterization of a subject to define most appropriate treatment (pharmaco-genetics), etc. The present invention provides prognostic methods to determine the speed of the progression of fibrosis or an associated disorder resulting from a mutation or a polymorphism in the IL22RA2 gene locus.

The "sample" may be any biological sample derived from a patient or subject, which contains nucleic acids or polypeptides. Examples of such samples include fluids, tissues, cell samples, organs, biopsies, etc. Most preferred samples are blood, plasma, saliva, urine, seminal fluid, etc. The sample may be collected according to conventional techniques and used directly for diagnosis or stored.

The "patient" may be any mammal, preferably a human being, whatever its age or sex. The patient may be infected with a virus, including a virus which is selected from the group consisting of virus of the family of Arenaviridae (e.g. Lassa virus), Coronaviridae (e.g. Sever Acute Respiratory Syndrome virus), Flaviviridae (e.g. Hepatitis C or B Virus, Dengue virus, West Nil Virus, Yellow Fever Virus, Tick-Borne Encephalitis virus), Filoviridae (e.g. Ebola, Marburg), Herpesviridae (e.g. Herpes Simplex Virus, Cytomegalovirus, Epstein-Barr Virus, Varicella Zoster Virus), Orthomyxoviridae (e.g. Influenza A and B), Paramyxoviridae (e.g. Respiratory Syncytial Virus, Paralnfluenza Virus, PMV, Measles), Poxviridae (e.g. Vaccinia, Variola), Rhabdoviridae (e.g. Vesicular Stomatitis Virus, Viral Hemorrhagic Septicemia Virus, Rabies), Retroviridae (e.g. HIV and other retroviruses), Togaviridae (e.g. Chikungunya, Sindbis, Semliki Forest Virus, Ross River Virus, Eastern Equine Encephalitis Virus). In a particular embodiment, the patient is infected with a Hepatitis C virus, e.g. Hepatitis C virus of genotype 1.

In a method for determining the likelyhood for a patient affected with a viral infection to respond to a treatment with an antiviral agent and/or an interferon, the term "viral infection" designated all types of human viral infection which may be treated with Ribavirin and/or IFN, for examples hepatitis C, hepatitis B, Respiratory Syncytial Virus (RSV) bronchiolitis, adenovirus disease, influenza and any human viral infection treated with Ribavirin and/or IFN.

Within the context of this invention, "responder" refers to the phenotype of a patient who responds to the treatment with an antiviral agent, especially Ribavirin, and/or an IFN, i.e. the viral load is decreased, at least one of his symptoms is alleviated, or the development of the disease is stopped, or slowed down.

Within the context of this invention, "non-responder" refers to the phenotype of a patient who either does not respond to the treatment with an antiviral, especially Ribavirin, and/or an IFN, or who responds but relapses within one or two years. Non response to treatment refers to a viral load that does not substantially decrease and patient symptoms are not alleviated, or the disease progresses. Relapsing patients respond to treatment for a short period but their viral load and symptoms increase again within one or two years of the end of the treatment.

The term "treatment" or "antiviral treatment" refers to administration of an antiviral agent and/or interferons (IFN).

Preferably the interferon is interferon gamma. However other interferons are encompassed, including interferon alpha 2B, pegylated interferon alpha, consensus interferon, interferon alpha 2A, and lymphoblastoid interferon tau. In a preferred embodiment, the interferon is PEGylated interferon, such as PEGylated interferon gamma.

The "antiviral agent" may be any compound that interferes with the virus entry into a cell, or its replication, or inhibits the activity of a viral protein. For instance it may be interfering RNA, anti-sense RNA, Imiqimod, ribavirin, an inosine 5'-monophospate dehydrogenase inhibitor, amantadine, or rimantadine. More generally it may be a viral protease inhibitor.

When the virus is HCV virus, the viral agent may be an inhibitor of HCV metalloprotease, HCV serine protease, HCV polymerase, HCV helicase, HCV NS4B protein, HCV entry, HCV assembly, HCV egress, or HCV NS5A protein.

In a preferred aspect, the interferon is interferon gamma, such as PEGylated interferon gamma. In another preferred aspect, the interferon is interferon alpha, such as PEGylated interferon alpha. In a specific embodiment, the treatment comprises ribavirin and interferon gamma or alpha, preferably PEGylated interferon gamma or alpha.

Alterations

The alteration may be determined at the level of the IL22RA2 DNA, RNA or polypeptide. Optionally, the detection is performed by sequencing all or part of the IL22RA2 gene locus or by selective hybridization or amplification of all or part of the IL22RA2 gene locus. More preferably a IL22RA2 gene locus specific amplification is carried out before the alteration identification step. An alteration in the IL22RA2 gene locus may be any form of mutation(s), deletion(s), rearrangement(s) and/or insertions in the coding and/or non-coding region of the locus, alone or in various combination(s). Mutations more specifically include point mutations. Deletions may encompass any region of two or more residues in a coding or non-coding portion of the gene locus, such as from two residues up to the entire gene or locus. Typical deletions affect smaller regions, such as domains (introns) or repeated sequences or fragments of less than about 50 consecutive base pairs, although larger deletions may occur as well. Insertions may encompass the addition of one or several residues in a coding or non-coding portion of the gene locus. Insertions may typically comprise an addition of between 1 and 50 base pairs in the gene locus. Rearrangement includes inversion of sequences. The IL22RA2 gene locus alteration may result in the creation of stop codons, frameshift mutations, amino acid substitutions, particular RNA splicing or processing, product instability, truncated polypeptide production, etc. The alteration may result in the production of a IL22RA2 polypeptide with altered function, stability, targeting or structure. The alteration may also cause a reduction in protein expression or, alternatively, an increase in said production.

In a preferred embodiment, said alteration is a mutation, an insertion or a deletion of one or more bases. In a particular embodiment of the method according to the present invention, the alteration in the IL22RA2 gene locus is selected from a point mutation, a deletion and an insertion in the IL22RA2 gene or corresponding expression product, more preferably a point mutation and a deletion. The alteration may be determined at the level of the IL22RA2 DNA, RNA or polypeptide.

In a most preferred embodiment, the method comprises genotyping the IL22RA2 gene, to determine the presence of a SNP at any of the position indicated in Table 1A.

TABLE 1A

Fibrosis-associated SNPs in the IL22RA2 gene locus

| Bin | SNP | Position | Taqman Assay Number | SEQ ID | MAF (HapMap) | | |
|-----|-----|----------|---------------------|--------|------|------|------|
| | | | | | CEU | YRI | CHB |
| I | rs9376263 | 137489626 | | SEQ ID NO: 1 | 0.41 (T) | 0.13 (C) | 0.34 (C) |
| | rs6570136 | 137494622 | C_2523610_10 | SEQ ID NO: 2 | 0.42 (A) | 0.25 (G) | 0.34 (G) |
| | rs6570137 | 137498645 | | SEQ ID NO: 3 | 0.38 (C) | 0.13 (T) | 0.37 (T) |
| | rs6570138 | 137501914 | | SEQ ID NO: 4 | 0.41 (T) | 0.25 (G) | 0.34 (G) |
| | rs6570139 | 137502056 | | SEQ ID NO: 5 | 0.41 (A) | 0.12 (G) | 0.31 (G) |
| | rs6907167 | 137503761 | | SEQ ID NO: 6 | 0.41 (T) | 0.25 (G) | 0.33 (G) |
| | rs9402876 | 137509025 | | SEQ ID NO: 7 | 0.41 (C) | 0.09 (T) | 0.32 (T) |
| | rs9402877 | 137509075 | | SEQ ID NO: 8 | 0.41 (A) | 0.13 (T) | 0.34 (T) |
| | rs9402878 | 137509292 | | SEQ ID NO: 9 | 0.37 (G) | 0.29 (T) | 0.33 (T) |
| | rs7774663 | 137510893 | C_30217943_10 | SEQ ID NO: 10 | 0.36 (C) | 0.33 (T) | 0.38 (T) |
| II | rs13217897 | 137471327 | | SEQ ID NO: 11 | 0.18 (A) | 0.26 (A) | 0.44 (A) |
| | rs11154913 | 137474838 | | SEQ ID NO: 12 | 0.17 (G) | 0.28 (G) | 0.44 (G) |
| | rs12664889 | 137481612 | | SEQ ID NO: 13 | 0.18 (A) | 0.30 (A) | 0.46 (A) |
| | rs13197049 | 137491211 | | SEQ ID NO: 14 | 0.18 (T) | 0.26 (T) | 0.44 (T) |
| | rs7749054 | 137500786 | C_32241951_10 | SEQ ID NO: 15 | 0.19 (G) | 0.26 (G) | 0.43 (G) |
| III | rs202563 | 137461492 | C_3010272_10 | SEQ ID NO: 16 | 0.49 (G) | 0.42 (A) | 0.26 (G) |
| | rs156751 | 137463294 | | SEQ ID NO: 17 | 0.49 (T) | 0.19 (T) | 0.26 (T) |
| IV | rs85462 | 137463154 | | SEQ ID NO: 18 | 0.21 (G) | 0.08 (G) | 0.16 (G) |
| | rs276467 | 137464218 | | SEQ ID NO: 19 | 0.20 (A) | 0.07 (A) | 0.16 (A) |
| | rs276466 | 137466614 | C_3010277_10 | SEQ ID NO: 20 | 0.21 (G) | 0.07 (G) | 0.14 (G) |
| | rs28366 | | | SEQ ID NO: 21 | | | |

TABLE 1A-continued

Fibrosis-associated SNPs in the IL22RA2 gene locus

| Bin | SNP | Position | Taqman Assay Number | SEQ ID | MAF (HapMap) CEU | YRI | CHB |
|-----|-----|----------|---------------------|--------|------|-----|-----|
| V | rs7750867 | 137470186 | | SEQ ID NO: 22 | 0.16 (T) | 0.09 (T) | 0.07 (T) |
|   | rs9389475 | 137478484 | | SEQ ID NO: 23 | 0.17 (T) | 0.07 (T) | 0.06 (T) |
|   | rs11154914 | 137480411 | | SEQ ID NO: 24 | 0.17 (G) | 0.07 (G) | 0.07 (G) |
|   | rs11154915 | 137482982 | C_9800072_30 | SEQ ID NO: 25 | 0.16 (T) | 0.07 (T) | 0.05 (T) |
|   | rs1040622 | 137483258 | | SEQ ID NO: 26 | 0.16 (C) | 0.08 (C) | 0.07 (C) |
|   | rs10457018 | 137484893 | | SEQ ID NO: 27 | 0.16 (A) | 0.08 (A) | 0.07 (A) |
|   | rs10457019 | 137484979 | | SEQ ID NO: 28 | 0.17 (A) | 0.07 (A) | 0.07 (A) |
|   | rs13441747 | 137488608 | | SEQ ID NO: 29 | 0.17 (C) | 0.09 (C) | 0.07 (C) |
|   | rs9385786 | 137497052 | | SEQ ID NO: 30 | 0.16 (T) | 0.07 (T) | 0.06 (T) |
|   | rs9402875 | 137498018 | | SEQ ID NO: 31 | 0.18 (C) | 0.08 (C) | 0.06 (C) |
|   | rs9385787 | 137500399 | | SEQ ID NO: 32 | 0.17 (C) | 0.08 (C) | 0.07 (C) |
|   | rs9373180 | 137503455 | | SEQ ID NO: 33 | 0.17 (G) | 0.04 (G) | 0.07 (G) |
|   | rs9385789 | 137505172 | | SEQ ID NO: 34 | 0.17 (A) | 0.08 (A) | 0.07 (A) |
| VI | rs202567 | 137470844 | | SEQ ID NO: 35 | 0.48 (G) | 0.06 (A) | 0.22 (A) |
|   | rs7774349 | 137475858 | | SEQ ID NO: 36 | 0.48 (C) | 0.06 (T) | 0.21 (T) |
|   | rs2064501 | 137477823 | C_11693858_10 | SEQ ID NO: 37 | 0.48 (T) | 0.06 (C) | 0.23 (C) |
| VII | rs1543509 | | | SEQ ID NO: 38 | | | |
|   | rs17066102 | | | SEQ ID NO: 39 | | | |

Hapmap: CEU European cohort, YOR African cohort (Yorubas), CHB Asian cohort (Chinese)

Preferably the method comprises genotyping a SNP selected in the group consisting of rs6570136, rs7774663, rs11154915 and rs2064501.

The presence of a G allele with respect to SNP rs6570136, more particularly of a GG genotype, is deleterious for the patient, i.e. it is indicative of a patient being likely to develop abnormal deposit of ECMP, or fibrosis, especially hepatic fibrosis.

The presence of a T allele with respect to SNP rs7774663, more particularly of a TT genotype, is deleterious for the patient, i.e. it is indicative of a patient being likely to develop abnormal deposit of ECMP, or fibrosis, especially hepatic fibrosis.

The presence of a T allele with respect to SNP rs11154915, more particularly of a TT or CT genotype, is deleterious for the patient, i.e. it is indicative of a patient being likely to develop abnormal deposit of ECMP, or fibrosis, especially hepatic fibrosis.

The presence of a C allele with respect to SNP rs2064501, more particularly of a CC genotype, is deleterious for the patient, i.e. it is indicative of a patient being likely to develop abnormal deposit of ECMP, or fibrosis, especially hepatic fibrosis.

SNPs in the same bins are highly correlated ($r^2>0.8$) and of similar utility in the methods of the invention. SNPs in strong linkage disequilibrium (yielding $r^2>0.6$) are encompassed as well.

Another method of the invention may comprise determining whether the patient comprises a genotype of non-response as defined in Table 1B.

Analysis was performed on 123 subjects (69 responder subjects and 54 non responder subjects), all infected with HCV.

TABLE 1B

Antiviral treatment response-associated alterations in the IL22RA2 gene locus

| Bin | SNP | SEQ ID NO: | Responder Genotype (RG) | % with RG in Responders | % with RG in Non Responders | p | OR | CI |
|-----|-----|------------|-------------------------|-------------------------|------------------------------|---|----|-----|
| | | | Univariate analysis | | | | | |
| I | rs7774663 | 10 | CT, TT | 89 | 79.3 | 0.13 | 2.1 | 0.8-5.6 |
| I | rs6570136 | 2 | AG, GG | 78.6 | 66.1 | 0.12 | 1.9 | 0.85-4.2 |
| II | rs7749054 | 15 | TT | 71.6 | 58.6 | 0.1 | 1.8 | 0.9-3.7 |
| III | rs202563 | 16 | AG, GG | 87.7 | 75.4 | 0.07 | 2.3 | 0.9-5.8 |
| IV | rs28366 | 21 | CC, TC | 44.6 | 32.1 | 0.15 | 1.7 | 0.8-3.5 |
| IV | rs276466 | 20 | | | | 0.3 | | |
| V | rs11154915 | 25 | TT | 6.8 | 1.7 | 0.2 | 4.2 | 0.5-37 |
| VI | rs2064501 | 37 | CT | 54.8 | 32.8 | 0.013 | 2.5 | 1.2-5.1 |
| VII | rs1543509 | 38 | AA | 90.5 | 73.2 | 0.012 | 3.5 | 1.3-9.3 |
| | | | Multivariate analysis | | | | | |
| I | rs6570136 | 2 | GG | | | 0.16 | 1.9 | 0.8-4.7 |
| V | rs11154915 | 25 | TT | | | 0.03 | 13.7 | 1.3-146 |
| VI | rs2064501 | 37 | CT | | | 0.004 | 3.6 | 1.5-8.5 |
| VII | rs1543509 | 38 | AA | | | 0.014 | 3.9 | 1.3-11.5 |

Preferably the method comprises genotyping a SNP selected in the group consisting of rs11154915, rs6570136, rs2064501 and rs1543509.

The presence of a TT genotype with respect to SNP rs11154915, is in favor of a patient's positive response to the antiviral treatment.

The presence of a AG or GG genotype with respect to SNP rs6570136, is in favor of a patient's positive response to the antiviral treatment.

The presence of a CT genotype with respect to SNP rs2064501, is in favor of a patient's positive response to the antiviral treatment The presence of a AA genotype with respect to SNP rs1543509, is in favor of a patient's positive response to the antiviral treatment.

SNPs in the same bins are highly correlated (r2>0.8) and of similar utility in the methods of the invention. SNPs in linkage disequilibrium are encompassed as well.

Odd ratios associated with each genotype are indicated in Table 1B. They vary from 1.9 to 4 when each SNP was evaluated alone; when all SNPs were evaluated together in the same multivariate model (that takes into account confounding effects between SNPs) ORs vary from 1.9 to 13, and a subjects who will carry responder genotypes for all four polymorphisms will be around 50 to 300 times more likely to respond to treatment that a subjects carrying non responder genotypes for all genotypes.

Linkage disequilibrium (LD) is defined as the non-random association of alleles at different loci across the genome. Alleles at two or more loci are in LD if their combination occurs more or less frequently than expected by chance in the population.

When there is a causal locus in a DNA region, due to LD, one or more SNPs nearby are likely associated with the trait too. Therefore, any SNPs in strong LD (yielding a r2>0.6) with a first SNP associated with an abnormal ECMP deposit will be associated with this trait.

Identification of additional SNPs in linkage disequilibrium with a given SNP involves: (a) amplifying a fragment from the genomic region comprising or surrounding a first SNP from a plurality of individuals; (b) identifying of second SNPs in the genomic region harboring or surrounding said first SNP; (c) conducting a linkage disequilibrium analysis between said first SNP and second SNPs; and (d) selecting said second SNPs as being in linkage disequilibrium with said first marker. Subcombinations comprising steps (b) and (c) are also contemplated.

Methods to identify SNPs and to conduct linkage disequilibrium analysis can be carried out by the skilled person without undue experimentation by using well-known methods.

It is well known that many SNPs have alleles that show strong LD with other nearby SNP alleles and in regions of the genome with strong LD, a selection of evenly spaced SNPs, or those chosen on the basis of their LD with other SNPs (proxy SNPs or Tag SNPs), can capture most of the genetic information of SNPs, which are not genotyped with only slight loss of statistical power. In association studies, this region of LD are adequately covered using few SNPs (Tag SNPs) and a statistical association between a SNP and the phenotype under study means that the SNP is a causal variant or is in LD with a causal variant. The two metrics most commonly used to measure LD are D' and $r^2$ and can be written in terms of each other and allele frequencies. It is a general consensus that a proxy (or Tag SNP) is defined as a SNP in LD ($r^2 \geq 0.8$) with one or more other SNPs. The genotype of the proxy SNP could predict the genotype of the other SNP via LD and inversely. In particular, any SNP in LD with one of the SNPs used herein may be replaced by one or more proxy SNPs defined according to their LD as $r^2 \geq 0.8$.

These SNPs in linkage disequilibrium can also be used in the methods according to the present invention, and more particularly in the diagnostic methods according to the present invention.

Alterations in the IL22RA2 gene may be detected by determining the presence of an altered IL22RA2 RNA expression. Altered RNA expression includes the presence of an altered RNA sequence, the presence of an altered RNA splicing or processing, the presence of an altered quantity of RNA, etc. These may be detected by various techniques known in the art, including by sequencing all or part of the IL22RA2 RNA or by selective hybridisation or selective amplification of all or part of said RNA, for instance.

In a further variant, the method comprises detecting the presence of an altered IL22RA2 polypeptide expression. Altered IL22RA2 polypeptide expression includes the presence of an altered polypeptide sequence, the presence of an altered quantity of IL22RA2 polypeptide, the presence of an altered tissue distribution, etc. These may be detected by various techniques known in the art, including by sequencing and/or binding to specific ligands (such as antibodies), for instance.

As indicated above, various techniques known in the art may be used to detect or quantify altered IL22RA2 gene or RNA expression or sequence, including sequencing, hybridisation, amplification and/or binding to specific ligands (such as antibodies). Other suitable methods include allele-specific oligonucleotide (ASO), allele-specific amplification, Southern blot (for DNAs), Northern blot (for RNAs), single-stranded conformation analysis (SSCA), PFGE, fluorescent in situ hybridization (FISH), gel migration, clamped denaturing gel electrophoresis, heteroduplex analysis, RNase protection, chemical mismatch cleavage, ELISA, radio-immunoassays (RIA) and immuno-enzymatic assays (IEMA). Some of these approaches (e.g., SSCA and CGGE) are based on a change in electrophoretic mobility of the nucleic acids, as a result of the presence of an altered sequence. According to these techniques, the altered sequence is visualized by a shift in mobility on gels. The fragments may then be sequenced to confirm the alteration. Some others are based on specific hybridization between nucleic acids from the subject and a probe specific for wild-type or altered IL22RA2 gene or RNA. The probe may be in suspension or immobilized on a substrate. The probe is typically labelled to facilitate detection of hybrids. Some of these approaches are particularly suited for assessing a polypeptide sequence or expression level, such as Northern blot, ELISA and RIA. These latter require the use of a ligand specific for the polypeptide, more preferably of a specific antibody.

In a preferred embodiment, the method comprises detecting the presence of an altered IL22RA2 gene expression profile in a sample from the subject. As indicated above, this can be accomplished more preferably by sequencing, selective hybridisation and/or selective amplification of nucleic acids present in said sample.

Sequencing

Sequencing can be carried out using techniques well known in the art, using automatic sequencers. The sequencing may be performed on the complete IL22RA2 gene locus or, more preferably, on specific domains thereof, typically those known or suspected to carry deleterious mutations or other alterations.

Amplification

Amplification is based on the formation of specific hybrids between complementary nucleic acid sequences that serve to initiate nucleic acid reproduction. Amplification may be performed according to various techniques known in the art, such as by polymerase chain reaction (PCR), ligase chain reaction (LCR), strand displacement amplification (SDA) and nucleic acid sequence based amplification (NASBA). These techniques can be performed using commercially available reagents and protocols. Preferred techniques use allele-specific PCR or PCR-SSCP. Amplification usually requires the use of specific nucleic acid primers, to initiate the reaction. Nucleic acid primers useful for amplifying sequences from the IL22RA2 gene locus are able to specifically hybridize with a portion of the IL22RA2 gene locus that flank a target region of said locus, said target region being altered in certain subjects having fibrosis or associated disorders.

This invention makes use of nucleic acid primers useful for amplifying sequences from the IL22RA2 gene or locus including surrounding regions. Such primers are preferably complementary to, and hybridize specifically to nucleic acid sequences in the IL22RA2 gene locus. Particular primers are able to specifically hybridize with a portion of the IL22RA2 gene locus that flank a target region of said locus, said target region being altered in certain subjects having fibrosis or associated disorders.

Selective Hybridization

Hybridization detection methods are based on the formation of specific hybrids between complementary nucleic acid sequences that serve to detect nucleic acid sequence alteration(s). A particular detection technique involves the use of a nucleic acid probe specific for wild-type or altered IL22RA2 gene or RNA, followed by the detection of the presence of a hybrid. The probe may be in suspension or immobilized on a substrate or support (as in nucleic acid array or chips technologies). The probe is typically labeled to facilitate detection of hybrids. In this regard, a particular embodiment of this invention comprises contacting the sample from the subject with a nucleic acid probe specific for an altered IL22RA2 gene locus, and assessing the formation of a hybrid. In a particular preferred embodiment, the method comprises contacting simultaneously the sample with a set of probes that are specific, respectively, for wild type IL22RA2 gene locus and for various altered forms thereof. In this embodiment, it is possible to detect directly the presence of various forms of alterations in the IL22RA2 gene locus in the sample. Also, various samples from various subjects may be treated in parallel.

Within the context of this invention, a probe refers to a polynucleotide sequence which is complementary to and capable of specific hybridization with a (target portion of a) IL22RA2 gene or RNA, and which is suitable for detecting polynucleotide polymorphisms associated with IL22RA2 alleles which predispose to or are associated with fibrosis. Probes are preferably perfectly complementary to the IL22RA2 gene, RNA, or target portion thereof. Probes typically comprise single-stranded nucleic acids of between 8 to 1000 nucleotides in length, for instance of between 10 and 800, more preferably of between 15 and 700, typically of between 20 and 500. It should be understood that longer probes may be used as well. A preferred probe of this invention is a single stranded nucleic acid molecule of between 8 to 500 nucleotides in length, which can specifically hybridize to a region of a IL22RA2 gene locus or RNA that carries an alteration.

The method of the invention employs a nucleic acid probe specific for an altered (e.g., a mutated) IL22RA2 gene or RNA, i.e., a nucleic acid probe that specifically hybridizes to said altered IL22RA2 gene or RNA and essentially does not hybridize to a IL22RA2 gene or RNA lacking said alteration. Specificity indicates that hybridization to the target sequence generates a specific signal which can be distinguished from the signal generated through non-specific hybridization. Perfectly complementary sequences are preferred to design probes according to this invention. It should be understood, however, that certain mismatch may be tolerated, as long as the specific signal may be distinguished from non-specific hybridization. Particular examples of such probes are nucleic acid sequences complementary to a target portion of the genomic region including the IL22RA2 gene locus or RNA carrying a point mutation as listed in Table 1 above.

The sequence of the probes can be derived from the sequences of the IL22RA2 gene and RNA as provided in the present application. Nucleotide substitutions may be performed, as well as chemical modifications of the probe. Such chemical modifications may be accomplished to increase the stability of hybrids (e.g., intercalating groups) or to label the probe. Typical examples of labels include, without limitation, radioactivity, fluorescence, luminescence, enzymatic labelling, etc. The invention also concerns the use of a nucleic acid probe as described above in a method of detecting the presence of or predisposition to fibrosis or an associated disorder in a subject or in a method of assessing the response of a subject to a treatment of fibrosis or an associated disorder.

Specific Ligand Binding

As indicated above, alteration in the IL22RA2 gene locus may also be detected by screening for alteration(s) in IL22RA2 polypeptide sequence or expression levels. In this regard, contacting the sample with a ligand specific for a IL22RA2 polypeptide and determining the formation of a complex is also described. Different types of ligands may be used, such as specific antibodies. In a specific embodiment, the sample is contacted with an antibody specific for a IL22RA2 polypeptide and the formation of an immune complex is determined. Various methods for detecting an immune complex can be used, such as ELISA, radio-immunoassays (RIA) and immuno-enzymatic assays (IEMA). Within the context of this invention, an antibody designates a polyclonal antibody, a monoclonal antibody, as well as fragments or derivatives thereof having substantially the same antigen specificity. Fragments include Fab, Fab'2, CDR regions, etc. Derivatives include single-chain antibodies, humanized antibodies, poly-functional antibodies, etc. An antibody specific for a IL22RA2 polypeptide designates an antibody that selectively binds a IL22RA2 polypeptide, i.e., an antibody raised against a IL22RA2 polypeptide or an epitope-containing fragment thereof. Although non-specific binding towards other antigens may occur, binding to the target IL22RA2 polypeptide occurs with a higher affinity and can be reliably discriminated from non-specific binding.

It is also disclosed a diagnostic kit comprising products and reagents for detecting in a sample from a subject the presence of an alteration in the IL22RA2 gene locus or polypeptide, in the IL22RA2 gene or polypeptide expression, and/or in IL22RA2 activity. Said diagnostic kit comprises any primer, any pair of primers, any nucleic acid probe and/or any ligand, preferably antibody, described in the present invention. Said diagnostic kit can further comprise reagents and/or protocols for performing a hybridization, amplification or antigen-antibody immune reaction.

Drug Screening

New methods for the screening of drug candidates or leads are also described. These methods include binding assays and/or functional assays, and may be performed in vitro, in cell systems, in animals, etc. A particular object of this invention resides in a method of selecting biologically active compounds, said method comprising contacting in vitro a test compound with a IL22RA2 gene or polypeptide according to the present invention and determining the ability of said test compound to bind said IL22RA2 gene or polypeptide. Binding to said gene or polypeptide provides an indication as to the ability of the compound to modulate the activity of said target, and thus to affect a pathway leading to any abnormal deposit of ECMP or fibrosis in a subject. In a preferred embodiment, the method comprises contacting in vitro a test compound with a IL22RA2 polypeptide or a fragment thereof according to the present invention and determining the ability of said test compound to bind said IL22RA2 polypeptide or fragment. The fragment preferably comprises a binding site of the IL22RA2 polypeptide. Preferably, said IL22RA2 gene or polypeptide or a fragment thereof is an altered or mutated IL22RA2 gene or polypeptide or a fragment thereof comprising the alteration or mutation. A particular object of this invention resides in a method of selecting compounds active on any abnormal deposit of ECMP or fibrosis, said method comprising contacting in vitro a test compound with a IL22RA2 polypeptide according to the present invention or binding site-containing fragment thereof and determining the ability of said test compound to bind said IL22RA2 polypeptide or fragment thereof. Preferably, said IL22RA2 polypeptide or a fragment thereof is an altered or mutated IL22RA2 polypeptide or a fragment thereof comprising the alteration or mutation. The method for the screening of drug candidates comprises contacting a recombinant host cell expressing a IL22RA2 polypeptide according to the present invention with a test compound, and determining the ability of said test compound to bind said IL22RA2 and to modulate the activity of IL22RA2 polypeptide. Preferably, said IL22RA2 polypeptide or a fragment thereof is an altered or mutated IL22RA2 polypeptide or a fragment thereof comprising the alteration or mutation. The determination of binding may be performed by various techniques, such as by labelling of the test compound, by competition with a labelled reference ligand, etc. The method of selecting biologically active compounds also comprises contacting in vitro a test compound with a IL22RA2 polypeptide and determining the ability of said test compound to modulate the activity of said IL22RA2 polypeptide. Preferably, said IL22RA2 polypeptide or a fragment thereof is an altered or mutated IL22RA2 polypeptide or a fragment thereof comprising the alteration or mutation. The method of selecting biologically active compounds for a subject that has or is predisposed to develop any abnormal deposit of ECMP or fibrosis, also comprises contacting in vitro a test compound with a IL22RA2 gene according to the present invention and determining the ability of said test compound to modulate the expression of said IL22RA2 gene. Preferably, said IL22RA2 gene or a fragment thereof is an altered or mutated IL22RA2 gene or a fragment thereof comprising the alteration or mutation.

The method of screening, selecting or identifying active compounds, particularly compounds active on any abnormal deposit of ECMP or fibrosis, also comprises contacting a test compound with a recombinant host cell comprising a reporter construct, said reporter construct comprising a reporter gene under the control of a IL22RA2 gene promoter, and selecting the test compounds that modulate (e.g. activate or inhibit) expression of the reporter gene. Preferably, said IL22RA2 gene promoter or a fragment thereof is an altered or mutated IL22RA2 gene promoter or a fragment thereof comprising the alteration or mutation.

The above screening assays may be performed in any suitable device, such as plates, tubes, dishes, flasks, etc. Typically, the assay is performed in multi-wells plates. Several test compounds can be assayed in parallel. Furthermore, the test compound may be of various origin, nature and composition. It may be any organic or inorganic substance, such as a lipid, peptide, polypeptide, nucleic acid, small molecule, etc., in isolated or in mixture with other substances. The compounds may be all or part of a combinatorial library of products, for instance.

Further aspects and advantages of the present invention will be disclosed in the following experimental section, which should be regarded as illustrative and not limiting the scope of the present application.

EXAMPLES

Figure 1A:
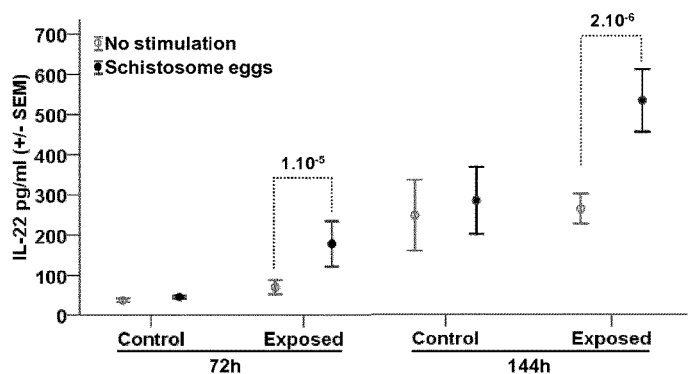
FIGS. 1A and 1B show IL-22 and IL-17 levels in cultures of PBMC from *S. japonicum* endemic subjects Data are obtained in 144 hrs resting and egg-stimulated cultures from 19 controls and 70 endemic subjects
Figure 1B:
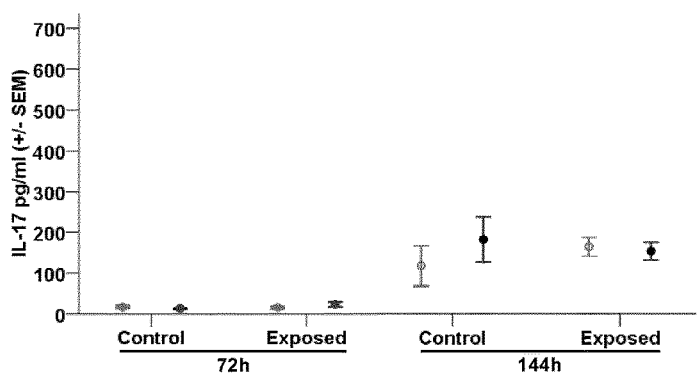
Figure 1C:
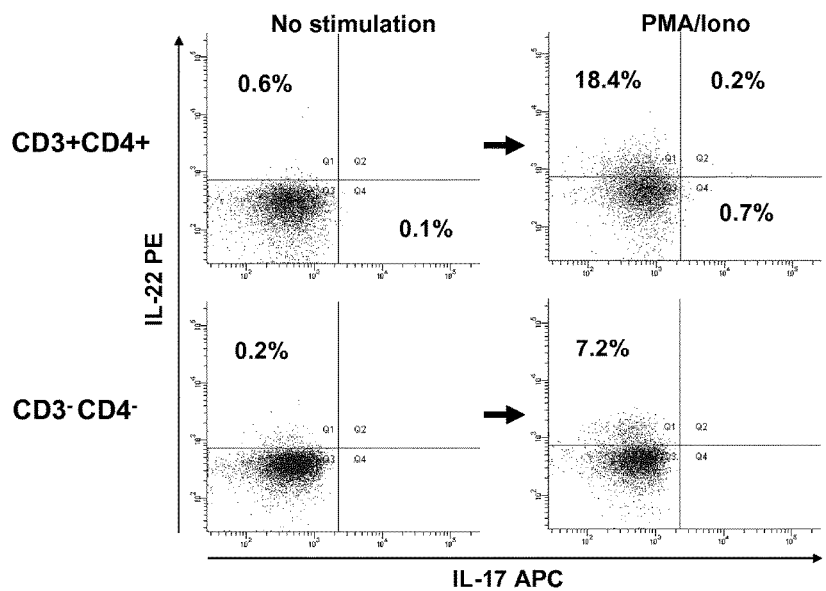
FIG. 1C shows FACS analysis of IL22+ cells from the blood of endemic subjects. Data are from one representative experiment out of 20.

Example 1: Production and Modulation of IL-22 in Human Schistosome Infections Production of IL-22 in Human Schistosome Infections The inventors have compared IL-22 levels in cultures of PBMC from 140 subjects exposed to *S. japonicum* infections with cultures of 20 controls who had no previous exposure to schistosome infections (FIG. 1A) but lived in the same region in comparable living conditions. IL-22 was detected in resting cultures of exposed subjects at 72 and 144 hrs and was significantly enhanced by addition of schistosome eggs at time 0 of the culture. IL-22 was detected in control resting cultures at 144 hrs only and was not enhanced by addition of eggs. The inventors detected significant IL-17A levels in 144 hrs cultures but IL-17 levels were not enhanced by egg-stimulation (FIG. 1B). Thus it is unlikely that IL-22 in the cultures was produced by Th17. Analysis by FACS of the IL22+ cells in the blood of exposed patients showed IL-22 is produced by CD3+CD4+ and by CD3−CD4− none of these cells populations produced IL-17 (FIG. 1C). The latter likely are NK cells. The percentage of CD3+CD4+IL17−IL22+ T cells and CD3−CD4−IL17−IL22+ in control and endemic subjects are shown on FIG. 1C.

Modulation of IL-22 production is modified by the anti-schistosome treatment and is modulated accordingly to hepatic fibrosis.

IL-22 levels in egg-stimulated cultures varied markedly among exposed subjects. Since anti-schistosome Praziquantel treatments destroy the worms and shut off egg production until reinfection occurs, we evaluated whether differences in Praziquantel treatments could have modulated IL-22 production. Certain patients had been treated every year for at least 10 years, others had never been treated and others had received 1 to 10 treatments in the past 10 years. FIG. 2A shows the number of Praziquantel treatments had a significant impact on IL-22 production by subjects PBMC: IL-22 in egg-stimulated cultures augmented significantly with the number of treatments over the past ten years ($p=0.005$, covariate in the regression model was gender $p=0.08$); this effect was however much less for subjects who had been treated at least once a year every year probably because these subjects were not getting reinfected (see below). Then the frequency of Praziquantel treatments over the last ten years had impacted significantly on IL-22 production by PBMC from exposed subjects.

The inventors then evaluated whether IL-22 levels in cultures were related to the degree of patient's liver disease. FIG. 2B shows that IL-22 was low in subjects with mild liver disease as measured by hepatic fibrosis grades and augmented steadily with increased fibrosis grades reaching maximum levels in subjects with advanced central periportal fibrosis. This suggests that increased production of IL-22 may occur in response to/in association with severe hepatic disease. Strikingly, however, IL-22 from patients with very severe hepatic fibrosis (HF grades D,E,F) failed to produce much IL-22.

The effect of the number of Praziquantel treatments on this pattern is shown on FIG. 2C. Praziquantel treatments impacted IL-22 produced by cells from all fibrosis groups. Three observations are most relevant to our study: first the increase IL-22 production in advanced fibrosis (CLH) is observed at different Praziquantel regimens and is not due to differences in the frequency of treatment of this patients; second, Praziquantel treatments improved IL-22 production in all cultures but in cultures of cells from subjects with severe fibrosis grades; third, subjects with the high Praziquantel regimens (>10, once at least every year) are in the mild fibrosis group and account for the increase of IL-22 production observed in this group. In summary, IL-22 is impacted by two independent factors the Praziquantel treatments and the degree of hepatic disease. Moreover subjects with very severe hepatic disease fail to produce much IL-22 and this was not improved by Praziquantel treatments whereas the same treatments had a marked enhancing effect on IL-22 production by subjects with mild to advanced hepatic fibrosis.

IL-6 and possibly IL-1β likely are key regulators of IL-22 production in subjects with different hepatic fibrosis grades and different treatment regimens.

The inventors observed that cytokines IL-6, IL-1β and IL-23 were significantly enhanced (IL-23 (p=3.10-6), IL-6 (p<10-6) and IL-1β (p<10-6) by egg stimulation in 24 hrs cultures of PBMC from exposed subjects (FIG. 3A). To determine whether any of these 3 cytokine could play a role in modulating IL-22 levels, we performed a linear regression analysis with IL-22 levels in egg-stimulated cultures including these 3 cytokines, patient age and gender. This analysis showed a highly significant (p=0.0002) association between IL-22 and IL-6 and a weak association (p=0.06) with IL-1β. IL-23 was excluded from the regression model. This result is illustrated in FIGS. 3B, 3C that shows the variations of IL-6, IL-1β, and IL-23 with Praziquantel treatments (FIG. 3B) and with hepatic fibrosis (FIG. 3C). Thus, the link between Praziquantel treatments and IL-22 and Fibrosis grades and IL-22 is, at least in part, IL-6.

The results presented above are consistent with the view that the recruitment of a protective IL-22 response increased with hepatic damage and that the most severe hepatic disease may result in part from the inability to recruit such response. To test further this hypothesis the inventors looked for genetic evidence indicating the IL-22 was indeed crucial in the control of hepatic fibrosis and had a significant impact on hepatic disease.

Example 2: Polymorphisms in IL22RA2 Encoding IL22 BP are Associated with Hepatic Fibrosis in Two Samples of Chinese Fishermen and Farmers Living in an Endemic Area of S. japonicum Materials and Methods
Statistical Analysis Multivariate logistic regression was used to analyse the relationship between the probability of an individual developing fibrosis and genetic variants including the main covariates known to affect disease progression in subjects infected with schistosomes. The statistical SPSS software (version 10.0) was used for this analysis. Age, gender, and exposure to infection, were tested in the regression models and kept when they showed an association (p<0.05) with disease. Since the cohorts were matched for gender and age, these covariates had little effects on the association between genetic variants and disease. Infection with HBV and exposure to infection were included in the regression models when these covariates could be evaluated accurately as in the Chinese fishermen (exposure, number of treatments) or in the Chinese farmers (HBV infection, place of birth).

DNA Extraction

Aliquots of 5 to 15 ml of blood were collected on sodium citrate and kept at −20° C. DNA was extracted using the standard salting out method (Sambrook et al., 1989).

DNA Amplification

All the DNA purified from FTA card were pre amplified before genotyping. Polymerase chain reactions (whole genome amplifications) were conducted in 50 μl reactions containing one punch of biological sample (FTA1-bound buccal cell DNA) or 100 ng of genomic DNA, 1.5 OD of 15-base totally degenerate random primer (Genetix, Paris, France), 200 mM dNTPs, 5 mM $MgCl_2$, 5 ml of 10×PCR buffer and 0.5 unit of high fidelity Taq DNA polymerase (BIOTAQ DNA Polymerase, Bioline London, England). Samples were amplified in a multiblock thermocycler as follows: a pre-denaturation step of 3 min at 94° C., 50 cycles consisting of 1 min at 94° C., 2 min at 37° C., 1 min of ramp (37-55° C.), and 4 min at 55° C. Final extension step of 5 min at 72° C.

Sequencing

Purified PCR products were sequenced using ABI Prism BigDye Terminator cycle sequencing system (PE Applied Biosystems, Foster City, U.S.A.) on ABI Prism automatic sequencer. Sequencing reactions were performed on both strands Sequencing by GATC biotech (GATC, Marseille France).

Polymorphism Genotyping by PCR with Specific TaqMan Probes

Allelic discrimination was assessed using TaqMan probe assays (Applied Biosystems, Lafayette USA). Each reaction contained 12.5 ng of genomic DNA, TaqMan Universal PCR Master Mix (Applied Biosystems, Lafayette USA), 900 nM of each primer and 200 nM of each fluorescently-labelled hybridisation probe in a total volume of 5 μl. RT-PCR was conducted in an ABI Prism Sequence Detection System 7900 (Applied Biosystems, Lafayette USA) using the following conditions: 50° C. for 2 min, 95° C. for 10 min and 40 cycles of amplification (95° C. denaturation for 15 s, 60° C. annealing/extension for 1 min).

Results

The inventors have selected in HapMap data basis the SNPs comprise in IL22RA2 (29.7 Kb) and 10 Kb in 3' and 5' of the gene that had a Minor allele frequency in Chinese greater than 10%. These SNPs were grouped in six correlation ($r^2$=0.8) bins containing n=10 (bin I), 5 (II), 2 (III), 3 (IV), 13 (V) and 3 (VI), and 4 singletons which are positioned as in FIG. 4. The inventors genotyped one or two SNPs from each bins in a sample of Chinese fishermen (n=268, 176 subjects with mild HF and 92 patients with severe HF) who have been fishing for at least 20 years in the Dong Ting lake where S. japonicum has been endemic for at least 40 years. They found that 3 SNPs belonging to two bins were associated with HF. SNP rs6570136 GG (p=0.007, OR=2.7 (CI=1.3-5.6)), rs7774663 TT (p=0.006, OR=2.5 (1.3-4.7)) both in bin I and rs7749054 TT (p=0.045, OR=1.8 (1.1-3.1)) showed some association with HF (Table 2). The significant covariates introduced in the statistical model, were gender (p<10-3, OR=6.9 (2.8-17)), Exposure (Number of fishing years) (p=0.05, OR=1.02 (1-1.05)), splenectomy (p=0.008, OR=6.6 (1.6-27)). Multivariate analysis testing two SNPs simultaneously in the same models in the presence of the same covariates indicated that SNPrs 11154915 TC was associated (p=0.04, OR=1.9 (1-3.5)) when tested in the presence of rs 6570136 (p=0.007 OR=2.9 (1.4-6). Interestingly (see study in Sudanese and Brazilians) SNP rs 2064501 showed a trend to association with HF that was not reduced when other SNPs were introduced in the regression model.

Finally, the association of rs7749054 was likely due to its LD with SNPs in bin I since the association of rs7749054 with HF was totally lost in the presence of either SNP rs6570136 or SNP rs7774663.

TABLE 2

SNPs of IL22RA2 associated with Hepatic fibrosis: analysis in Chinese fishermen

| | SNP | Position | Bin | Genotype | Controls % | Cases % | OR | 95% CI | p |
|---|---|---|---|---|---|---|---|---|---|
| Univariate analysis | rs6570136 | 137536315 | I | GG | 13.0 | 22.1 | 2.7 | 1.3-5.6 | 0.007 |
| | rs7774663 | 137552586 | I | TT | 18.1 | 28.4 | 2.5 | 1.3-4.7 | 0.006 |
| | rs7749054 | 137542479 | II | TT | 32.8 | 41.1 | 1.8 | 1.0-2.9 | 0.045 |
| | rs202563 | 137503185 | III | AA | 38.7 | 45.8 | | | 0.3 |
| | rs276466 | 137508307 | IV | AG + GG | 24.3 | 30.2 | | | >0.5 |
| | rs11154915 | 137524675 | V | CT (no TT) | 97.2 | 99.1 | | | 0.16 |
| | rs2064501 | 137519516 | VI | CC + TT | 55.4 | 62.5 | | | 0.17 |
| Multivariate analysis Model 1 | rs6570136 | | I | GG | | | 2.9 | 1.4-6.0 | 0.007 |
| | rs11154915 | | V | CT (no TT) | | | 1.9 | 1.0-3.5 | 0.04 |

(n = 268, 92 cases and 176 controls)

The inventors then attempted to replicate these results in a second Chinese sample from farmers from a region endemic for *S. japonicum*. This sample differs from the fisherman sample because it was hospital based recruited from an outpatient clinic caring for severe hepatic disease including ascites, bleeding from varices and cirrhosis. 92.2% of the recruited patients were living in a region where *S. japonicum* was still endemic, 7.8% had been living in a schistosome endemic region but transmission in their region had been interrupted ten to fifteen years ago. A fraction (86.5%) of these subjects had evidence of previous HBV infection (20.9% AgHBS+) one patient had been infected with HCV. Thus liver disease in most farmers of this second sample likely results from both schistosome and HBV infections.

All SNPs tested in the Fisherman sample were genotyped on the Farmer sample (298, 97 subjects with mild hepatic disease and 201 subjects with severe hepatic disease). Association with hepatic disease was observed with 4 SNPs from 3 different bins: SNP rs6570136 GG,GA (p=0.009, OR=2 (1.2-3.3)), rs7774663 TT,TC (p=0.01, OR=2 (1.2-3.3)) both in bin I; SNP rs 276466 GA (p=0.01, OR=2.2 (1.2-4)) in bin IV; SNP rs1114915 CC,CT (p=0.04, OR=5.7 (1.1-29.6)) in bin V (Table 3). Trends for association were also observed for SNP rs202563 AA,GG (p=0.06) in bin III and SNP rs2064501 CT (p=0.08). Covariates in these association test were Age (p=0.05, OR=1.03 (1-1.06), gender (p=0.02, OR=2.3 (1.1-4.8) and whether the patient was living in endemic/non endemic region (p=0.09, OR=2). Multivariate analysis performed on SNPs from different bins indicated two possible statistical models: one model included SNPs rs6570136 (or rs7774663) (p=0.03, OR=1.8 (1.1-3)) in bin I and SNP rs11154915 (p=0.1, OR=4 (0.8-21.2)) in bin V; the other model included SNP rs 276466 (p=0.02, OR=2 (1.1-3.8)) and SNP rs11154915 (p=0.05, OR=9.2 (1.1-80)). The analysis could not discriminate between these two models.

TABLE 3

SNPs of IL22RA2 associated with Hepatic fibrosis; analysis in Chinese farmers

| | | | | | Chinese farmer sample | | | | |
|---|---|---|---|---|---|---|---|---|---|
| | SNP | Position | Bin | Genotype | Controls % | Cases % | OR | 95% CI | p |
| Univariate analysis | rs6570136 | 137536315 | I | GG + AG | 53.6 | 67.8 | 2 | 1.2-3.3 | 0.009 |
| | rs7774663 | 137552586 | I | CT + TT | 58.8 | 72.3 | 2 | 1.2-3.3 | 0.01 |
| | rs7749054 | 137542479 | II | GG | 15.1 | 18.9 | | | 0.5 |
| | rs202563 | 137503185 | III | AA + GG | 46.9 | 57.3 | 1.6 | 0.98-2.7 | 0.06 |
| | rs276466 | 137508307 | IV | AG (no GG) | 18.7 | 34.5 | 2.2 | 1.2-4.0 | 0.01 |
| | rs11154915 | 137524675 | V | CC + CT | 93.8 | 99.3 | 5.7 | 1.1-29.6 | 0.036 |
| | rs2064501 | 137519516 | VI | CT | 40.2 | 51.2 | 1.6 | 0.95-2.7 | 0.08 |
| Multivariate analysis | rs6570136 | | I | GG + AG | | | 1.6 | 1-2.6 | 0.06 |
| Model 1 | rs11154915 | | V | CT + TT | | | 4.8 | 0.93-25 | 0.06 |

(n = 298, 201 cases and 97 controls)

Example 3: Extension of the Association to Populations from Sudan and Brazil Exposed to *Schistosoma mansoni*

To assess whether our observation could be extended to subjects infected with *S. mansoni* we tested the same SNPs in a sample from Sudan and in a sample from Brazil. Again a significant fraction of subjects in the Sudanese sample as in the Chinese farmer had also been infected with HBV whereas only very few Brazilian had HBV infections.

Genotyping the Sudanese sample (n=202, 144 mild HF and 58 severe HF) showed that SNP rs6570136 GG (p=0.01, OR=3.1 (1.3-7.2)), rs7774663 TT,TC (p=0.01, OR=1.7 (1-3.1), rs11154915 TT (p=0.05, OR=6.2 (1-35.3)) showed associations with HF whereas a trend for association was also detected for SNPrs7749054 TT (p=0.07, OR=2 (1-3.6) and for rs2064501 CC (p=0.06, OR=2.7 1-7.3)). See Table 4.

TABLE 4

Extension of the associations detected in Chinese to Sudanese infected with *S. mansoni*

| | | | | | Sudanese sample | | | | |
|---|---|---|---|---|---|---|---|---|---|
| | SNP | Position | Bin | Genotype | Controls % | Cases % | OR | 95% CI | p |
| Univariate analysis | rs6570136 | 137536315 | I | GG | 8.3 | 24.5 | 3.1 | 1.3-7.2 | 0.006 |
| | rs7774663 | 137552586 | I | CC + TT | 45.5 | 66.7 | 1.7 | 1-3.1 | 0.04 |
| | rs7749054 | 137542479 | II | TT | | | | | 0.2 |
| | rs202563 | 137503185 | III | GG | 21.8 | 34 | 1.6 | 0.9-3.0 | 0.09 |
| | rs276466 | 137508307 | IV | AG + GG | | | | | 0.25 |
| | rs11154915 | 137524675 | V | TT | 0.8 | 5.7 | 6.2 | 1-35.3 | 0.07 |
| | rs2064501 | 137519516 | VI | CC + TT | 5.3 | 17 | 2.6 | 1.2-5.7 | 0.02 |
| Multivariate analysis | rs6570136 | | I | GG | | | 10 | 3-34 | 0.0002 |
| Model 1 | rs2064501 | | VI | TT | | | 3.4 | 1.2-9.4 | 0.018 |
| | rs11154915 | | V | TT | | | 7.4 | 0.75-74 | 0.09 |

(n = 189, 53 cases and 133 controls)

Likewise genotyping these same SNPs in the Brazilian sample (n=161, 119 mild HF and 42 severe HF) showed association with HF for SNP rs6570136 GG (p=0.0001, OR=6 (2.4-14.7)), rs7774663 TT (p=0.03, OR=3 (1.4-6.8)) and SNPrs7749054 TT (p=0.03, OR=2.8 (1.2-5.6), Furthermore rs11154915 TT,TC showed a trend for association with HF (p=0.14, OR=2.4 (0.9-6.5)).

See Table 5:

TABLE 5

Replication of the association in Brazilians infected with *S. mansoni*

| | | | | | Brazilian sample | | | | |
|---|---|---|---|---|---|---|---|---|---|
| | SNP | Position | Bin | Genotype | Controls % | Cases % | OR | 95% CI | p |
| Univariate analysis | rs6570136 | 137536315 | I | GG | 11.5 | 35.6 | 4.2 | 1.8-10 | 0.001 |
| | rs7774663 | 137552586 | I | TT | 24.5 | 44.2 | 2.4 | 1.2-5.1 | 0.02 |

TABLE 5-continued

Replication of the association in Brazilians infected with *S. mansoni*

| | SNP | Position | Bin | Genotype | Brazilian sample | | | | |
|---|---|---|---|---|---|---|---|---|---|
| | | | | | Controls % | Cases % | OR | 95% CI | p |
| | rs7749054 | 137542479 | II | TT | 45.5 | 67.4 | 2.5 | 1.2-5.1 | 0.01 |
| | rs202563 | 137503185 | III | AG + GG | 73.5 | 86 | | | 0.13 |
| | rs276466 | 137508307 | IV | AG + GG | 26.5 | 41.9 | 2 | 0.9-4.3 | 0.07 |
| | rs11154915 | 137524675 | V | CT + TT | 74.3 | 87 | 2.3 | 0.9-6 | 0.09 |
| | rs2064501 | 137519516 | VI | CT + TT | 52.8 | 66.7 | | | 0.15 |
| Multivariate analysis | rs6570136 | | I | GG | | | 24.8 | 3-205 | 0.003 |
| | rs2064501 | | VI | CT + TT | | | 10.1 | 1.1-93 | 0.04 |
| | rs11154915 | | V | CT + TT | | | 2.3 | 0.8-6.9 | 0.14 |

Multivariate analysis performed in the Sudanese sample confirmed the independent associations of SNP rs6570136, 20564501 and 11154915. It was most remarkable that the high OR associated with rs11154915 was confirmed in the multivariate model. Furthermore subjects bearing the aggravating genotypes for both SNPs had in both models OR for HF greater than 25. The Multivariate analysis showed that the association of SNPs rs7749054 was lost in the presence of SNP rs6570136 confirming that this association was not independent of SNP rs6570136

In summary SNPs rs6570136 GG and rs7774663 TT, that belong to the same correlation bin were associated with HF, in all four samples tested. SNPrs11154915 TT, CT and rs2064501 CC showed a trend for association with HF in all samples; more important these trends were confirmed by multivariate analysis showing that these SNPs were acting independently of SNP rs6570136; taking into account these 2 SNPs increased the strength of the association of SNPrs6570136 with HF.

Example 4: Associations Between SNPs in IL22RA2 and Response to Anti-HCV Treatment The inventors have performed their genetic analysis on 123 subjects (69 responders to treatment with ribavirin+IFN, 54 non responders) who were or have been infected with HCV genotypes 1 or 4. They tested at least one SNP in each of the 7 bins identified in IL22RA2 using Hapmap data. Univariate analysis showed associations with SNP rs2064501 (bin VI, p=0.013) and SNP rs1543509 (bin VII, p=0.012) but also suggested possible associations with SNPs rs7774663, rs6570136 (bin I, p<0.13), SNP rs77449054 (bin II, p=0.1), SNP rs202563 (bin III, p=0.07), SNP rs28366 (bin IV p=0.15), and SNP rs2064501 (bin VI, p=0.2). This high number of SNPs in possible associations with response to treatment could be due to correlations between the tested SNPs, it also suggested that the different SNPs could exert confounding effects on each others. Then a step by step multivariate analysis was undertaken.

Testing all SNPs two by two indicated that the association of SNP rs202563 and rs6570136 with response to treatment were equivalent but that SNPs rs276466 and rs28366 were clearly excluded from the regression model by SNP rs6570136. All tests showed that the association of SNP rs11154915 with response to treatment was enhanced by the presence of other SNPs (like SNP rs6570136 or SNP rs2064501 or SNP rs1543509) in the regression model. The association of rs6570136 with response to treatment was lost in the presence of SNPs rs2064501 or rs1543509 but this association was regained when SNP rs11154915 was added to the model (3 SNPs in the model). This is due to the strong linkage disequilibrium between SNP rs11154915 and SNP rs6570136 (or any SNPs in bin I), as a consequence SNP rs11154915 TT responder genotype is 100% associated with bin I's non responder genotypes. So the model must include at least 3 SNPs (rs11154915 (p=0.03), rs7774663 (or rs6570136, p=0.03) and SNP rs2064501 (p=0.001). Finally SNP rs1543509 and SNPs from bin I (p=0.15) also enter in this model.

In summary the inventors have found that SNPs that belong to four different bins in IL22RA2 are independently associated with the response to treatment. Importantly, these results that were obtained testing TagSNPs, can be extended to any SNP in the same bins. Then it is expected that most if not all SNPs in bins I, V, VI and VII are genetic markers response to IFN+ribavirin treatment. It can also be seen that 3 of these identified bins were associated with fibrosis progression (SNPS in bin VII have not been tested on fibrosis yet). Interestingly, most genotypes that aggravate hepatic fibrosis are associated with a better response to treatment.

REFERENCES

Bedossa P., Poynard, T. The METAVIR cooperative study group. An algorithm for the grading of activity in chronic hepatitis C, Hepatology 1996; 24:289-293.

Dessein, A. J., D. Hillaire, N. E. Elwali, S. Marquet, Q. Mohamed-Ali, A. Mirghani, S. Henri, A. A. Abdelhameed, O. K. Saeed, M. M. Magzoub, and L. Abel. 1999. Severe hepatic fibrosis in *Schistosoma mansoni* infection is controlled by a major locus that is closely linked to the interferon-gamma receptor gene. Am J Hum Genet 65:709.

EASL Clinical Practice Guideline: Management of hepatitis C virus infection, J. Hepatol. 2011; 55:245-264

Fried M W et al; N Engl J. Med. 2002; 347(13):975-82

Mohamed-Ali Q, Elwali N E, Abdelhameed A A, Mergani A, Rahoud S, Elagib K E, Saeed O K, Abel L, Magzoub M M, Dessein A J. Susceptibility to periportal (Symmers) fibrosis in human *schistosoma mansoni* infections: evidence that intensity and duration of infection, gender, and inherited factors are critical in disease progression. J Infect Dis. 1999 October; 180(4):1298-306. PMID: 10479161

Parkes J, Guha I N, Roderick P et al. Performance of serum marker panels for liver fibrosis in hepatitis C. J Hepatol 2006; 44: 462-474.

Sebastiani G, Vario A, Guido M et al. Stepwise combination algorithms of non-invasive markers to diagnose significant fibrosis in chronic hepatitis C. J Hepatol 2006; 44: 686-693.

Testino G et al; Hepatogastroenterology 2011; 58(106): 536-8

Ziol M, et al. Noninvasive assessment of liver fibrosis by measurement of stiffness in patients with chronic hepatitis C. Hepatology 2005; 41:48-54.

The invention claimed is:

1. A non-invasive method of preventing or reducing the progression of fibrosis, comprising:
    a) obtaining a biological sample from a human subject, wherein the human subject has been infected with a hepatic virus or a parasite;
    b) detecting at least one single nucleotide polymorphism in a IL22RA2 gene locus of the biological sample, wherein the single nucleotide polymorphism is rs2064501 having a genotype of TT; and
    c) treating the human subject with an anti-fibrotic therapy.

2. The method of claim 1, wherein the human subject self-identifies as being Chinese, Brazilian, or Sudanese.

3. The method according to claim 1, wherein the hepatic virus is hepatic C virus.

4. The method of claim 1, wherein the sample comprises saliva or blood.

5. The method of claim 1, wherein detecting comprises performing at least one of selective hybridization and sequencing of at least a portion of the IL22RA2 gene locus containing at least one of the single nucleotide polymorphisms.

6. The method of claim 1, wherein the parasite is a *Schistosoma* parasite.

7. The method of claim 1, comprising detecting at least one additional single nucleotide polymorphism in the IL22RA2 gene locus of the biological sample, wherein the at least one additional single nucleotide polymorphism is rs7774663 having a genotype of CC.

8. The method of claim 1, comprising detecting at least one additional single nucleotide polymorphism in the IL22RA2 gene locus of the biological sample, wherein the at least one additional single nucleotide polymorphism is rs7774663 having a genotype of TT.

9. The method of claim 1, comprising detecting at least one additional single nucleotide polymorphism in the IL22RA2 gene locus of the biological sample, wherein the at least one additional single nucleotide polymorphism is rs6570136 having a genotype of GG.

10. The method of claim 1, comprising detecting at least two additional single nucleotide polymorphisms in the IL22RA2 gene locus of the biological sample, wherein the two additional single nucleotide polymorphisms are rs7774663 having a genotype of CC or TT, and rs6570136 having a genotype of GG.

11. The method of claim 1, wherein detecting comprises performing microsequencing of at least a portion of the IL22RA2 gene locus containing at least one of the single nucleotide polymorphisms.

12. The method of claim 1, wherein detecting comprises performing allele-specific amplification of at least a portion of the IL22RA2 gene locus containing at least one of the single nucleotide polymorphisms.

* * * * *